(12) United States Patent
Guttikonda et al.

(10) Patent No.: US 12,315,611 B2
(45) Date of Patent: *May 27, 2025

(54) SYSTEMS AND METHODS FOR REGULATING PROVISION OF MESSAGES WITH CONTENT FROM DISPARATE SOURCES BASED ON RISK AND FEEDBACK DATA

(71) Applicant: Click Therapeutics, Inc., New York, NY (US)

(72) Inventors: Sudheer Guttikonda, Edison, NJ (US); William Morse, New York, NY (US); Chuanhan Qiu, New York, NY (US); Austin Speier, Brooklyn, NY (US)

(73) Assignee: Click Therapeutics, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/939,143

(22) Filed: Nov. 6, 2024

(65) Prior Publication Data

US 2025/0118404 A1    Apr. 10, 2025

Related U.S. Application Data

(63) Continuation of application No. 18/750,013, filed on Jun. 21, 2024, which is a continuation of application
(Continued)

(51) Int. Cl.
*G16H 20/00* (2018.01)
*A61B 5/00* (2006.01)
(Continued)

(52) U.S. Cl.
CPC .......... *G16H 20/00* (2018.01); *A61B 5/4833* (2013.01); *A61B 5/7475* (2013.01); *G06F 40/40* (2020.01)

(58) Field of Classification Search
CPC ........ G16H 20/00; G16H 20/10; G16H 20/70; G16H 50/30; G16H 50/20; A61B 5/4833;
(Continued)

(56) References Cited

U.S. PATENT DOCUMENTS 6,039,688 A * 3/2000 Douglas ............... A61B 5/4866
600/300
9,449,150 B2 * 9/2016 Hyde ...................... G16H 20/10
(Continued)

FOREIGN PATENT DOCUMENTS

CA     3134521 A1    10/2020
CN    114796702 A     7/2022

OTHER PUBLICATIONS

Extended European Search Report on EP Appl. No. 24173574.5 dated Oct. 28, 2024.
(Continued)

*Primary Examiner* — Alaaeldin M. Elshaer
(74) *Attorney, Agent, or Firm* — Foley & Lardner LLP

(57) ABSTRACT

Aspects of the present disclosure are directed to systems, methods, and computer readable media for regulating digital therapeutic content for provision. A computing system may identify a digital therapeutic content to be provided via a network. The computing system may apply the digital therapeutic content to a machine learning (ML) model having a set of weights. The computing system may determine, from applying the digital therapeutic content to the ML model, an indication as of one of compliance or non-compliance. The computing system may store, using one or more data structures, an association between the digital therapeutic content and the indication used to control provision of the digital therapeutic content via the network, by (i) restricting the digital therapeutic content from provision responsive to determining the indication of non-compliance and (ii) permitting the digital therapeutic content to be
(Continued)

provided responsive to determining the indication of compliance.

26 Claims, 19 Drawing Sheets

Related U.S. Application Data

No. 18/377,931, filed on Oct. 9, 2023, now Pat. No. 12,040,063.

(51) Int. Cl.
*G06F 40/40* (2020.01)
*G16H 20/10* (2018.01)

(58) Field of Classification Search
CPC .. A61B 5/7475; G06Q 30/02; G06Q 30/0203; G06F 40/40; G06N 20/00
USPC .......................................... 705/2, 3
See application file for complete search history.

(56) References Cited

U.S. PATENT DOCUMENTS

| | | | | |
|---|---|---|---|---|
| 11,450,224 | B1* | 9/2022 | Jain | G06F 8/20 |
| 11,636,500 | B1* | 4/2023 | Jain | G06Q 30/0203 |
| | | | | 705/7.32 |
| 12,040,063 | B1 | 7/2024 | Guttikonda et al. | |
| 2017/0195739 | A1* | 7/2017 | Wessel | H04N 21/4882 |
| 2019/0043618 | A1 | 2/2019 | Vaughan et al. | |
| 2019/0080794 | A1* | 3/2019 | Moskowitz | G16H 20/70 |
| 2019/0088366 | A1 | 3/2019 | Vaughan et al. | |
| 2021/0004692 | A1* | 1/2021 | Ferrara | G06N 5/022 |
| 2021/0057057 | A1 | 2/2021 | Chin et al. | |
| 2021/0174924 | A1* | 6/2021 | Iyer | G16H 20/00 |
| 2022/0237368 | A1 | 7/2022 | Tran | |
| 2022/0383272 | A1* | 12/2022 | Dryman | G06Q 10/06393 |
| 2023/0092866 | A1* | 3/2023 | Vaughan | G06N 5/01 |
| | | | | 706/12 |
| 2023/0367969 | A1 | 11/2023 | Chaturvedi et al. | |

OTHER PUBLICATIONS

Final Office Action on U.S. Appl. No. 18/759,562 dated Dec. 31, 2024.

Kim et al., "Touching Minds: Deep Generative Models Composing the Digital Contents to Practice Mindfulness", https://link.springer.com/chapter/10.1007/978-3-030-98404-5_9https://doi.org/10.1007/978-3-030-98404-5_9 (Year: 2022).

Matheus Araujo et al: "ML Approach for Early Detection of Sleep Apnea Treatment Abandonment", Digital Health, ACM, 2 Penn Plaza, Suite 701 New Yorkny 10121-0701 USA, Apr. 23, 2018 (Apr. 23, 2018), pp. 75-79, XP058403367, DOI: 10.1145/3194658.3194681 ISBN: 978-1-4503-6493-5.

Non-Final Office Action on U.S. Appl. No. 18/377,905 dated Dec. 2, 2024.

Non-Final Office Action on U.S. Appl. No. 18/750,013 dated Sep. 6, 2024.

Non-Final Office Action on U.S. Appl. No. 18/377,931 dated Dec. 19, 2023.

Non-Final Office Action on U.S. Appl. No. 18/750,013 dated Aug. 19, 2024.

Non-Final Office Action on U.S. Appl. No. 18/759,562 dated Sep. 16, 2024.

Notice of Allowance on U.S. Appl. No. 18/377,905 dated Jun. 17, 2024.

Notice of Allowance on U.S. Appl. No. 18/377,931 dated Mar. 11, 2024.

Notice of Allowance on U.S. Appl. No. 18/750,013 dated Jan. 15, 2025.

Non-Final Office Action on U.S. Appl. No. 18/759,562 dated Apr. 11, 2025.

* cited by examiner

SYSTEMS AND METHODS FOR REGULATING PROVISION OF MESSAGES WITH CONTENT FROM DISPARATE SOURCES BASED ON RISK AND FEEDBACK DATA

CROSS REFERENCES TO RELATED APPLICATIONS

The present application claims priority under 35 U.S.C. § 120 as a continuation of U.S. patent application Ser. No. 18/750,013, titled "Systems and Methods for Regulating Provision of Messages with Content from Disparate Sources Based on Risk and Feedback Data," filed Jun. 21, 2024, which claims priority under 35 U.S.C. § 120 as a continuation of U.S. patent application Ser. No. 18/377,931, titled "Systems and Methods for Regulating Provision of Messages with Content from Disparate Sources Based on Risk and Feedback Data," filed Oct. 9, 2023, each of which is incorporated herein by reference in their entireties.

BACKGROUND

In a networked environment, a server can transmit a message to an end user device to provide various information to the end user. The content in the message may potentially contain erroneous or malicious information, or otherwise unsuitable to provide to the end user. In the context of digital therapeutics, the message may contain digital therapeutics content including inaccurate or superfluous information, for example, in relation to the end user's state, which may adversely impact the end user's state, such as degradation of the end user's condition or adherence to the digital therapeutic.

Due to the wide variety of complex and personalized subject matter included in an end user's digital therapeutic therapy regimen, the generation of information related to the individual's therapy regimen can be tedious and time consuming to create manually. Specifically for digital therapeutics, there may be multiple topic categories that can provide input for an effective therapy, factoring in knowledge from various sources. There is also a wide range of material used to develop the digital therapeutic in different media and formats. Intricacies of each individual end user and of the regimen can make content generation resource-intensive as well as prone to error. Furthermore, human-created content can suffer from a lack of scalability to a broader audience and at the same time insufficient specificity to a particular end user's condition.

Automated generation of digital therapeutic content using artificial intelligence (AI) techniques can be subject to similar difficulties, as well as the introduction of hallucinations, inaccurate subject matter, or improperly phrased or visualized content items. For example, AI generated content can contain inaccurate or insensitive subject matter and also may lack relevance to the end user. Furthermore, this problem may be exacerbated when multiple AI models are used to generate content items for the digital therapeutics regimen. It may be time-intensive and computationally difficult to parse through large sets of AI-generated content for inaccuracies, relevancy, and specificity.

The lack of accuracy, relevancy, and specificity in content manually created or automatically generated for an end user as well as the difficulties in regulating content at a greater scale for a digital therapeutics regimen can result in wasted consumption of computing resources (e.g., processor and memory) and network bandwidth by providing ineffective messages. From a human-computer interaction (HCI) perspective, these issues may potentially lead to lack of user interaction. In the context of digital therapeutics, users receiving such content may suffer from lower adherence to the treatment regimen, thereby leading to worsening or no improvement in the condition of the end user.

SUMMARY

To address these and other challenges, the service described herein can manage an interconnected architecture of multiple risk models based on multiple domains to evaluate content produced by human creators or generative AI (e.g., generative transformer models). Based on the evaluation, the service can determine which content, if any, to provide in a message (or an item of content) to an end user to address their specific condition for digital therapeutic applications. Furthermore, the service can provide suggestions to correct the content if any, and receive feedback on the provided content to iteratively train both the risk models and a generative AI model maintained by the message system. The content items created using generative transformer models (e.g., large language models or text-to-image models) may include content to be presented via the end user's device, with the aim of preventing, alleviating, or treating conditions of the end user. The content items may also include information provided for presentation on web pages and applications, separate from digital therapeutics regime provided to a particular user. By providing these functions, the service can improve the creation of digital therapeutic content and regulate the provision of digital therapeutic content through continuous learning in a single architecture.

The service may interface with a set of generative models as well as databases maintaining pre-generated content. To access the models or database, the service may receive an input from an administrator. The input may identify parameters to generate or identify digital therapeutic content, such as a targeted condition and a domain against which to evaluate the content. The input may be provided as a prompt to the generative transformer models. The prompt can be personalized based on the end user submitting the text input, thereby providing a curated input for the generative transformer models to create the content items. In addition, the system may use the input to search for the generated content items or previously generated content items from a database. In some embodiments, the service may determine that the text input corresponds to a content item already stored in the database and may not generate the prompt to provide to the generative transformer models. The service can identify a set of content items related to the text input from multiple sources, including content items generated by generative transformer models based on a prompt created from the input, from previously AI-generated content items, from human-created content items, or a combination thereof. The multitude of sources for the digital therapeutics content can vary, due to the intrinsic differences in training between AI models and human creators.

With the identification of content from AI or human sources, the service can validate whether the content is fit for providing to the end user (e.g., to aid the end user in alleviating or improving their condition). To validate, the service can select one or more risk models to apply to the content items to determine a risk score of each content item. Each risk model can be selected for different parameters of the content to provide a customized recommendation of which content items of the identified content items to provide in relation to the text input. For example, the service can select the risk model based on an audience indicated in the text input, a domain indicated in the text input, or the administrator providing the text input, among others. The messages provided to an end user during participation in a digital therapeutics regimen can fall under one or more domains, such as a regulatory domain, a medical domain, a product domain, or an audience experience domain. Selecting one or more risk models based on one or more domains indicated in the input provides further customization for the end user, which thereby may help improve adherence to the digital therapeutics regimen.

In lead-up to assessing content for risk, the set of risk models can be trained by the service to evaluate risk associated with each content item identified in accordance with the respective domains. Each risk model can be trained by the service on examples including content items to determine whether or not the content item should be provided to the end user. In some embodiments, the risk models can be provided a training data set including content items. Each content item can be associated with a label including an expected indication identifying compliance or non-compliance for provision. In some embodiments, the indication can include a risk score assigned to the content item for training purposes. The risk score can indicate compliance or non-compliance for provision, such that a risk score below a threshold risk score can indicate compliance. The risk models can be trained on multiple different content items with different corresponding domains, audiences, or combinations thereof, to produce a multitude of risk models, each tailored towards different content items.

During training, the service can apply the content item from each example to a risk model to determine a risk score or an indication of compliance for each content item for provision. The determined indication of compliance can be compared to the indication of compliance associated with the training content item. If the comparison shows that the determined indications correspond to the labeled indication in the training data, the service can determine that the risk model has successfully classified the content item. Otherwise, if the comparison shows that the determined indications correspond to the labeled indication in the training data, the service can determine that the risk model has not successfully classified the content item. The service can update the weights of the risk models accordingly. In addition, the risk models may be trained to provide or indicate portions of the content items which may be edited to change a non-compliant content item to a compliant content item and may present these portions to an administrator. For example, the risk models may be trained to present suggested edits, portions of the content item to change, or replacement words within the content item. The portions may be accepted or denied by the administrator to further aid in training the risk models. Furthermore, the training of the risk models may be partially interactive, and the administrator may provide feedback during training to maintain or correct the indications outputted by the risk model. The risk models can accept a response indicating that a content item indicated as compliant or non-compliant has been improperly classified. In this manner, the risk models can continuously learn to better determine compliant content items in furtherance of the digital therapeutic treatment regimen.

With the establishment of the risk models, the service can apply the content item to each risk model to generate a risk score for the content item. The risk score can be used to identify whether or not the content item should be provided to the end user. The risk score can be determined by the risk models by providing the content items to the risk models for evaluation. The risk models may also take additional inputs, such as information related to the end user, the text input, the individual generative transformer model which created the content item, or previous performance history of each generative transformer model. The service can select which risk models to apply based on the indicated domain from the input.

Based on the risk scores, the service may rank the content items and select a content item using the ranking. For example, the service may identify the content item corresponding to a highest ranking (e.g., lowest risk score) to provide to the end user. The service may also rank the content items based on other criteria, such as feedback from the audience to prior digital therapeutic content, audience preference for prior digital therapeutic content, an identification of the corresponding model used to generate the content item, or audience behavior in response to prior digital therapeutic content, among others. Through these means, the content provided to the end user can undergo various filtering, parsing, and content checks to ensure that the content provided to the end user is most effective for their digital therapeutics regimen.

With the selection of a content item based on its risk score, the service can present the content item to the administrator with its corresponding risk score. The service can generate instructions to display the content item on an administrator device. The display may include the selected content item, a respective risk score, a respective domain, a respective audience, among other information related to the selected content item. With the presentation, the administrator may provide an interaction with the administrator device to provide feedback regarding the selected content item. The interaction may include a modification to the content item, such as a modification of a visual, auditory, or haptic feature of the content item. From the interaction, the service can generate feedback data. The feedback data may include information, such as the content that was included in the message provided to the user, a modification of the content or a modification of the indication. The feedback data from the administrator can be used to update the generative transformer model itself. For instance, the service can use the feedback data to calculate a loss metric as a function of the feedback data, and then use the loss metric to update weights in the generative transformer model. The feedback data may also be used to generate subsequent prompts when creating messages for the end user using the generative transformer model. For example, the service can add at least a portion of the feedback data as part of the user information for the administrator or the message generation parameters when generating the prompt.

Upon receiving the feedback from the administrator or determining that there is no administrator feedback, the service may store the content item in a database of content items. The service may store the content item in association with the indication. The service may also store the content item with the indication denoting whether or not the content item is to be provided to the end user. For example, the service may store the content item in association with an indication of compliance, denoting that the content item may be provided to the end user.

With the storing of the content item, the service can send the message containing the content item for presentation on the end user device. Multiple content items can be presented in different mediums. For example, an application running on the end user device can present the content of the message. Upon presentation via the end user device, the message can direct the end user to perform an activity in furtherance of the digital therapeutic therapy regimen. The application on the end user device can monitor for interactions by the end user with the message or the application itself. The interaction can include, for example, an indication that a specified activity has been performed or an input of the end user's reaction to the presentation of the message, among other responses. Using the detected interactions, the application can generate and send a response to provide to the service.

In addition, the service may send the message to the end user device for presentation to a wider audience. For example, the service may send the message including the content items on publicly accessible webpages, such as main articles and auxiliary content (e.g., within inline frames on webpages). The content item can include information on a clinical trial for participants for the digital therapeutics application. The content items may be transmitted for publishing, such as in a medical journal, newspaper, or online database. For example, the content items may be included as the primary content on a webpage or as supplemental content inserted within a portion (e.g., an inline frame) of the webpage. The content items may be presented across a wide array of media.

Upon receipt, the service can use the response from the end user device to update the generative transformer model itself. The service can parse the response of the end user device to generate feedback data. The feedback data may include information, such as the content that was included in the message provided to the user and an indication whether the end user performed the activities specified in the content of the message. The feedback data can be used to update the generative transformer model itself. For instance, the service can use the feedback data to calculate a loss metric as a function of the feedback data, and then use the loss metric to update weights in the generative transformer model. The feedback data may also be used to generate subsequent prompts when creating messages for the end user using the generative transformer model. For example, the service can add at least a portion of the feedback data as part of the user information or the message generation parameters when generating the prompt. The service can combine the feedback data from any number of previously presented messages when creating the prompt to input into the generative transformer model.

In this manner, the service may iteratively and continuously factor in feedback from response data of the administrator prior to provisioning the content and feedback data from the end user upon providing the content into both the generative transformation model maintained by the service and the risk models. Outputs from the risk models can be provided to the generative transformation model to continuously train the generative transformation model for a variety of domains, audiences, and text inputs. This technical solution enables content generated by other AI models (in addition to content generated by the generative transformer model maintained by the messaging system) to be validated as compliant and thereafter ranked amongst each other to determine the most relevant content to provide to the end user.

Additionally, relative to human moderation of content, this technical solution may enable scalability for the creation of personalized digital therapeutics content by enabling a large variety of individualized content to be generated and validated for providing to the end user. Providing more pertinent content can reduce resource consumption by reducing computational power expended on generating and transmitting irrelevant messages to end users. The enablement of flexibility, scalability, and specificity can optimize or reduce consumption of computing resources (e.g., processor and memory) and network bandwidth that would have been otherwise wasted from providing ineffective content.

In the context of digital therapeutics, the new generation of content may account for changes to the end user's state, such as improvement or degradation of the end user's condition or progression through the therapy regimen. By iteratively incorporating feedback to continuously train the generative transformer model and the risk models, the HCI can be improved by providing content which is more relevant and accurate for a particular end user. The content provided by leveraging of the risk models can yield higher quality of interactions by the end user with the application. In addition, the increase in engagement can result in higher levels of adherence of the end user with the therapy regimen, thereby leading to a greater likelihood in preventing, alleviating, or treating conditions of the end user.

Aspects of the present disclosure are directed to systems, methods, and computer readable media for configuring generation of digital therapeutic content for provision. A computing system may receive, via a user interface, a text input including one or more parameters. The one or more parameters may identify an audience for which digital therapeutic content is to be generated and at least one domain of a set of domains with which to test the digital therapeutic content for risk. The set of domains can include a regulatory domain and a medical domain. The computing system may identify a set of content items generated by a corresponding set of generative transformer models each using a prompt created based on the text input. Each of the set of content items may include respective digital therapeutic content generated from a respective model of the set of generative transformer models. The computing system may select, from a set of risk models for the set of domains, at least one risk model corresponding to the at least one domain. The computing system may apply the at least one risk model to each content item of the set of content items to determine a corresponding risk score. The computing system may select, from the set of content items, a content item based on the risk score of the content item. The computing system may present, via the user interface, the content item including the respective digital therapeutic content.

In some embodiments, the computing system may retrieve, using the text input, at least one content item previously generated and stored on a database. The computing system may add, responsive to determining that a second risk score of the at least one content item satisfies a second threshold, the at least one content item to the set of content items. In some embodiments, the computing system may determine that no previously generated content items are stored on the database corresponding to the text input. The computing system may invoke, responsive to determining that no previously generated content items are stored, the set of generative transformer models to generate the set of content items using the prompt created based on the text input.

In some embodiments, the computing system may apply a second risk model to the one or more parameters of the text input to determine a second risk score. The computing system may present, via the interface, an indication that the second risk score exceeds a threshold. In some embodiments, the computing system may apply a multitude of risk models associated with the set of domains to the content item to determine a corresponding set of risk scores. The set of domains may further include a product domain and an audience experience domain. The computing system may present, via the user interface, information identifying the set of risk scores for the content item.

In some embodiments, the computing system may rank the set of content items based on at least one of (i) feedback from the audience to prior digital therapeutic content, (ii) audience preference for prior digital therapeutic content, (iii) an identification of the corresponding model used to generate the content item, and (iv) audience behavior in response to prior digital therapeutic content. In some embodiments, the computing system may apply a second risk model to the one or more parameters of the text input to determine a second risk score. The computing system may apply the set of generative models to generate the set of content items, responsive to the second risk score satisfying a threshold.

In some embodiments, the computing system may receive, via the user interface, information identifying one or more portions to be modified in the content item. The computing system may store, on a database, an association of the information with the content item. In some embodiments, the computing system may identify, from the set of generative transformer models, a generative transformer model to be updated based on at least one of the text input, the content item, or responses from presentation of the content item. The computing system may provide at least a portion of the text input, the content item, or response data to update the generative transformer model identified from the set of generative transformer models.

In some embodiments, each content item of the set of content items may include at least one of textual content or visual content to be provided to a device for presentation in a session to address a condition of the audience, wherein the audience is on a medication to address a condition at least in a partial concurrence with the session.

Aspects of the present disclosure are directed to systems, methods, and computer readable media for regulating digital therapeutic content for provision. A computing system may identify a first digital therapeutic content to be provided via a network. The computing system may apply the first digital therapeutic content to a machine learning (ML) model having a set of weights to generate a first output. The ML model may be trained by identifying a training dataset including a set of examples, each example of the set of examples identifying a respective second digital therapeutic content and a first indication identifying one of compliance or non-compliance for provision. The ML model may be trained by applying the second digital therapeutic content from an example of the set of examples of the training dataset into the ML model to generate a second output. The ML model may be trained by determining, from the second output, a second indication of one of compliance or non-compliance of the second digital therapeutic content used to control provision. The ML model may be trained by comparing the first indication from the example of the training dataset with the second indication determined by the ML model. The ML model may be trained by updating at least one of the set of weights of the ML model in accordance with the comparison. The computing system may determine, from applying the first digital therapeutic content to the ML model, an indication as of one of compliance or non-compliance. The computing system may store, using one or more data structures, an association between the first digital therapeutic content and the indication used to control provision of the first digital therapeutic content via the network, by (i) restricting the first digital therapeutic content from provision responsive to determining the indication of non-compliance and (ii) permitting the first digital therapeutic content to be provided responsive to determining the indication of compliance.

In some embodiments, the computing system may receive an identification of the first digital therapeutic content as associated with at least one domain of a set of domains. The computing system may select, from a plurality of ML models, the ML model corresponding to the domain to apply to the first digital therapeutic content. The computing system may determine the indication by determining the indication as one of compliance or non-compliance with respect to the domain. In some embodiments, the computing system may generate, from applying the ML model, one or more portions to modify in the first digital therapeutic content, responsive to determining the indication of non-compliance of the first digital therapeutic content.

In some embodiments, the computing system may select, from a set of content items, one of a first content item or a second content item as the first digital therapeutic content for provision based on an indication of compliance or non-compliance of each of the set of content items determined using the ML model. In some embodiments, the computing system may receive, via a user interface, a selection of a second indication identifying the first digital therapeutic content as compliant or non-compliant. The computing system may override the indication from the ML model with the second indication received via the user interface.

In some embodiments, each example of the set of examples of the training dataset further identifies a first risk score identifying a degree of compliance or non-compliance for provision for the second digital therapeutic content. The computing system may determine the second indication by determining a second risk score identifying the degree of compliance or non-compliance for provision for the first digital therapeutic content. In some embodiments, the first digital therapeutic content may include at least one of textual content or visual content to be provided to a device for presentation in a session to address a condition of an audience, wherein the audience is on a medication to address a condition at least in a partial concurrence with the session.

Aspects of the present disclosure are directed to systems, methods, and computer readable media for regulating provision of digital therapeutic content. A computing system may identify a training dataset including a set of examples, each example of the set of examples identifying a respective first digital therapeutic content and a first indication identifying one of compliance or non-compliance to control provision of the first digital therapeutic content via a network, by (i) restricting the first digital therapeutic content from provision when non-compliant and (ii) permitting the first digital therapeutic content to be provided when compliant. The computing system may apply the first digital therapeutic content from an example of the set of examples of the training dataset into a machine learning (ML) model including a set of weights to generate an output. The computing system may determine a second indication of one of compliance or non-compliance of the first digital therapeutic content used to control provision. The computing system may compare the first indication from the example of the training dataset with the second indication determined by the ML model. The computing system may update at least one of the set of weights of the ML model in accordance with the comparison between the first indication and the second indication. The computing system may store the set of weights of the ML model to apply to determine compliance or non-compliance of second digital therapeutic content.

In some embodiments, the computing system may receive, via a user interface, a selection of an indication identifying the second digital therapeutic content as compliant or non-compliant. The computing system may compare the indication determined from the output of the ML model and the indication from the user interface. The computing system may retrain the ML model in accordance with the comparison. In some embodiments, the computing system may generate, from applying the ML model, one or more portions to modify in the second digital therapeutic content, responsive to determining the indication of non-compliance of the second digital therapeutic content.

In some embodiments, the computing system may re-train the ML model using the one or more portions to modify the second digital therapeutic content. In some embodiments, the computing system may modify a prompt applied to a generative transformer model used to output the first digital therapeutic content, responsive to determining the non-compliance for the second digital therapeutic content, wherein the generative transformer model is a part of or separate from the ML model. In some embodiments, the computing system may retrain a generative transformer model used to generate the first digital therapeutic content, based on the indication of one of non-compliance or compliance for the second digital therapeutic content.

In some embodiments, each example of the set of examples of the training dataset may further identify a first risk score identifying a degree of compliance or non-compliance for provision for the first digital therapeutic content. The computing system may apply the first digital therapeutic content from an example of the set of examples of the training dataset to the ML model to determine a second risk score identifying the degree of compliance or non-compliance for provision for the first digital therapeutic content. The computing system may update at least one of the set of weights of the ML model in accordance with a comparison between the first risk score and the second risk score for the example.

In some embodiments, each example of the set of examples of the training dataset may include an identification of the first digital therapeutic content as a domain of a set of domains and the first indication identifying one of compliance or non-compliance with respect to the domain. The computing system may identify, from a set of ML models, the ML model corresponding to the domain to apply to the first digital therapeutic content. The computing system may determine the second indication by determining the second indication of one of compliance or non-compliance of the first digital therapeutic.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

For purposes of reading the description of the various embodiments below, the following enumeration of the sections of the specification and their respective contents may be helpful:

Section A describes systems and methods for generating and regulating content for messages targeted to address conditions in users;

Section B describes systems and methods for training and applying validation models for content; and Section C describes a network and computing environment which may be useful for practicing embodiments described herein.

Figure 1:
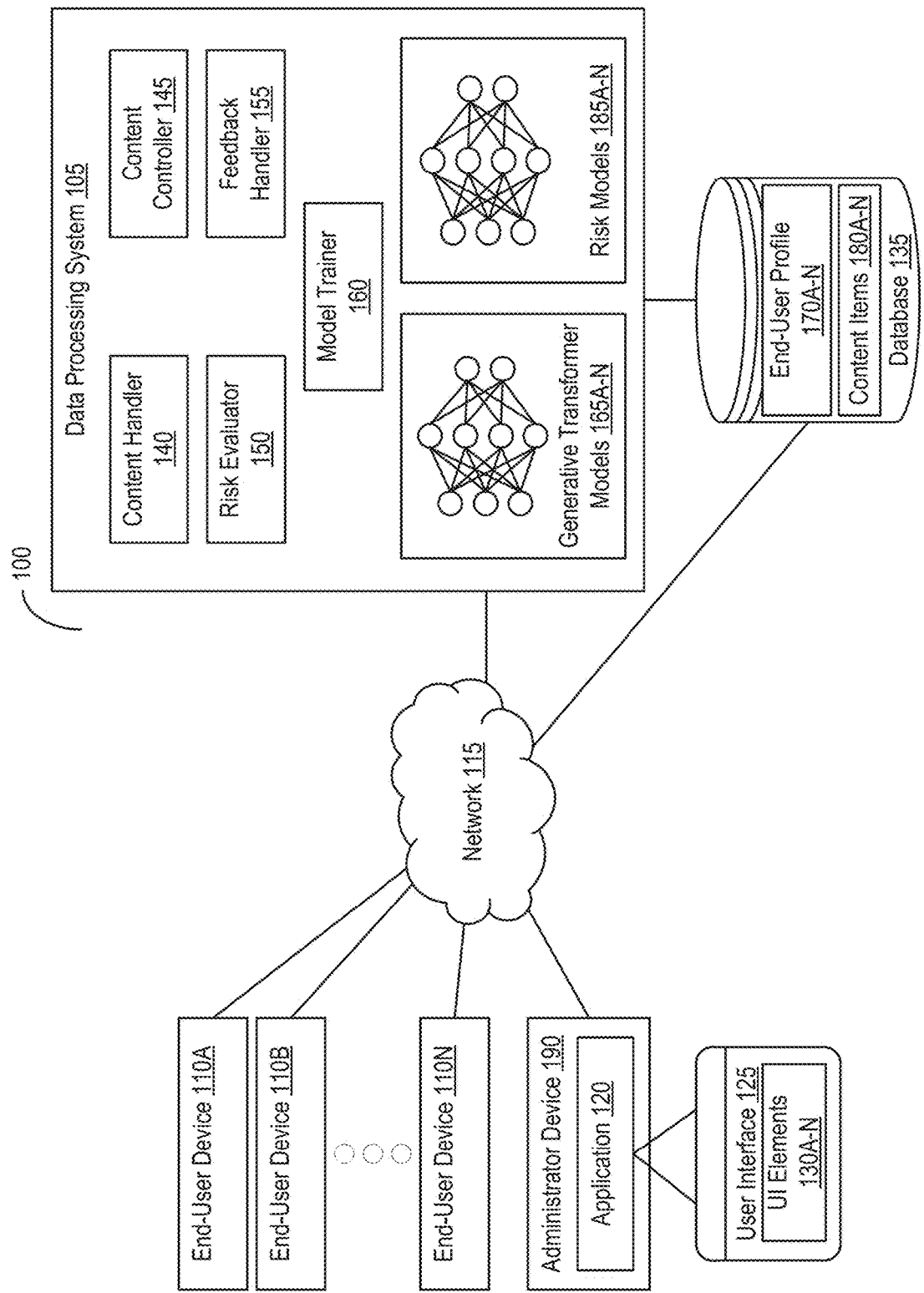
FIG. 1 depicts a block diagram of a system for generating and regulating content for messages targeted at addressing conditions in users in accordance with an illustrative embodiment.

A. Systems and Methods for Generating and Regulating Content for Messages Targeted to Address Conditions in Users Referring now to FIG. 1, depicted is a block diagram of a system 100 for generating and regulating content for messages targeted at addressing conditions in end users. In an overview, the system 100 may include at least one data processing system 105, a set of end user devices 110A-N (hereinafter generally referred to as end user devices 110), and at least one administrator device 190 communicatively coupled with one another via at least one network 115. The administrator device 190 may include at least one application 120. The application 120 may include or provide at least one user interface 125 with one or more user interface (UI) elements 130A-N (hereinafter generally referred to as UI elements 130). The data processing system 105 may include at least one content handler 140, at least one content controller 145, at least one risk evaluator 150, at least one feedback handler 155, at least one model trainer 160, at least one generative transformer model 165A-N, and at least one risk model 185A-N, among others. The data processing system 105 may include or have access to at least one database 135. The database 135 may store, maintain, or otherwise include one or more end user profiles 170A-N (hereinafter generally referred to as end user profiles 170) and one or more content items 180A-N, among others. The functionalities of the application 120 on the administrator device 190 may be performed in part on the data processing system 105, and vice-versa.

Within the data processing system 105, the content handler 140 may receive input to generate the content items 180 through the generative transformer models 165A-N (hereinafter generally referred to as the generative transformer model(s) 165) and may provide selected content items 180 related to a session initiated by an administrator of the application 120 on the administrator device 190. The content controller 145 may identify the content items 180. The risk evaluator 150 may apply the risk models 185A-N to determine a risk score of each of the content items 180. The feedback handler 155 may generate feedback using responses from the administrator device 190 to update the generative transformer model 165, the content items 180, or the risk models 185A-N (hereinafter generally referred to as the risk model(s) 185). The model trainer 160 may train, improve, or update the generative transformer model 165 or the risk models 185 related to a session initiated by an administrator of the application 120.

In further detail, the data processing system 105 may be any computing device comprising one or more processors coupled with memory and software and capable of performing the various processes and tasks described herein. The data processing system 105 may be in communication with the one or more user devices 110, the administrator device 190, and the database 135 via the network 115. The data processing system 105 may be situated, located, or otherwise associated with at least one computer system. The computer system may correspond to a data center, a branch office, or a site at which one or more computers corresponding to the data processing system 105 is situated.

The end user device 110 may be any computing device comprising one or more processors coupled with memory and software and capable of performing the various processes and tasks described herein. The end user device 110 may be in communication with the data processing system 105, the administrator device 190, and the database 135 via the network 115. The end user device 110 may be a smartphone, other mobile phone, tablet computer, wearable computing device (e.g., smart watch, eyeglasses), or laptop computer. The end user device may be provided with one or more content items 180 via the data processing system 105, or the end user device may request one or more content items 180 via an interaction with the data processing system 105, such as via an application associated with the end user devices 110.

The administrator device 190 may be any computing device comprising one or more processors coupled with memory and software and capable of performing the various processes and tasks described herein. The administrator device 190 may be associated with an entity interfacing with the data processing system 105 to control and regulate generation of content items 180. The administrator device 190 may be in communication with the data processing system 105, the user devices 110, and the database 135 via the network 115. The administrator device 190 may be a smartphone, other mobile phone, tablet computer, wearable computing device (e.g., smart watch, eyeglasses), or laptop computer. The administrator device 190 may be used to access the application 120. In some embodiments, the application 120 may be downloaded and installed on the administrator device 190 (e.g., via a digital distribution platform). In some embodiments, the application 120 may be a web application with resources accessible via the network 115.

The application 120 executing on the administrator device 190 may interface with the data processing system 105 to generate or modify one or more content items 180. In some embodiments, the application 120 may be an application to generate one or more messages for providing to an audience that is an end user associated with the end user device 110 in conjunction with a digital therapeutics application to address at least one condition of the end user. The condition of the end user may include, for example, chronic pain (e.g., associated with or include arthritis, migraine, fibromyalgia, back pain, Lyme disease, endometriosis, repetitive stress injuries, irritable bowel syndrome, inflammatory bowel disease, and cancer pain), a skin pathology (e.g., atopic dermatitis, psoriasis, dermatillomania, and eczema), a cognitive impairment (e.g., mild cognitive impairment (MCI), Alzheimer's, multiple sclerosis, and schizophrenia), a mental health condition (e.g., an affective disorder, bipolar disorder, obsessive-compulsive disorder, borderline personality disorder, and attention deficit/hyperactivity disorder), a substance use disorder (e.g., opioid use disorder, alcohol use disorder, tobacco use disorder, or hallucinogen disorder), and other conditions (e.g., narcolepsy and oncology or cancer), among others.

The end user may be at least partially concurrently taking medication to address the condition. For instance, if the medication is for pain, the end user may be taking acetaminophen, a nonsteroidal anti-inflammatory composition, an antidepressant, an anticonvulsant, or other composition, among others. For skin pathologies, the end user may be taking a steroid, antihistamine, or topic antiseptic, among others. For cognitive impairments, the end user may be taking cholinesterase inhibitors or memantine, among others. For narcolepsy, the end user may be taking a stimulant or antidepressant, among others. The end user may also participate in other psychotherapies for these conditions. In some embodiments, the content items 180 may be provided to the end user within the digital therapeutics application towards achieving an endpoint of the end user. An endpoint can be, for example, a physical or mental goal of an end user, a completion of a medication regimen, or an endpoint indicated by a doctor or an end user. At least one of the end user devices 110 may have a digital therapeutics application and may provide a session (sometimes referred to herein as a therapy session) to address at least one condition of the end user.

In some embodiments, the application 120 may be an application to generate one or more content items 180 for submission to a medical journal, governmental agency, or subject matter expert. The application 120 may be an application to generate or modify summaries associated with one or more of a clinical trial, test trial, journal entries or publications, among others. For example, the application 120 may be an application to generate a clinical summary report for subject matter related to conditions of patients, medications, psychotherapy, or treatments, among others.

The application 120 can include, present, or otherwise provide a user interface 125 including the one or more user interface elements 130A-N (hereinafter generally referred to as UI elements 130) to an administrator of the administrator device 190 in accordance with a configuration on the application 120. The UI elements 130 may correspond to visual components of the user interface 125, such as a command button, a text box, a check box, a radio button, a menu item, and a slider, among others. In some embodiments, the administrator may interact with the UI elements 130 to provide feedback, responses, or other interactions to generate and modify the content items 180 while interfacing with the data processing system 105.

The database 135 may store and maintain various resources and data associated with the data processing system 105 and the application 120. The database 135 may include a database management system (DBMS) to arrange and organize the data maintained thereon, as the end user profiles 170, the content items 180, the risk models 185, or the generative transformer models 165, among others. The database 135 may be in communication with the data processing system 105, the administrator device 190, and the one or more end user devices 110 via the network 115. While running various operations, the data processing system 105 and the application 120 may access the database 135 to retrieve identified data therefrom. The data processing system 105 and the application 120 may also write data onto the database 135 from running such operations.

On the database 135, each end user profile 170 (sometimes herein referred to as an end user account or end user information) can store and maintain information related to an end user through end user device 110. Each end user profile 170 may be associated with or correspond to a respective end user provided with the content items 180. The end user profile 170 may identify various information about the end user, such as an end user identifier, a condition to be addressed, information on sessions conducted by the end user (e.g., activities or lessons completed, or other content items 180 generated or modified by the administrator), preferences, user trait information, and a state of progress (e.g., completion of endpoints) in addressing the condition, among others. The information on a session may include various parameters of previous sessions performed by the end user and may be initially null. The preferences can include message preferences. The message preferences may include treatment preferences and end user input preferences, such as types of messages or timing of messages preferred. The message preferences can also include preferences determined by the data processing system 105, such as a type of message the end user may respond to. The preferences can include summary preferences, such as words, phrases, or content items 180 preferred by the administrator for inclusion in a content item 180. The end user profile 170 may be continuously updated by the application 120 and the data processing system 105.

In some embodiments, the end user profile 170 may identify or include information on a treatment regimen undertaken by the end user, such as a type of treatment (e.g., therapy, pharmaceutical, or psychotherapy), duration (e.g., days, weeks, or years), and frequency (e.g., daily, weekly, quarterly, annually), among others. The end user profile 170 can include at least one activity log of messages provided to the end user, interactions by the end user identifying performance of the specific end user, and responses from the end user device 110 associated with the end user, among others. The end user profile 170 may be stored and maintained in the database 135 using one or more files (e.g., extensible markup language (XML), comma-separated values (CSV) delimited text files, or a structured query language (SQL) file). The end user profile 170 may be iteratively updated as the end user performs additional sessions, provides inputs, or responds to the content items 180.

The content items 180 may be in any modality, such as text, image, audio, video, or multimedia content, among others, or any combination thereof. The content items 180 can be stored and maintained in the database 135 using one or more files. For instance, for text, the content items 180 can be stored as text files (TXT), rich text files (RTF), extensible markup language (XML), and hypertext markup language (HTTP), among others. For an image, the content items 180 may be stored as a joint photographic experts' group (JPEG) format, a portable network graphics (PNG) format, a graphics interchange format (GIF), or scalable vector graphics (SVG) format, among others. For audio, the content items 180 can be stored as a waveform audio file (WAV), motion pictures expert group formats (e.g., MP3 and MP4), and Ogg Vorbis (OGG) format, among others. For video, the content items 180 can be stored as a motion pictures expert group formats (e.g., MP3 and MP4), Quick-Time movie (MOV), and Windows Movie Video (WMV), among others. For multimedia content, the content items content items 180 can be an audio video interleave (AVI), motion pictures expert group formats (e.g., MP3 and MP4), QuickTime movie (MOV), and Windows Movie Video (WMV), among others.

Each content item 180 may identify or include information to be presented via the end user device 110 or the administrator device 190. For example, the content items 180 may be presented to an end user or administrator through a message transmitted to the end user device 110 or the administrator device 190, respectively. The message may be in any format, such as a short message/messaging service (SMS), a multimedia messaging service (MMS), or as an instruction to present via a display associated with the end user device 110 or the administrator device 190, among others.

The content items 180 of the message may include reminders to perform a task of the session. The message may be derived from a library of pre-generated psychotherapy messages or a library of pre-generated engagement (reminder) messages. The message may include reminders for the end user to complete the therapy sessions, to take medication, or to complete a task of the regimen. The message may include an activity for the end user to perform or a lesson for the end user to engage with. The content items 180 may also include a mechanism for responding, such as a link, chat box, or indication to respond to the message.

The content items 180 may include or correspond to one or more texts such as articles, summaries, or publications. For example, the content items 180 can include research articles, review articles, case reports, clinical trial protocols, or editorials, among others. The content items 180 can include texts for submission to governmental agencies, subject matter experts, scientific journals, or conferences, among others. For example, the content items 180 can include clinical trial protocols related to a treatment provided for a condition of an end user for submission to the Food and Drug Administration (FDA), a medical journal, or for internal distribution.

The content items 180A-N may be generated and stored in the database 135 prior during the session to generate and modify the content items 180 operating on the administrator device 190. The content items 180 can be human-created, computer-generated, or a combination thereof. In some embodiments, an administrator can provide the content items 180 through the application 120 operating on the administrator device 190. For example, the administrator may upload, provide, or transfer one or more content items 180 to the application 120 for storage in the database 135 during the session to generate and modify the content items 180. The content items 180 can be computer-generated, such as by the generative transformer model 165. In some embodiments, the administrator may provide inputs through the application 120 operating on the administrator device 190 to create one or more content items 180 using the generative transformer model 165. For example, the administrator can provide text, images, videos, or other presentations as input to generate the content items 180. The one or more generative transformer models 165 can generate one or more content items 180 from a prompt created by the input from the administrator. In some embodiments, the data processing system 105 can modify the input to include additional information to generate the prompt to provide to the generative transformer models 165. Each generative transformer model 165 can generate one or more content items 180 based on the provided prompt.

The generative transformer model 165 may receive inputs in the form of a set of strings (e.g., from a text input) to output content (e.g., the content items 180) in one or more modalities (e.g., in the form of text strings, audio content, images, video, or multimedia content). The generative transformer model 165 may be a machine learning model in accordance with a transformer model (e.g., generative pretrained model or bidirectional encoder representations from transformers). The generative transformer model 165 can be a large language model (LLM), a text-to-image model, a text-to-audio model, or a text-to-video model, among others. In some embodiments, the generative transformer model 165 can be a part of the data processing system 105 (e.g., as depicted). In some embodiments, the generative transformer model 165 can be part of a server separate from and in communication with the data processing system 105 via the network 115.

One or more of the generative transformer models 165 can be trained and maintained by the data processing system 105. The generative transformer model 165 can include a set of weights arranged across a set of layers in accordance with the transformer architecture. Under the architecture, the generative transformer model 165 can include at least one tokenization layer (sometimes referred to herein as a tokenizer), at least one input embedding layer, at least one position encoder, at least one encoder stack, at least one decoder stack, and at least one output layer, among others, interconnected with one another (e.g., via forward, backward, or skip connections). In some embodiments, the generative transformer layer 165 can lack the encoder stack (e.g., for an encoder-only architecture) or the decoder stack (e.g., for a decoder-only model architecture). The tokenization layer can convert raw input in the form of a set of strings into a corresponding set of word vectors (also referred to herein as tokens or vectors) in an n-dimensional feature space. The input embedding layer can generate a set of embeddings using the set of words vectors. Each embedding can be a lower dimensional representation of a corresponding word vector and can capture the semantic and syntactic information of the string associated with the word vector. The position encoder can generate positional encodings for each input embedding as a function of a position of the corresponding word vector or by extension the string within the input set of strings.

Continuing on, in the generative transformer model 165, an encoder stack can include a set of encoders. Each encoder can include at least one attention layer and at least one feed-forward layer, among others. The attention layer (e.g., a multi-head self-attention layer) can calculate an attention score for each input embedding to indicate a degree of attention the embedding is to place focus on and generate a weighted sum of the set of input embeddings. The feed-forward layer can apply a linear transformation with a non-linear activation (e.g., a rectified linear unit (ReLU)) to the output of the attention layer. The output can be fed into another encoder in the encoder stack in the generative transformer layer 165. When the encoder is the terminal encoder in the encoder stack, the output can be fed to the decoder stack.

The decoder stack can include at least one attention layer, at least one encoder-decoder attention layer, and at least one feed-forward layer, among others. In the decoder stack, the attention layer (e.g., a multi-head self-attention layer) can calculate an attention score for each output embedding (e.g., embeddings generated from a target or expected output). The encoder-decoder attention layer can combine inputs from the attention layer within the decoder stack and the output from one of the encoders in the encoder stack, and can calculate an attention score from the combined input. The feed-forward layer can apply a linear transformation with a non-linear activation (e.g., a rectified linear unit (ReLU)) to the output of the encoder-decoder attention layer. The output of the decoder can be fed to another decoder within the decoder stack. When the decoder is the terminal decoder in the decoder stack, the output can be fed to the output layer.

The output layer of the generative transformer model 165 can include at least one linear layer and at least one activation layer, among others. The linear layer can be a fully connected layer to perform a linear transformation on the output from the decoder stack to calculate token scores. The activation layer can apply an activation function (e.g., a softmax, sigmoid, or rectified linear unit) to the output of the linear function to convert the token scores into probabilities (or distributions). The probability may represent a likelihood of occurrence for an output token, given an input token. The output layer can use the probabilities to select an output token (e.g., at least a portion of output text, image, audio, video, or multimedia content with the highest probability). Repeating this over the set of input tokens, the resultant set of output tokens can be used to form the output of the overall generative transformer model 165. While described primarily herein in terms of transformer models, the data processing system 105 can use other machine learning models to generate and output content. In some implementations, the data processing system 105 may use one or more models maintained by external systems to generate and output content. For example, the data processing system may generate content using one or more models like ChatGPT produced by OpenAI, BARD produced by Google, or LLaMA produced by Meta, among others.

Each generative transformer model 165 can produce one or more of the content items 180 based on a prompt provided to the generative transformer models 165. Each content item 180 produced from a prompt created from a text input provided to the data processing system 105 can differ, due to differences in each of the generative transformer models 165. As such, a content item 180A may be more suitable than other content items 180B-N for providing to the end user (through first the administrator via the user interface 125). For example, the content items 180 generated by the generative transformer models 165 may include inaccuracies, irrelevant content, or hallucinations. In some embodiments, a content item 180A generated by a generative transformer model 165A may not be relevant for a particular user due to information within the content item 180A, the condition addressed by the content item 180A, a presentation style of the content item 180A, or grand assertions provided by the content item 180A. For example, the content item 180A may assert that it is the "best" method of treatment for a given condition; however, this cannot be asserted and provides false information. For example, the content item 180A may recommend to a user to consume a meat-based dish, without recognizing that the user has previously indicated vegetarianism. For example, the content item 180A may be in a textual presentation style, although previous behavior of the user from prior sessions indicates that the user adheres more consistently to sessions when video content is presented. For example, the content item 180A may generate data which is not substantiated or proven to be true. To moderate the content items 180 produced by the generative transformer models 165, the data processing system 105 may train and employ one or more risk models 185 to the content items 180 to determine a risk score associated with each content item 180.

Each risk model 185 can be a machine learning model trained to determine a risk score associated with a content item 180, the prompts, or a combination thereof. The risk models 185 can be trained as described herein (such as in conjunction with the training of the validation models) to calculate a risk score of a content item 180, a prompt, or a combination thereof. The risk scores generated by the risk models 185 can further be used to continuously train the generative transformer models 165 to provide more relevant, more accurate, or less risky content items 180 over time. The risk models 185 can include one or more natural language models, including the generative transformer models 165 described herein. The risk models 185 can include one or more classifier models such as Naive Bayes Classifier, support vector machine (SVM) ensemble classifier, kernel approximation, k-nearest neighbors' classifiers, or decision trees, among others.

One or more of the risk models 185 can accept the prompts as input. By accepting the prompts as input, the one or more risk models 185 can generate a risk score associated with a likelihood of a particular prompt to generate a desired content item 180. A desired content item 180 can include the content items 180 in a format specified by the prompt, for a group of people or an audience specified in the prompt, for a domain specified in the prompt, with a desired accuracy (e.g., correct information, relevant datasets), or with a desired relevancy (e.g., for an end user receiving the content items 180 as a part of a digital therapeutics session or an administrator receiving a text in a desired article type), among others. One or more of the risk models 185 can accept the generated content items 180 as input. By accepting the content items 180 as input, the one or more risk models 185 can generate a risk score associated with a likelihood that the content item 180 is a desired content item 180, as described above.

Figure 2:
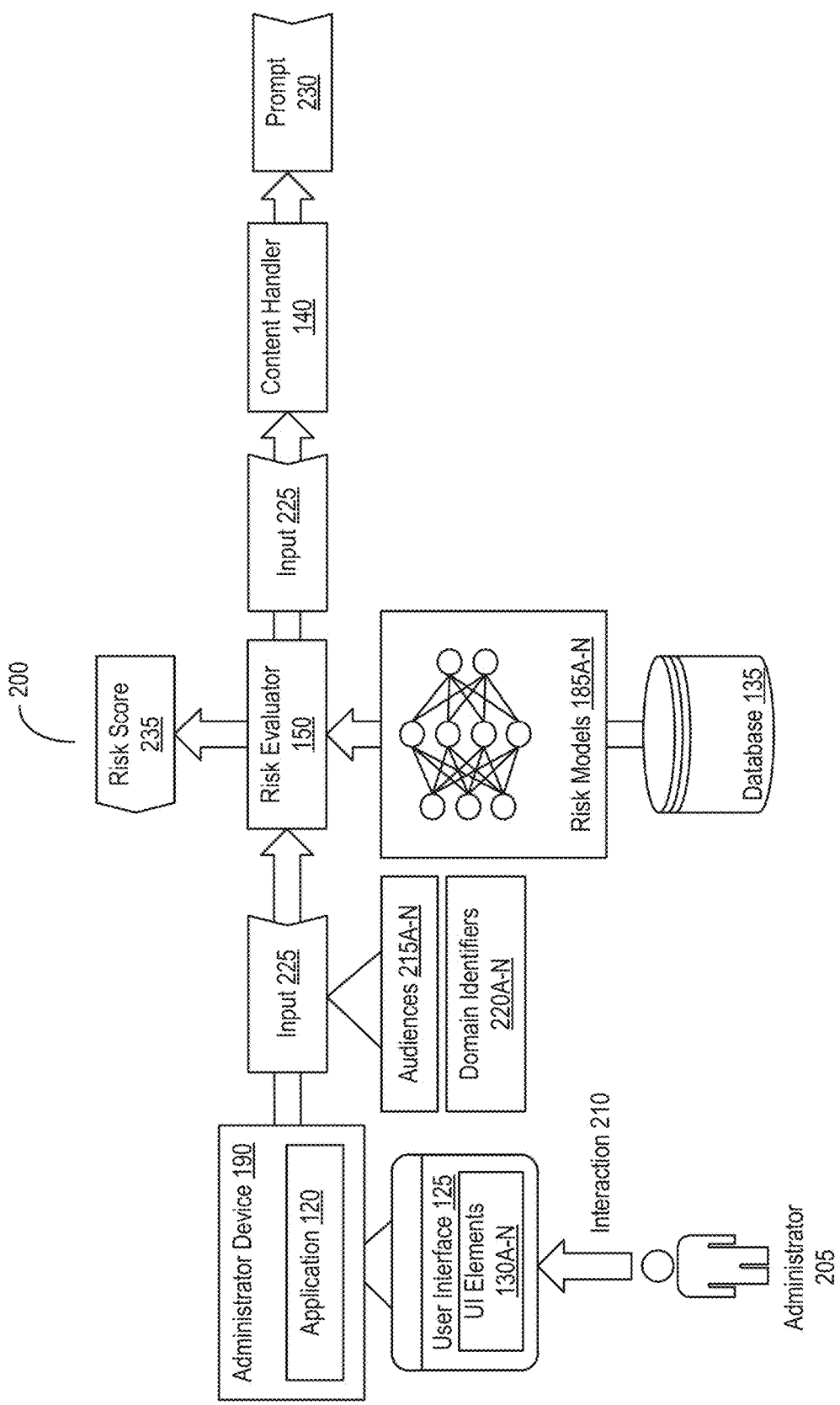
FIG. 2 depicts a block diagram for a process to identify content in the system for generating and regulating content for targeted messages in accordance with an illustrative embodiment.

Referring now to FIG. 2, depicted is a block diagram for a process 200 to identify content in the system 100 for generating and regulating content for targeted messages. The process 200 may include or correspond to operations performed in the system 100 to generate and regulate content for targeted messages. Under process 200, the content handler 140 can receive, retrieve, or identify a text input with which to create a prompt 230 to provide to the generative transformer models 165. The risk evaluator 150 may generate a risk score 235 for the prompt 230 using the risk models 185.

The administrator 205 may provide an interaction 210 with the user interface 125 via the UI elements 130 to generate or modify the content items 180. The interaction 210 can be a part of a request to generate or modify an activity or message presented. For example, the interaction 210 can be provided in response to a presentation by the application 120 to generate or modify the content items 180 on the administrator device 190. The interaction 210 can include interactions with the UI elements 130. In some embodiments, the interaction 210 can include the administrator 205 providing text through a text box, drop down menu, or speech-to-text, among others, through the user interface 125. In some embodiments, the interaction 210 can include the administrator 205 making a selection via a drop-down box, a button, or another UI element 130. For example, the interaction 210 can include the administrator 205 making a selection of a type of content item 180 (e.g., a journal article, clinical study report, etc.).

The application 120 operating on the administrator device 190 can accept the interaction 210 and can generate a text input 225 based on the interaction 210. In some embodiments, the interaction 210 includes a text input which the application 120 can utilize in creating the input 225. In some embodiments, the application 120 generates the input 225 from a non-text interaction, such as a selection of a button or drop down, among others. The input 225 (also referred to as the text input 225) can include one or more parameters used to define the generation of messages to be presented to the administrator 205, such as audiences 215A-N or domain identifiers 220A-N.

The application 120 can identify audiences 215A-N (hereinafter generally referred to as the audience(s) 215) indicated in the input 225. The audiences 215 can refer to or include one or more persons or establishments for whom the content item 180 is intended. For example, the audience 215 can include a grouping of patients with similar demographics, such as patients suffering from similar conditions, with similar message preferences, condition severity levels, or medication prescriptions, among others. For example, the audience 215 can include a grouping of subject matter experts in a similar field of study, similar educational backgrounds, or similar localities, among others. For example, the audience 215 can include an entity, such as a governmental organization, educational institution, or non-profit organization.

The application 120 can identify domain identifiers 220A-N (hereinafter generally referred to as the domain identifiers 220) indicated in the input 225. The domain identifiers 220 can correspond to or indicate one or more domains of the input 225. The domains can correspond to an intent of generating the content item 180. The domains can correspond to one or more of the generative transformer models 165. For example, a generative transformer model 165A may correspond to a first domain such that the generative transformer model 165A utilizes, is trained on, or otherwise generates the content item 180 based on the domain. The domain can include a library of words, phrases, or rules for generating the content item 180, such as generating the content item 180 for information for a particular digital therapeutics treatment. The domains can include domains such as an audience experience domain, a regulatory domain, a compliance domain, a science or medical domain, or a product domain, among others.

The domain identifiers 220 can correspond to domains with which to test the content items 180 for risk, such as a science or medical domain (e.g., criteria related to science research or medical literature, such as whether information is medically or scientifically accurate, clinically and statistically relevant, presented in a scientifically balanced manner), a regulatory domain (e.g., criteria related to regulatory guidance, such as not claiming safety or efficacy before a product has been cleared or approved by a regulatory agency), an audience experience domain (e.g., criteria related to user experience, such as clear and understandable instructions, easily accessible technical support, more engaging reward system), a compliance domain (e.g., criteria related to compliance requirements), a product domain (e.g., criteria related to product requirements, such as inclusion of certain features within scope of the project), a commercial domain (e.g., criteria related to commercial launch requirements), or a marketing domain (e.g., criteria related to marketing products), among others. The domains may be derived from end user behavior, end user preferences, or profile information for a given audience 215, among others. The domains may be identified by end user profiles 170 associated with the audience 215. For example, the audience 215 may include the end user profiles 170 related to a condition such as chronic pain, skin pathology, cognitive impairment, mental health conditions, or substance use disorder, among others.

In some embodiments, a profile of the administrator 205 may indicate a domain. For example, the settings (or profile) of the administrator 205 may indicate that the administrator 205 is a product manager and the application may thereby identify a product domain for the input 225. In some embodiments, the application 120 can include preferences as selected by the administrator 205 or determined from a settings of the administrator 205 to identify the domain. In some embodiments, the administrator 205 may identify the domain through the interaction 210. For example, the administrator 205 may select a domain from a drop-down list of domains or may provide text indicating the domain with the interaction 210.

In some embodiments, the science or medical domain can define selection of a content item 180 to an end user suffering from a particular condition. In some embodiments, the medical domain can define the appropriate psychoeducation lesson for a particular medical condition, the appropriate activity for an end user to engage as part of treatment for a particular medical condition, or the text to satisfy a specific reading level for a particular patient subpopulation for generation of the content items 180. In some embodiments, the medical domain can define a template for the content item 180, such as a format for a research paper or journal publication, among others. In some embodiments, the audience experience domain may include end user preferences derived from profile information in the end user profile 170. The end user preferences may correspond to types of messages preferred by an end user as identified in the end user profile 170 of end users corresponding to the audience 215. The profile information may include other data points about the end user, such as a progress of treatment, a difficulty level, a stage on the path to achieving an endpoint, or end user behavior, among others. The end user behavior may include, for example, a type of activities performed by an end user as identified in the end user profile 170.

In some embodiments, the product domain may include the criteria for the user experience for a particular audience. The marketing domain may define a library of marketing phrases for generation of the content items 180. In some embodiments, the marketing domain can define a template for the content item 180, such as a product release statement, a product advisory, press releases, or marketing materials for a product. In some embodiments, the regulatory domain may define the regulatory guidance for establishing and recruiting for clinical trials to provide a variety of circumstances for the generative transformer model 165 to generate a desired content item 180 (e.g., a promotional material may not make reference to a device being safe or effective before it is cleared or approved by a regulatory agency). In some embodiments, the regulatory domain can provide a template or listing of content items 180 related to submissions to regulatory agencies, clinical trial protocols, press releases, or recall statements, among others.

The content handler 140 executing on the data processing system 105 can retrieve, obtain, or otherwise receive the input 225 from the end user device 110. The content handler 140 can perform any of the functions of the application 120 in generating the input 225. In some embodiments, the content handler 140 may retrieve information from one or more end user profiles 170 to generate the input 225. In some embodiments, the content handler 140 may identify the profile corresponding to the administrator 205 by the input 225. The content handler 140 may also identify the identifier (e.g., name), information on sessions conducted by the administrator 205, activity log, message preferences, among others. The content handler 140 may identify the parameters of the input 225. For example, the content handler may identify the audience 215 or the domain identifiers 220 of the input 225.

In some embodiments, upon receipt of the input 225, the risk evaluator 150 may determine a risk score 235 of the input 225. The risk evaluator 150 can determine the input 225 based on at least the parameters of the input 225, such as the audience 215 or the domain identifiers 220 of the input 225. The risk evaluator 150 may apply the one or more risk models 185 to the input 225 (or a prompt derived from the input 220) to generate the risk score 235 for the input 225. In applying one or more risk models 185 to the input, the risk evaluator 150 may generate a risk score 235 for the input.

Applying the risk models 185 to the input 225 can include selecting one or more risk models 185. The risk evaluator 150 may select the one or more risk models 185 to apply to the input 225 based on the parameters of the input 225. For example, the risk evaluator 150 may select a first risk model 185A for a domain identifier 220 corresponding to a medical domain and a second risk model 185B for a domain identifier 220 corresponding to a product domain. In some embodiments, the parameters of the input 225 can identify or include one or more domain identifiers 220 or audiences 215. The risk evaluator 150 can select one or more risk models 185 which corresponds to each of the parameters identified in the input 225.

Applying the risk models 185 can include providing the input 225 as input to the one or more selected risk models 185. Providing the input 225 can include the risk evaluator 150 applying one or more parameters of the input 225. For example, the risk evaluator 150 may provide as input the domain identifiers 220 of the input 225, the audiences 215 of the input 225, other parameters of the input 225, or a combination thereof. In some embodiments, the risk evaluator 150 may provide a first parameter of the input 225 to a first risk model 185A and a second parameter of the input 225 to a second risk model 185B. For example, the risk evaluator 150 may apply different, the same, or overlapping risk models 185 to each of the parameters (e.g., audiences 215, domain identifiers 220, format type of the content items, etc.). In this manner, one or more risk scores 235 can be generated for each of the parameters of the input 225.

The risk score 235 generated by the risk evaluator 150 based on the input 225 can be a number, score, level, or other identifier which indicates a likelihood of the input 225 to correspond to generating a desired content item 180. In some embodiments, a lower risk score can indicate a higher likelihood that the content item 180 generated based on the input 225 corresponds to the desired audience 215, domain, format type, or other parameter of the input 225. In some embodiments, a lower risk score can indicate a higher likelihood that the content item 180 generated based on the input 225 reaches a threshold compliance with a regulation or accuracy, such as accuracy of data, information, citations, or other facts contained within the content item 180. In some embodiments, a lower risk score can indicate a higher likelihood that the content item 180 generated based on the input 225 reaches a threshold relevancy, such as relevance for the audience 215 or adherence to end user or administrator preferences. For example, the relevancy can relate to information in the end user profiles 170, such as a condition suffered by an end user or the audience 215, a preference of the administrator 205 for a type of content item 180, among others. In some embodiments, a lower risk score can indicate a higher likelihood that the input 225 does not contain a subset of words or phrases, or that the input 225 will not generate content items 180 containing the subset of words or phrases.

The content handler 140 may generate a prompt 230 based on the input 225 including the audiences 215 and the domain identifiers 220. In some embodiments, the content handler 140 can generate the prompt 230 responsive to the risk score 235 satisfying a threshold. For example, if the risk score 235 is below a threshold risk score, the content handler 140 may generate the prompt 230. In some embodiments, when the risk score 235 is at or above a threshold risk score, the content handler 140 may not generate the prompt 230 to generate the content items 180. The content handler 140 may provide, for presentation on the user interface 125, an indication that the risk score 235 is at or above a threshold risk level. For example, the content handler 140 may generate a presentation to display which identifies the risk score 235. The indication may include an identification of the risk score 235 for each parameter of the input 225, an overall risk score 235 for the input 225, among others.

The content handler 140 may generate the prompt based on information identified from the profile of the administrator 205, such as previous sessions to generate or modify content items by the administrator 205, a profession of the administrator 205, a preferred content item of the administrator 205, a domain associated with or selected by the administrator 205, among others. The content handler 140 may generate the prompt 230 based on strings within the input 225. For example, the text input 225 may indicate or include words, phrases, or strings identifying parameters for the content items 180 to be generated. The qualities can include the audience 215, the domain identifiers 220, a file type of the content items 180, a format type (e.g., journal article, image, animation, clinical trial protocols, etc.), or a size of the content item (e.g., in file size, word count, page count), among others. The content handler 140 may generate the prompt based on information identified from end user profiles 170 corresponding to the audience 215, such as the endpoint towards which to achieve for the audience 215 to address the condition, the condition to be addressed, the activity log, end user trait, end user identifier, message preferences, information on sessions conducted by the end user, and the progress in addressing the condition, among others.

The content handler 140 may write, produce, or otherwise generate the at least one prompt 230 using the information from the end user profile and the one or more parameters. In generating, the content handler 140 may add, insert, or otherwise include the information from the end user profile 170 and the one or more parameters into a template for generating the prompts. The template may include a set of defined strings and one or more placeholders to be inserted among the strings for input to the generative transformer model 165. The strings may correspond to predefined, fixed text to be included as part of the input prompt for the generative transformer model 165. By traversing through the template and inserting data, the content handler 140 may form and construct the prompt 230.

Figure 3:
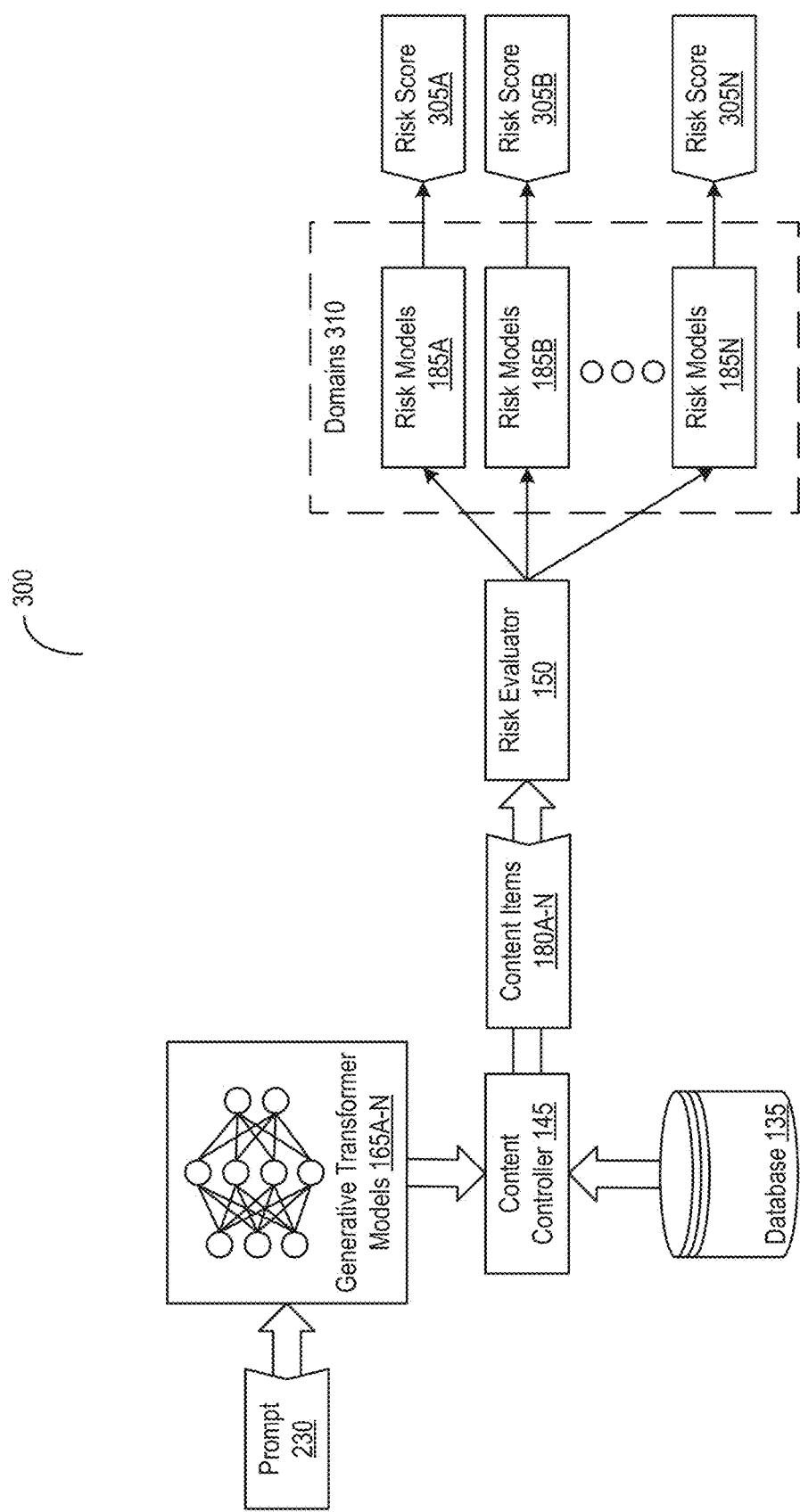
FIG. 3 depicts a block diagram for a process to select one or more models to apply to determine risk scores in the system for generating and regulating content for targeted messages in accordance with an illustrative embodiment.

Referring now to FIG. 3, depicted is a block diagram for a process 300 to select one or more risk models 185 to apply to determine risk scores 305A-N in the system 100 for generating and regulating content for targeted messages. The process 300 may include or correspond to operations performed in the system 100 to generate and regulate content items 180 for targeted messages. Under the process 300, the content controller 145 may identify one or more content items 180. The risk evaluator 150 executing on the data processing system 105 may identify one or more risk models 185 based on a domain 220 of the content items 180. The risk evaluator 150 may apply the models 185 to the content items 180 to determine one or more risk scores 305A-N of the content items 180.

With the generation of the prompt 230, the content handler 140 may feed or apply the prompt 230 to the generative transformer model 165. In applying, the content handler 140 can process the prompt 230 using the set of layers in the generative transformer model 165. As discussed above, the generative transformer model 165 may include the tokenization layer, the input embedding layer, the position encoder, the encoder stack, the decoder stack, and the output layer, among others. The content handler 140 may process the prompt 230 using the tokenizer layer of the generative transformer model 165 to generate a set of word vectors (sometimes herein referred to as word tokens or tokens) for the input set. Each word vector may be a vector representation of at least a portion of the prompt 230 in an n-dimensional feature space (e.g., using a word embedding table). The content handler 140 may apply the set of word vectors to the input embedding layer to generate a corresponding set of embeddings.

With the processing, the content handler 140 may calculate a probability for each embedding. The probability may represent a likelihood of occurrence for an output, given an input token. Based on the probabilities, the content handler 140 may select an output token (e.g., at least a portion of output text, image, audio, video, or multimedia content with the highest probability) to form, produce, or otherwise generate at least a portion the content items 180. The content items 180 output by the generative transformer model 165 can include text content, image content, audio content, video, or multimedia content, among others, or any combination thereof.

In some embodiments, the content items 180 produced by the generative transformer models 165 can contain text content, image content, audio content, video, or multimedia content, among others, or any combination thereof. For example, the presentation of the content items 180 may include an image of a smiley face to further encourage a user to complete their goals. Furthermore, the content items 180 may include a video clip of a loved one, a motivational speaker, a medical professional, an influencer, or a therapist, among others, or any combination thereof.

The content controller 145 may identify the content items 180 for providing to the administrator 205 via the application 120 operating on the administrator device 190. Identifying the content items 180 can include retrieving, receiving, or otherwise obtaining the content items 180 from one or more sources, such as from the generative transformer models 165 or the database 135. The content controller 145 may identify the content items 180 within the database 135 which correspond to the input 225. For example, the content controller 145 can identify previously generated, created, or uploaded content items 180 stored within the database 135.

The content controller 145 may determine that the stored content items 180 correspond to the input 225 provided by the administrator 205. The content controller 145 may identify strings within the input 225 or parameters of the input 225 which relate to, correspond to, or are associated with the stored content items 180. For example, the input 225 may indicate an audience 215A also identified in the stored content item 180A. The content controller 145 may determine that one or more strings of the input 225 match or are similar to one or more strings of the content item 180 stored in the database 135. In this manner, the content controller 145 can identify the content items 180 which correspond to the input 225 within the database 135 and can retrieve one or more content items 180 previously generated and stored on the database 135.

The content controller 145 may prevent the content handler 140 from generating the prompt 230 responsive to a determination that one or more content items 180 in the database 135 correspond to the input 225. In some embodiments, the content controller 145 may access the database 135 to determine if one or more content items 180 in the database 135 correspond to the input 225 prior to the generation of the prompt 230 by the content handler 140, or prior to providing the generated prompt 230 to the generative transformer models 165. The content controller 145 may instruct the content handler 140 to refrain from generating the prompt 230 or to refrain from providing the generated prompt 230 to the generative transformer model 165. In some embodiments, the content controller 145 may prevent the content handler 140 from providing the generated prompt 230 to the generative transformer models 165 responsive to identifying one or more corresponding content items 180 within the database 135.

The content controller 145 may determine that no previously generated content items 180 are stored on the database corresponding to the input 225. The content controller 145 may access the database 135 and determine that no previously generated content items 180 corresponding to the input 225 are stored in the database 135. In some embodiments, the content controller 145 may access the database 135 to make the determination prior to the generation of the prompt 230 by the content handler 140 or prior to the content handler 140 providing the generated prompt to the generative transformer models 165 to generate the content items 180. The content controller 145 may invoke, responsive to determining that no previously generated content items 180 are stored in the database 135, the generative transformer model 165 to generate the content items 180 using the prompt 230 created based on the input 225. Invoking the generative transformer models 165 can include the content controller 145 providing an instruction to the content handler 140 to generate the prompt 230 or to provide the generated prompt 230 to the generative transformer models 165 to generate the content items 180.

The content controller 145 may rank the identified content items 180 according to one or more criteria. The content controller 145 may rank the identified content items 180 upon identifying the content items 180, or the content controller 145 may rank the identified content items 180 prior to provision of the content items 180 to the administrator device 190. The one or more criteria used by the content controller 145 to rank the content items 180 can include feedback from the audience 215 to prior digital therapeutic content. For example, the data processing system 105 may receive feedback by the audience 215 regarding content items previously presented to the audience 215. The content controller 145 may rank the generated content items 180 based on feedback from the audience 215. The feedback may include numerical rating of the content item 180, textual feedback describing an opinion of the content item 180, or a binary indicator of the content item (such as a "thumbs up" or "thumbs down").

The content controller 145 may rank the generated content items 180 based on criteria including an audience preference for prior digital therapeutic content. For example, the audience may indicate preferred types of content items 180, such as a preferred format (video, text, audio), preferred duration for presentation of content items 180, preferred styles of the content items 180 (color, font type, paragraph formatting, etc.), among others. The criteria used by the content controller 145 to rank the content items 180 can include audience behavior in response to prior digital therapeutic content. For example, end user profiles 170 indicated or included in the audience 215 may indicate one or more content items 180 or types of content items 180 which elicited higher response, engagement, or adherence from the audience 215 participating in a digital therapeutics regimen.

The content controller 145 may rank the content items 180 based on a reading level of the content items 180. For example, the content controller 145 may determine a reading level for each of the identified content items 180 and may rank the content items 180 according to the reading level. The reading level can refer to an age, amount of education, or literacy level to read or comprehend a passage of text, such as a text-based content item 180. In some embodiments, the content controller 145 may rank the content items 180 based on an association of the reading level of the content items 180 with a reading level indicated by the audience 215. For example, the content controller 145 may rank a content item 180A more highly or favorably than a content item 180B if the content item 180A includes the same or a similar reading level as the audience 215.

The one or more criteria may include an identification of the corresponding model used to generate the content item 180. For example, each content item 180 may be generated by a respective generative transformer model 165. The content controller 145 may rank the content items 180 generated by the generative transformer models 165 according to which generative transformer model 165 generated the respective content item 180. In some embodiments, a content item 180A generated by a generative transformer model 165A maintained, trained, or associated with the data processing system 105 may elicit a higher or more favorable ranking than a content item 180B generated by a generative transformer model 165B not maintained or trained by the data processing system 105.

The risk evaluator 150 may select, choose, or identify the risk models 185 from the database 135 to apply to the identified content items 180. The risk evaluator 150 may identify the risk models 185 responsive to the receipt of the input 225 from the application operating on the administrator device 190. The risk evaluator 150 may retrieve the risk models 185 responsive to generation of the prompt 230 by the content handler 140. The risk evaluator 150 may access the database 135 to retrieve the risk models 185 at any time to apply to the identified content items 180.

The risk evaluator 150 may select the models 185 based on the one or more domains 310 associated with the input 225. The risk evaluator 150 may identify one or more domains 310 associated with the input 225 based on the domain identifiers 220 of the input 225. In some embodiments, one or more risk models of the risk models 185 may correspond to a particular domain of the domains 310. For example, a first risk model 185A may correspond to a medical domain, and a second risk model 185B may correspond to an audience experience domain. The risk evaluator 150 may select one or more risk models 185 that correspond to the domains 310 of the input 225. Corresponding to the input 225 can refer to a domain identifier 220 of the input 225 matching a domain for which the one or more risk models 185 are trained. The one or more risk models 185 may be trained for one or more particular domains 310 by having a training set provided to the one or more risk models 185 trained for the particular domain including verbiage, phrasing, or content items of the particular domain.

The risk evaluator 150 may select multiple models 185 corresponding to one or more domains 310. In some embodiments, the input 225 may identify multiple domains 310. For example, the input 225 may identify multiple domains 310 such as a product domain, a medical domain, and a regulatory domain. The risk evaluator 150 may select a risk model 185 corresponding to each of the domains 310 identified in the input 225. For example, for an input 225 identifying a product domain, a medical domain, and a regulatory domain, the risk evaluator 150 may identify a first risk model 185A corresponding to a product domain, a second risk model 185B corresponding to a medical domain, and a third risk model 185C corresponding to a regulatory domain. In some embodiments, a risk model 185 can correspond to multiple domains. For example, a risk model 185A can correspond to a medical domain and a science domain. The risk evaluator 150 may select a risk model 185 which corresponds to one or more of the domains identified by the domain identifiers 220 of the input 225.

The risk evaluator 150 may apply the selected risk models 185 to the identified content items 180 to generate one or more risk scores 305A-N (hereinafter generally referred to as the risk score(s) 305). In some embodiments, applying the risk models 185 to the content items 180 can include the risk evaluator 150 providing the identified content items 180 as input to the models 185 to generate the risk score 305 associated with each content item. In some embodiments, a subset of the content items 180 can be applied to a risk model 185. For example, a content item generated by a first generative transformer model 165A may not be provided to a first risk model 185A. In this manner, content items 180 generated by a generative transformer model 165 maintained or trained by the data processing system 105 may not be subject to one or more of the risk models 185.

The risk evaluator 150 may provide the content items 180 to multiple risk models 185 corresponding to each domain identifier 220 of the input 225 to generate respective risk scores 305 from each risk model 185 applied to the content items 180. In some embodiments, the risk evaluator 150 can generate a risk score 305 for each domain 310 associated with the input 225. The risk score 305 can be a score identifying a level of risk associated with a content item 180 or the input 225. In some embodiments, the risk score 305 can define the level of risk with respect to the domain 310. The risk score 305 can be like or include the risk score 235.

The risk score 305 can be used to determine whether the content item 180 is permitted or restricted to be provided to the audience 215 (e.g., directly or through the administrator 205 via the application 120 operating the administrator device 190). In some embodiments, a first risk score 305A lower, smaller, or less than a second risk score 305B can indicate that the first risk score is more likely to be suitable for provision. In general, a lower risk score 305 can indicate a higher likelihood that the content item 180 generated based on the input 225 corresponds to the desired audience 215, domain, format type, or other parameter of the input 225. Generating the risk scores 305 can include the risk evaluator 150 applying the risk models 185 to determine to what degree each content item 180 complies with a domain 310.

Using the risk model 185, the risk evaluator 150 may determine the risk score 305 to indicate a degree that the information of the generated content items 180 satisfies a criteria for the domain 310 associated with the risk model 185. For example, the risk score 305 may indicate a degree of compliance or satisfaction of the phrases, words, or portions with the criteria for a particular domain 310 associated with the risk model 185. For example, the regulatory domain may specify that inclusion of "will" or "is" in relation to efficacy is to be avoided. If the content contains such claims (e.g., "this product will improve your condition"), the corresponding risk model 185 may output that a high risk score 305 indicating that the criteria of the regulatory domain is not satisfied.

The risk score 305 can correspond to a compliance or non-compliance of the content items 180 with criteria set for a particular domain. A compliance of the content items 180 can refer to the content items 180 being suitable for provision. Suitable for provision can include the content items 180 being above a threshold correspondence to the parameters identified in the input 225, such as the domain or the audience 215. In some embodiments, a risk score 305 lower than a threshold risk score can indicate that a content item 180 corresponding to the risk score 305 is compliant. In some embodiments, a risk score 305 greater than or equal to a threshold risk score can indicate that a content item 180 corresponding to the risk score 305 is not compliant.

Figure 4:
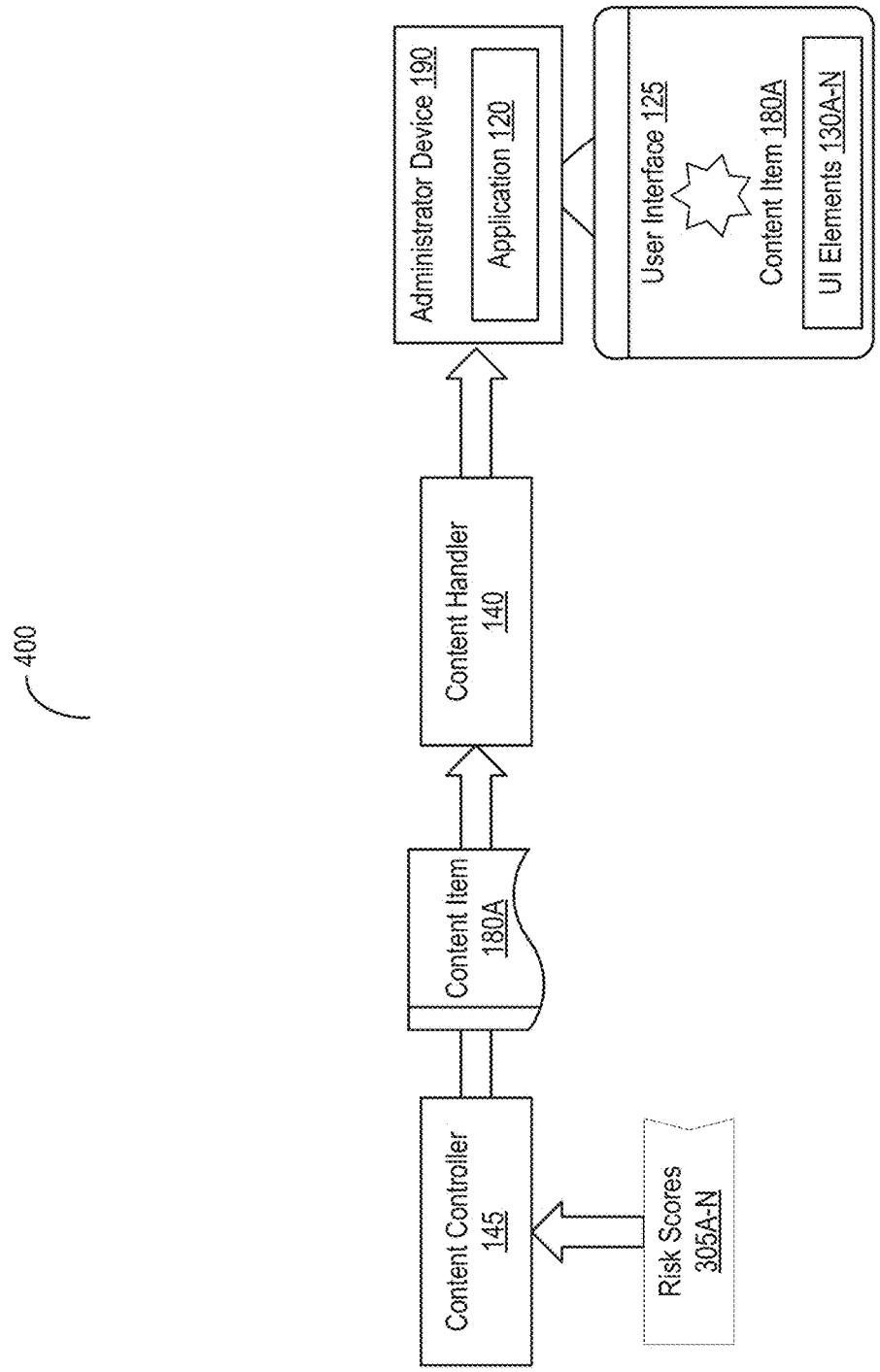
FIG. 4 depicts a block diagram for a process to select a content item to transmit in a message to an administrator device in the system for generating and regulating targeted messages in accordance with an illustrative embodiment.

Referring now to FIG. 4, depicted is a block diagram for a process 400 to select a content item 180A to transmit in a message to the administrator device 190 in the system 100 for generating and regulating content for targeted messages. The process 400 may include or correspond to operations performed in the system 100 to generate and regulate the content items 180 for targeted messages. Under the process 400, the content controller 145 executing on the data processing system 105 may select one or more content items 180 based on their corresponding risk scores 305. The content controller 145 may provide the one or more content items 180 to the content handler 140 to provide to the administrator device 190.

The content controller 145 may select one or more content items 180A based on the risk score 305 associated with the content items 180A. Upon generation of the risk scores 305 by the risk evaluator 150, the content controller 145 may select one or more content items 180A based on their respective risk scores. In some embodiments, the content controller 145 may select the content items 180A with the lowest risk score. The content controller 145 may select one or more content items 180A with a risk score below a threshold risk score, or the content controller 145 may select a content item 180A or set of content items 180A with the lowest risk score. In some cases, the content controller 145 may select one or more content items 180A with a risk score at or above the threshold risk score or a set of the content items 180A with the highest risk score. The highest or lowest risk scores 305 can be determined as the greatest or least risk scores 305, respectively, of the set of risk scores 305 generated by the risk evaluator 150 for the input 225.

The content controller 145 may select the content items 180A based on a ranking of the content items by the content controller 145. As described herein, the content controller 145 may rank the content items 180 based on a variety of criteria, including, but not limited to, feedback from the audience to prior digital therapeutic content, audience preference for prior digital therapeutic content, an identification of the corresponding generative transformer model 165 used to generate the content item 180, or audience behavior in response to prior digital therapeutic content, among others. The content controller 145 may select the content items 180A with the most favorable or highest ranking by the content controller 145. In some embodiments, the content controller 145 may select the content items 180A based on a highest ranked content item 180A of the set of content items possessing a risk score below the threshold risk score. For example, the content controller 145 may select the content items 180A with the highest likelihood of increasing audience adherence to a digital therapy regimen that also possesses a risk score 305 below the threshold risk score.

The content handler 140 may provide the selected content item 180A to the administrator device 190. The content handler 140 may provide the selected content item 180A in a message transmitted to the administrator device 190. The message may include an instruction for presentation of the content item 180A on the user interface 125 by the application 120 operating on the administrator device 190. The user interface 125 may present the content item 180A according to the instruction in the message.

To transmit, the content handler 140 may generate at least one instruction for presenting the content items 180A to transmit to the administrator device 190. The instruction can include an identifier for the message or the content items 180A. In some embodiments, the instruction may be code, data packets, or a control to present a message to the administrator 205. The instruction may include processing instructions for display of the message on the application 120 through the UI elements 130 of the user interface 125. The instruction may also include instructions for the administrator 205 to perform in relation to their session to generate and modify content items. For example, the instruction may display the message including the content items 180A instructing the end user to perform a certain activity associated with their session. In some embodiments, the instructions may be in accordance with a messaging protocol, such as a short message service (SMS) or a multimedia messaging service (MMS). The instruction may identify the administrator device 190 (e.g., using a phone number or network address) to which to transmit the message, as well as the content items 180A of the message in a payload. Upon generation, the content handler 140 can send the instruction to the administrator device 190 via the network 115.

Upon receipt, the administrator device 190 can render, display, or otherwise present the message via a display, such as the user interface 125. In some embodiments, the application 120 on the administrator device 190 may render, display, or otherwise present the message via the user interface 125. For example, the instructions for the message may specify, identify, or define a layout (e.g., positioning, size, and color) for individual UI elements 130 when the message is presented via the user interface 125 of the application 120. In some embodiments, the application 120 on the administrator device 190 may provide a sandbox environment to simulate presentation of the message to the end user. For example, when the message is delivered in accordance with a messaging protocol (e.g., SMS and MMS), the application 120 on the administrator device 190 may present a messaging application to mimic various SMS messaging applications to present the message.

In some embodiments, the message can include information related to the risk scores 305 of the content items 180. For example, the message can identify the risk score 305 associated with each content item 180. The message can indicate whether a content item 180B corresponds to a risk score 305B which satisfies the risk threshold. The application 120 can display a listing, table, or other presentation of the risk scores 305 associated with their respective content items. In some embodiments, the application 120 can display a listing, mapping, or other presentation depicting the generative transformer model 165 associated with each content item 180. For example, the application can display an associated risk score 305B and an associated generative transformer model 165B for a content item 180B. The application 120 can display, via the user interface 125, the information related to the risk scores 305. For example, the application 120 may display, according to the instruction, a mapping between any of the content items 180 and their respective risk scores 305, generative transformer models 165, or domains 310, among others.

In some embodiments, the message can include information related to the risk scores 235 corresponding to the input 225. The message can include an indication that the risk score 235 corresponding to the input 225 exceeds a threshold risk score. For example, the indication can include that a risk score 235 associated with the input 225 exceeds a threshold risk score. The application 120 can display the indication as a listing, table, or other presentation using the UI elements 130 of the user interface 125. In some embodiments, the application 120 can display a listing, mapping, or other presentation depicting the parameters associated with the input 225. For example, the application can display an associated risk score 235, an associated domain identifier 220, or an associated audience 215, among others, with the input 225 as the indication.

Figure 5A:
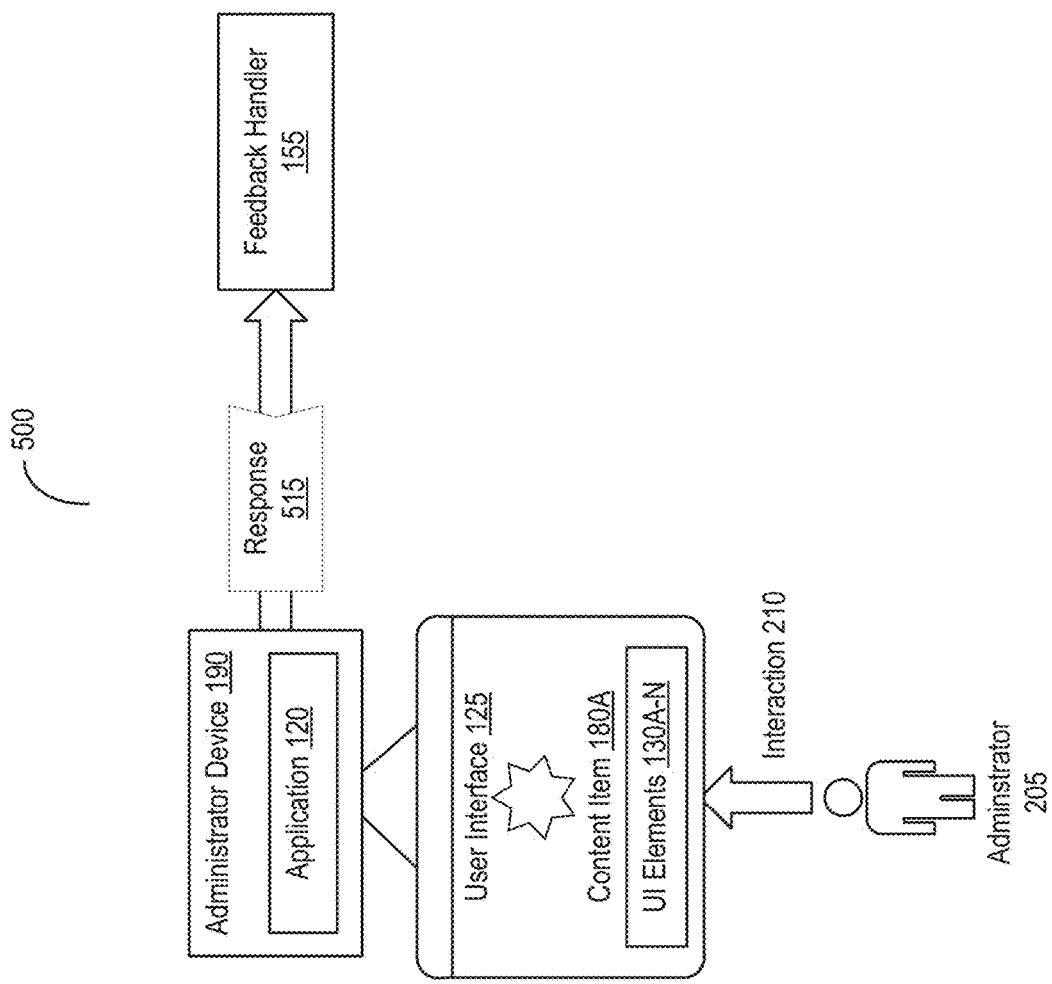
FIG. 5A-C depict block diagrams for a process to update generative transformer models in the system for regulating and generating content for targeted messages in accordance with an illustrative embodiment.
Figure 5B:
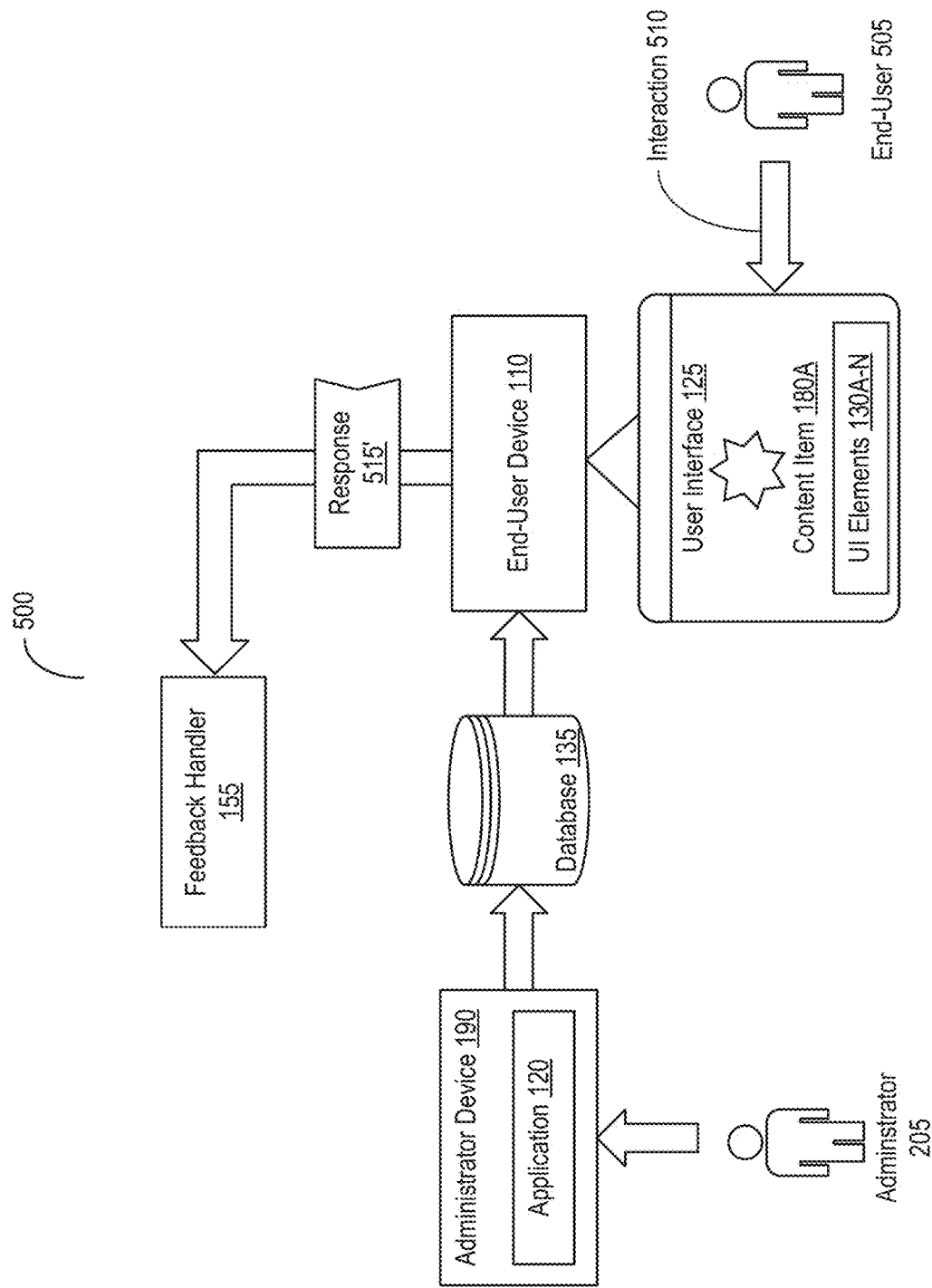
Figure 5C:
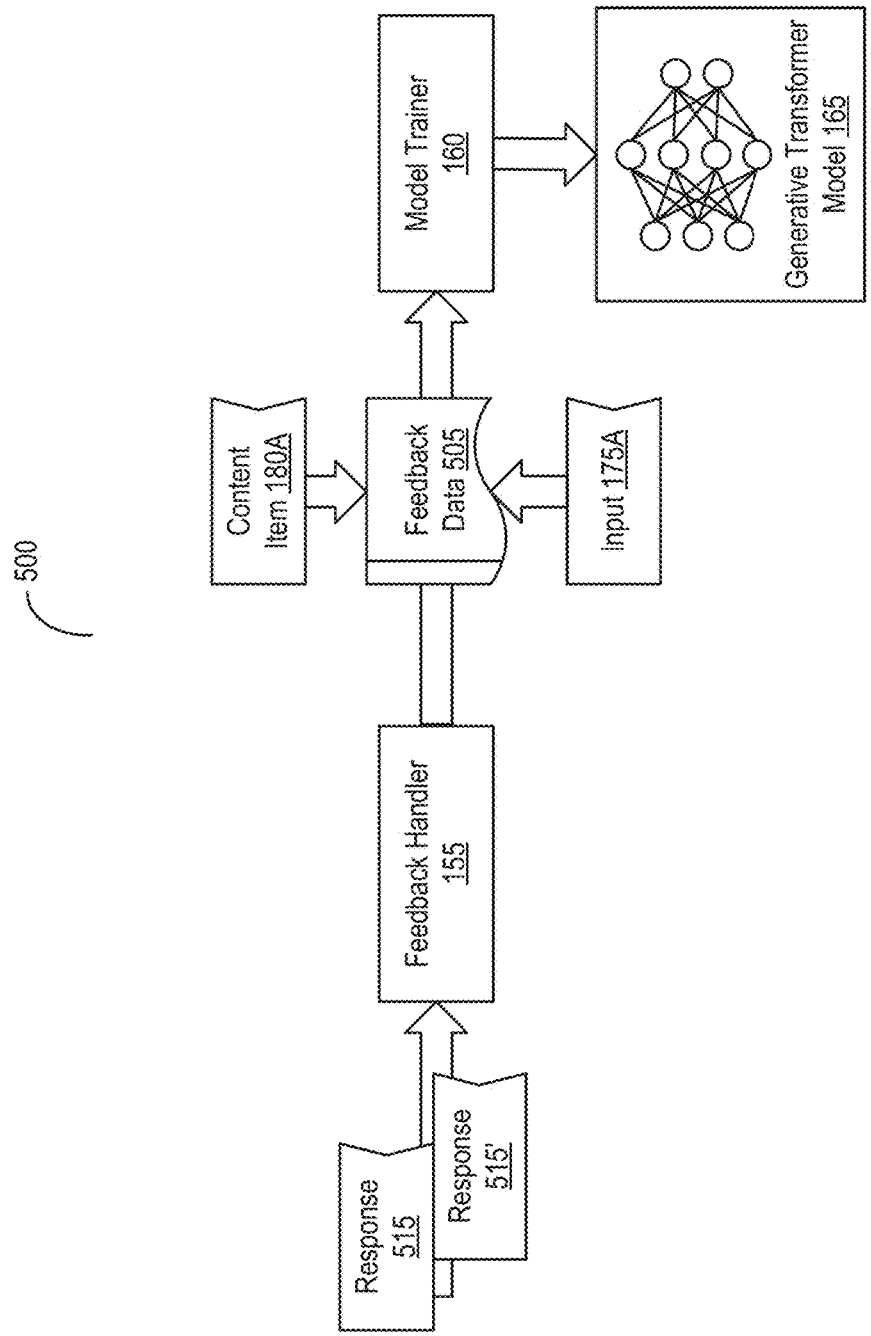

Referring now to FIGS. 5A-C, depicted are block diagrams for a process 500 to update generative transformer models in the system 100 for regulating and generating content for targeted messages. The process 500 may include or correspond to operations performed in the system 100 to generate and regulate content items 180 for targeted messages. Under the process 500, the application 120 on the administrator device 190 can receive the interaction 210 from the administrator 205. The feedback handler 155 can receive a response 515 generated from the administrator device 190. The feedback handler 155 can receive a response 515' generated from a presentation of a content item on the end user device 110. The feedback handler 155 can provide feedback data 505 based on the responses to the model trainer 160 to train the generative transformer model 165.

Referring now to FIG. 5A, with the presentation of the content item 180A to the administrator 205, the administrator device 190 may monitor for at least one interaction 210 by the administrator 205 in response to the presentation of the message including at least one of the content items 180A or the information related to the risk scores 305 or 235. The interaction 210 may include data (e.g., text) inputted by the administrator 205 in response to the message. In some embodiments, the interaction 210 may include data which identifies one or more portions of the content item 180A to be maintained or modified. For example, the administrator 205 may indicate, through the interaction 210, a selection of one or more portions of the content items 180A through the UI elements 130. The one or more portions may correspond to portions of the content item 180A to be modified. In some embodiments, the administrator 205 can provide modifications to the portions of the content items 180A by the interaction 210 with the UI elements 130. For example, the administrator 205 can edit text (e.g., delete, add, format) of the content items 180A, edit colors or styles of the content items 180A, or edit other presentations of the content items 180A on the user interface 125 by providing the interaction 210.

Upon detection of the interaction 210, the administrator device 190 may output, produce, or generate at least one administrator response 515 for transmission to the data processing system 105. The administrator response 515 may indicate, include, or otherwise identify the portions of the content items 180A to be maintained or modified. For example, the administrator response 515 can include an association of the content item 180A to be modified with the one or more portions of the content item 180A to be modified. The administrator response 515 can include a time for the response 515.

Referring now to FIG. 5B, an end user 505 may provide an interaction 510 to a presented content item. In some embodiments, the content item 180A may be presented to an end user 505 on the end user device 110. Upon an approval from the administrator 205, the content item 180A may be stored in the database 135 for provisioning to the end user 505. In some implementations, the end user device 110 can access the database 135 to retrieve, obtain, or access the content item 180A stored thereon. The end user device 110 may present the content item 180A to the end user 505 via the user interface 125 operating on the end user device 110. The end user device 110 may present the content item 180A as a part of a digital therapeutics session to address a condition of the end user 505, as a public text such as a publication or journal article, or as an advertisement on a web-browser or other application operating on the end user device 110, among others.

The end user device 110 may monitor for an interaction 510 with the content item 180A on the user interface 125. The interaction 510 can include some of the functionalities of the interaction 210 by the administrator 205. For example, the interaction 510 may be concurrent with the presentation of a message including the content item 180A. For example, the interaction 510 may correspond to an interaction of playing a video clip included in the message through a play button presenting through an application operating on the end user device 110. In some embodiments, the interaction 510 may be subsequent to the presentation of the message on the end user device 110. For instance, the interaction 510 may correspond to a set of interactions to log end user feedback related to the content items 180A within the message, after presentation of the message to the end user.

The interaction 510 may also include data (e.g., text) inputted by the end user 505 in response to the message. In some embodiments, the interaction 510 may include data which identifies one or more portions of the content item 180A to be modified. For example, the end user 505 may indicate, through the interaction 510, a selection of one or more content items 180A presented to the end user 505. The end user 505 may be prompted to provide feedback based on the content item 180A, such as whether the end user 505 enjoyed the content or participated in an activity indicated by the content. In some cases, the end user device 110 may monitor for the interaction 510 with one or more of the UI elements 130. For example, the end user device 110 may monitor for a time between the presentation of the message including the content item 180A and the interaction 510, an adherence to a therapeutic regimen upon presentation of the content item 180A, or subsequent activities performed by the end user 505 in relation to the presentation of the content item 180A.

Upon detection of the interaction 510, the end user device 110 may output, produce, or generate at least one end user response 515' for transmission to the data processing system 105. The end user response 515' may indicate, include, or otherwise identify UI elements 130 indicated in the end user interaction 510 to presentation of the message. The end user response 515' may include a time for the response 515', such as a time between the presentation of the message including the content item 180A and the receipt of the interaction 510. The end user response 515' may indicate other times associated with the presentation of the message including the content item 180A. For example, the end user response 515' can include a reading time for the end user 505 to read the content item 180A.

In some embodiments, an application on the end user device 110 may generate the end user response 515' using the detected interaction 510. The response 515' may identify an event associated with the interaction 510 by the end user 505, a time stamp for the presentation of the message to the end user 505, a time stamp for the event, and an identifier for the end user 505, among other information. The end user response 515' may also include data inputted by the end user 505 via the user interface 125 operating on the end user device 110. In some embodiments, the application operating on the end user device 110 may maintain a timer to keep track of time elapsed since presentation of the message to the end user 505. The application may compare the elapsed time with a time limit for the message. When the elapsed time exceeds the time limit, the application may generate the end user response 515' to indicate no end user interaction with the message. With the generation, the application or the end user device 110 may provide, transmit, or otherwise send the response 515' to the feedback handler 155.

Referring now to FIG. 5C, the feedback handler 155 may, based on the administrator response 515 and the end user response 515', produce, create, or otherwise generate feedback data 505. The feedback data 505 may be used to train the generative transformer models 165. The feedback data 505 may include information derived from the administrator response 515. For example, the feedback data 505 may include identification of one or more portions to be maintained or modified. The feedback data 505 may include information derived from the end user response 515. The feedback data 505 may include an indication of whether the end user interacted with the content item upon presentation.

In some embodiments, the feedback handler 155 may generate the feedback data 505 for subsequent generation of content items by the generative transformer model 165. In some embodiments, the feedback data 505 may identify or include information to be used as one or more parameters defining subsequent content items to be generated and presented for the end user 505. Upon generation, the feedback handler 155 may store and maintain an association between the feedback data 505 and the end user profile 170 on the database 135. The feedback data 505 may indicate the one or more portions to be modified in the content item 180. Upon generation, the feedback handler 155 may store and maintain an association of the one or more portions with the content item 180A in the database 135.

In some embodiments, the feedback handler 155 may generate the feedback data 505 to include information to be used to update weights associated with the generative transformer model 165. The feedback data 505 may be generated to include the content items 180A of the message, the input 225, or the information from the response 515 from the administrator 405. The feedback data 505 generated from the end user response 515 may indicate a degree to which the presented message elicits the interaction from the end user 505. A number or duration of interactions from the end user 505 with the content item 180A can be logged and included within the feedback data 505. Upon generation, the feedback handler 155 may include the end user interaction information and the content items 180A of the message into the feedback data 505.

The model trainer 160 may use the feedback data 505 to modify, adjust, or otherwise update the weights of the generative transformer model 165. The model trainer 160 may identify one or more of the generative transformer models 165 to update based on the feedback data 505. The feedback data 505 may be aggregated over multiple responses 515 from the administrator 205 or from multiple administrators 205. For example, the content item 180A may be subject to multiple rounds of review by various administrators or the same administrator 205. The feedback data 505 may likewise be aggregated over multiple responses 515' from the end user 505 or from multiple end users 505. For example, the content item 180A may be presented to one or more end users 205 on one or more user devices 110 during respective digital therapeutics sessions. Each end user 205 presented the content item 180A may provide an interaction 510 in response to the presentation of the content item 180A.

In general, the model trainer 160 may update the weights to credit production of messages with high performance metrics or low risk scores 305 or 235 and punish outputting messages with lower performance metrics. The training or fine-tuning of the generative transformer model 165 using the feedback data 505 may be similar to the training or fine-tuning of the risk models 185 as described herein. To train, the model trainer 160 may define, select, or otherwise identify at least a portion of each feedback data 505 as training data and at least a portion of each feedback data 505 as testing data. The training data may be used to input into the generative transformer model 165 to produce an output to be compared against the test data. The portions of each feedback data 505 can at least partially overlap and may correspond to a subset of text strings within the feedback data 505.

The model trainer 160 can feed or apply the strings of the training data from the feedback data 505 into the generative transformer model 165. In applying, the model trainer 160 can process the input strings in accordance with the set of layers in the generative transformer model 165. As discussed above, the generative transformer model 165 may include the tokenization layer, the input embedding layer, the position encoder, the encoder stack, the decoder stack, and the output layer, among others. The model trainer 160 may process the input strings (words or phrases in the form of alphanumeric characters) of the training data using the tokenizer layer of the generative transformer model 165 to generate a set of word vectors for the input set. Each word vector may be a vector representation of at least one corresponding string in an n-dimensional feature space (e.g., using a word embedding table). The model trainer 160 may apply the set of word vectors to the input embedding layer to generate a corresponding set of embeddings. The model trainer 160 may identify a position of each string within the set of strings of the source set. With the identification, the model trainer 160 can apply the position encoder to the position of each string to generate a positional encoding for each embedding corresponding to the string and by extension the embedding.

The model trainer 160 may apply the set of embeddings along with the corresponding set of positional encodings generated from the input set of the feedback data 505 to the encoder stack of the generative transformer model 165. In applying, the model trainer 160 may process the set of embeddings along with the corresponding set of positional encodings in accordance with the layers (e.g., the attention layer and the feed-forward layer) in each encoder in the encoder block. From the processing, the model trainer 160 may generate another set of embeddings to feed forward to the encoders in the encoder stack. The model trainer 160 may then feed the output of the encoder stack to the decoder stack.

In conjunction, the model trainer 160 may process the data (e.g., text, image, audio, video, or multimedia content) of the test data using a separate tokenizer layer of the generative transformer model 165 to generate a set of word vectors for the test data. Each word vector may be a vector representation of at least one corresponding string in an n-dimensional feature space (e.g., using a word embedding table). The model trainer 160 may apply the set of word vectors to the input embedding layer to generate a corresponding set of embeddings. The model trainer 160 may identify a position of each string within the set of strings of the target set. With the identification, the model trainer 160 can apply the position encoder to the position of each string to generate a positional encoding for each embedding corresponding to the string and by extension the embedding.

The model trainer 160 may apply the set of embeddings along with the corresponding set of positional encodings generated from the destination set of the feedback data 505 to the decoder stack of the generative transformer model 165. The model trainer 160 may also combine the output of the encoder stack in processing through the decoder stack. In applying, the model trainer 160 may process the set of embeddings along with the corresponding set of positional encodings in accordance with the layers (e.g., the attention layer, the encoder-decoder attention layer, the feed-forward layer) in each decoder in the decoder block. The model trainer 160 may combine the output from the encoder with the input of the encoder-decoder attention layer in the decoder block. From the processing, the model trainer 160 may generate an output set of embeddings to be fed forward to the output layer.

Continuing on, the model trainer 160 may feed the output from the decoder block into the output layer of the generative transformer layer 165. In feeding, the model trainer 160 may process the embeddings from the decoder block in accordance with the linear layer and the activation layer of the output layer. With the processing, the model trainer 160 may calculate a probability for each embedding. The probability may represent a likelihood of occurrence for an output, given an input token. Based on the probabilities, the model trainer 160 may select an output token (e.g., at least a portion of output text, image, audio, video, or multimedia content with the highest probability) to form, produce, or otherwise generate a feedback output. The feedback output can include text content, image content, audio content, video, or multimedia content, among others, or any combination thereof.

With the generation, the model trainer 160 can compare the output from the generative transformer model 165 with the feedback data 505 used to generate the feedback output. The comparison can be between the probabilities (or distribution) of various tokens for the content (e.g., words for text output) from the output versus the probabilities of tokens in the feedback data 505. For instance, the model trainer 160 can determine a difference between a probability distribution of the output versus the feedback data 505 to compare. The probability distribution may identify a probability for each candidate token in the output or the token in the feedback data 505. Based on the comparison, the model trainer 160 can calculate, determine, or otherwise generate a loss metric. The loss metric may indicate a degree of deviation of the output from the expected output as defined by the feedback data 505 used to generate the output. The loss metric may be calculated by in accordance with any number of loss functions, such as a norm loss (e.g., L1 or L2), mean squared error (MSE), a quadratic loss, a cross-entropy loss, and a Huber loss, among others.

Using the loss metric, the model trainer 160 can update one or more weights in the set of layers of the generative transformer model 165. The updating of the weights may be in accordance with back propagation and optimization function (sometimes referred to herein as an objective function) with one or more parameters (e.g., learning rate, momentum, weight decay, and number of iterations). The optimization function may define one or more parameters at which the weights of the generative transformer model 165 are to be updated. The model trainer 160 can iteratively train the generative transformer model 165 until convergence. Upon convergence, the model trainer 160 can store and maintain the set of weights for the set of layers of the generative transformer model 165 for use.

In this manner, the data processing system 105 may iteratively and continuously factor in responses 515 from presentations of content items 180 to the administrator 205 and to the end users 505 to improve generation of messages compliant for a particular domain 310. Furthermore, the data processing system 105 may iteratively and continuously factor in responses 515' from end users 505 to improve generation of new and effective content for subsequent messages within each domain 310. Compared to content generated by generic generative transformer models 165, the incorporation of the feedback data 505 may enable generation of new content items that are more targeted and pertinent to the audience 215, domain 310 and preferences of the end user 505. In the context of digital therapeutics, the new generation of the content items may factor in changes to the use, such as improvement or degradation of the end user's condition or progression through the therapy regimen. With the use of the generative transformer model 165, the content can be generated specifically targeting the end user in a flexible manner and can scale the individualization of content to a large audience. The enablement of flexibility, scalability, and specificity can optimize or reduce consumption of computing resources (e.g., processor and memory) and network bandwidth that would have been otherwise wasted from providing ineffective content. From a human-computer interaction (HCI) perspective, the content generated by leveraging the generative transformer model 165 can yield higher quality of interactions by the end user with the end user device 110. In addition, the increase in engagement can result in higher levels of adherence of the end user with the therapy regimen. The higher adherence in turn may lead to a greater likelihood in preventing, alleviating, or treating conditions of the end user.

Figure 6:
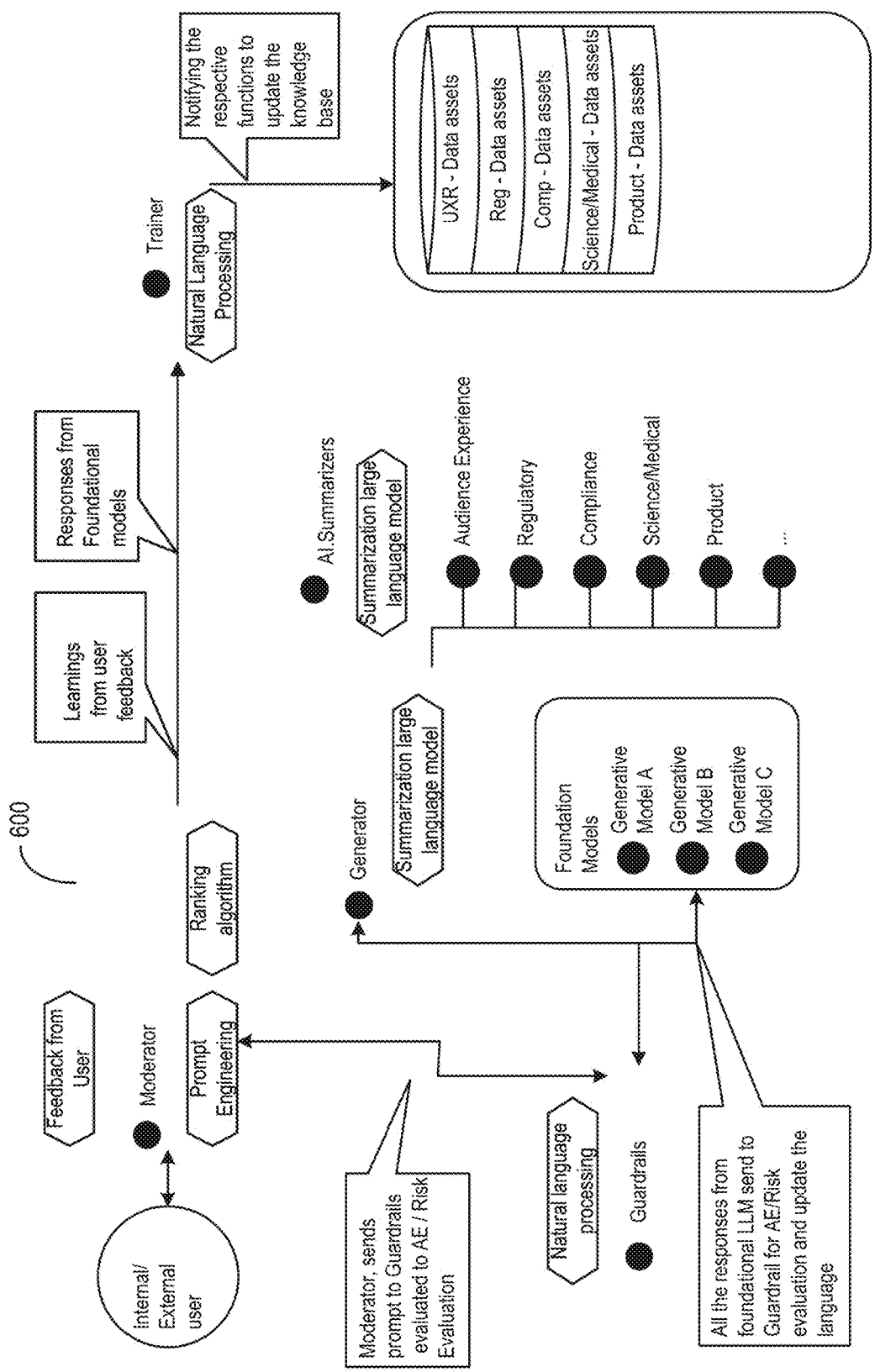
FIG. 6 depicts a block diagram for an architecture of a system for generating content items in the system for regulating and generating content for targeted messages in accordance with an illustrative embodiment.

Referring now to FIG. 6, depicted is a flow diagram for an architecture of a system 600 for generating content items in the system 100 for generating and regulating content for targeted messages. The system 600 may include or correspond to operations performed in the system 100 to generate and regulate content items 180 for targeted messages. The system 600 may include a moderator to accept input from an internal administrator, provide content items from the models or the previously generated content, and receive any feedback from the administrator upon generation and from the end user upon presentation. Upon receipt of an input, the moderator may forward the input to a guardrail. The input may include textual data entered by the administrator to create or search for digital therapeutic content. The guardrail may evaluate a risk of the input using one or more natural language processing (NLP) models and risk models. If the input is determined to be high risk (e.g., a risk score above a threshold), the guardrail may return an indication that the input is of high risk to the moderator for presentation to the administrator. On the other hand, if the input is determined to be low risk (e.g., the risk score below the threshold), the guardrail may pass the input to a generator.

With receipt of the input, the generator may use an NLP technique (e.g., automated summarization) to search for previously generated digital therapeutic content on a database. The database may store and maintain content across multiple domains, such as audience experience, regulatory, compliance, science or medical, and product. In conjunction, the generator may pass the input in the form of a prompt to a set of generative models. Each generative model may be a generative transformer model, and may use the prompt to generate new digital therapeutic content. The generator may aggregate content items found in the database and outputted by the generative models, and provide the content items to the guardrails. The guardrails in turn may evaluate each content item using the risk models. For each content item, the guardrails may determine a risk score indicating a degree of risk or compliance with a particular domain for the risk model. Using the risk scores, the guard rails may select a subset of content items to provide to the moderator.

The moderator may use a ranking algorithm to rank the content items based on other information, such as end user profile information and domain, among others. Based on the ranking, the moderator may select one or more content items to present to the end user. The content items may be presented to the administrator for entry of revisions. The content items may also be provided to the end user to gauge audience response to the information contained therein. The moderator may receive feedback from the end user identifying the audience response or the modifications by the administrator, among others. The moderator may provide the feedback to a trainer, and the trainer in turn may use the data in the feedback to improve the generative models as well as the content items stored and maintained on the database.

Figure 7:
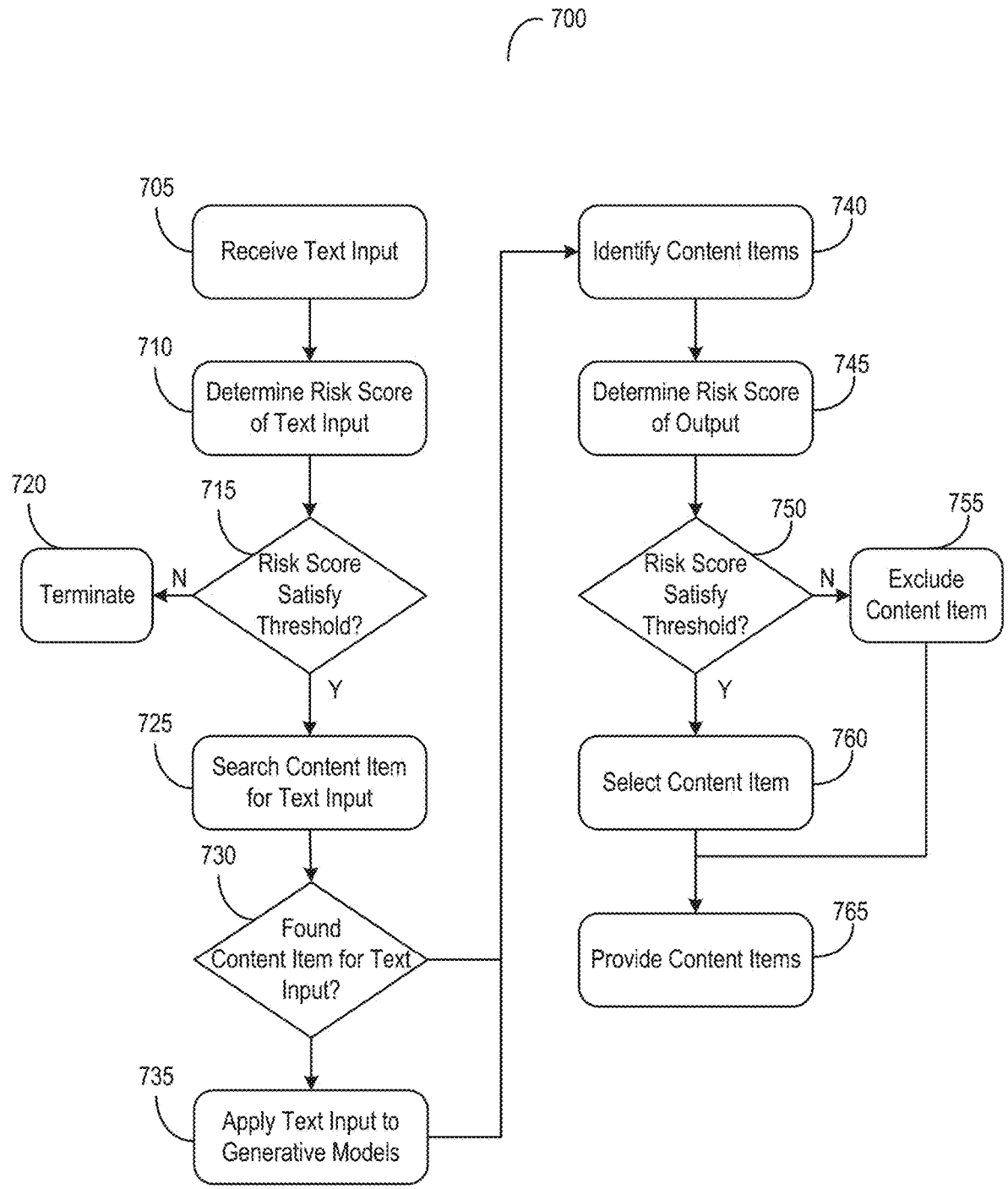
FIG. 7 depicts a flow diagram of a method of generating and regulating content for targeted messages in accordance with an illustrative embodiment.

Referring now to FIG. 7, depicted is a method 700 for generating and regulating content for targeted messages. The method 700 can be implemented or performed using any of the components detailed herein such as the data processing system 105, the administrator device 190, the end user device 110, and the database 135, among others. Under method 700, a computing system (e.g., the data processing system 105 or the administrator device 190 or both) may receive a text input (e.g., the input 225) (705). The computing system may determine risk scores (e.g., the risk scores 235) of the input (710). The computing system may determine if the risk score satisfies a threshold (715). Responsive to determining that the risk score does not satisfy the threshold, the computing system may terminate the process (720). Responsive to determining that the risk score satisfies the threshold, the computing system may search content items (e.g., the content items 180) for the text input (725). The computing system may determine if there are content items corresponding to the text input within a database (e.g., the database 135) (730). Responsive to determining that there are no content items for the text input, the computing system may apply the text input to generative models (e.g., the generative transformer models 165) (735). Responsive to determining that there are one or more content items for the text input or responsive to applying the text input to the generative models, the computing system may identify the content items (740). The computing system may determine a risk score (e.g., the risk score 305) of an output (745). The computing system may determine if the risk score satisfies a threshold (750). If the risk score does not satisfy the threshold, the computing system may exclude the content item (755). Responsive to the risk score satisfying the threshold, the computing system may select the content item (760). The computing system may provide the content items (765).

B. Systems and Methods for Training and Applying Validation Models for Content

Figure 8:
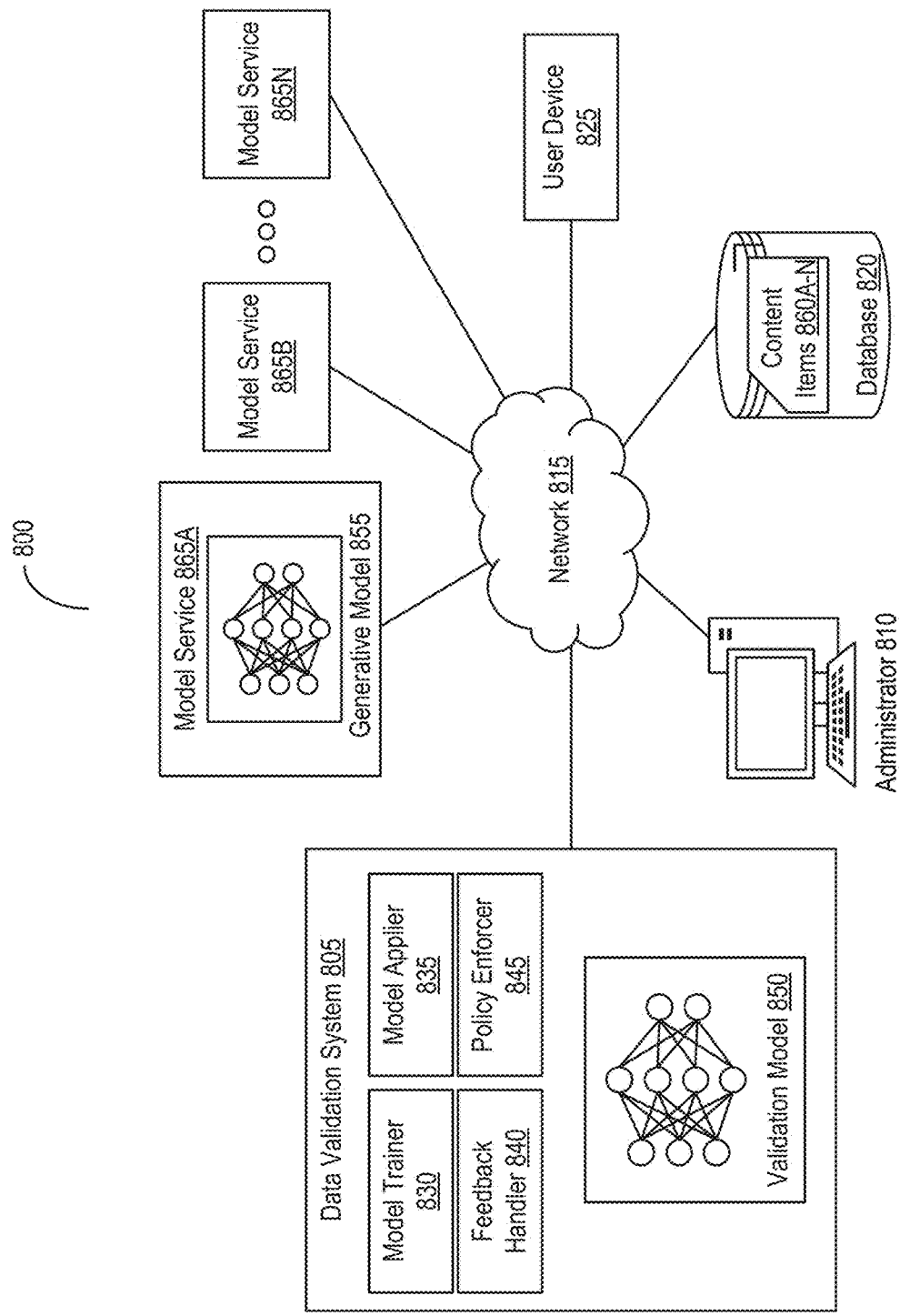
FIG. 8 depicts a block diagram for a process to train and apply validation models to content in accordance with an illustrative embodiment.

Referring now to FIG. 8, depicted is a block diagram for a process 800 for a process to train and apply validation models to content. In an overview, the system 800 may include at least one data validation system 805, an administrator device 810, model services 865A-865N (hereinafter generally referred to as the model service(s) 865), a database 820, and an end user device 825 communicatively coupled with one another via at least one network 815. The model services 865 may include at least one generative model 855. The data validation system 805 may include at least one model trainer 830, at least one model applier 835, at least one feedback handler 840, at least one policy enforcer 845, and at least one validation model 850, among others. The data validation system 805 may include or have access to at least one database 820. The database 820 may store, maintain, or otherwise include one or more content items 860A-N (hereinafter generally referred to as the content item(s) 860), among others. Within the data validation system 805, the model trainer 830 may train the validation models 850. The model applier 835 may apply the validation models 850 to generate an output dataset. The feedback handler 840 may receive feedback from the administrator device 810. The policy enforcer 845 may provide a content item to an end user. In some embodiments, the data validation system 805 may be part of the data processing system 105 as detailed herein.

In further detail, the data validation system 805 may be any computing device comprising one or more processors coupled with memory and software and capable of performing the various processes and tasks described herein. The data validation system 805 may be in communication with end user device 825, the administrator device 810, the model service 865, and the database 820 via the network 815. The data validation system 805 may be situated, located, or otherwise associated with at least one computer system. The computer system may correspond to a data center, a branch office, or a site at which one or more computers corresponding to the data validation system 805 are situated.

The end user device 825 may be any computing device comprising one or more processors coupled with memory and software and capable of performing the various processes and tasks described herein. The end user device 825 may be like or include the end user device 110. The end user device 825 may be in communication with the data validation system 805, the administrator device 810, the model service 865, and the database 820 via the network 815. The end user device 825 may be a smartphone, other mobile phone, tablet computer, wearable computing device (e.g., smart watch, eyeglasses), or laptop computer. The end user device 825 may be provided with one or more content items 860 via the data validation system 805, or the end user device 825 may request one or more content items 860 via an interaction with the data validation system 805, such as via an application associated with the user device 825.

The administrator device 810 (sometimes herein referred to as an administrator device) may be any computing device comprising one or more processors coupled with memory and software and capable of performing the various processes and tasks described herein. The administrator device 810 may be like or include the administrator device 190. The administrator device 810 may be in communication with the data validation system 805, the end user device 825, the model services 865, and the database 820 via the network 815. The administrator device 810 may be a smartphone, other mobile phone, tablet computer, wearable computing device (e.g., smart watch, eyeglasses), or laptop computer. The administrator device 810 may be used to access an application.

The database 820 may store and maintain various resources and data associated with the data validation system 805 and the model service 865. The database 820 may include a database management system (DBMS) to arrange and organize the data maintained thereon, such as the content items 860A-N, among others. The database 820 may be in communication with the data validation system 805, the administrator device 810, the end user device 825, and the model services 865 via the network 815. While running various operations, the data validation system 805, the model service 865, and the administrator device 810 may access the database 820 to retrieve identified data therefrom. The data validation system 805, the model service 865, and the administrator device 810 may also write data onto the database 820 from running such operations.

On the database 820, the content items 860 may be in any modality, such as text, image, audio, video, or multimedia content, among others, or any combination thereof. The content items 860 can be like or include the content items 180. The content items 860 can be stored and maintained in the database 820 using one or more files. For instance, for text, the content items 860 can be stored as text files (TXT), rich text files (RTF), extensible markup language (XML), and hypertext markup language (HTTP), among others. For an image, the content items 860 may be stored as a joint photographic experts' group (JPEG) format, a portable network graphics (PNG) format, a graphics interchange format (GIF), or scalable vector graphics (SVG) format, among others. For audio, the content items 860 can be stored as a waveform audio file (WAV), motion pictures expert group formats (e.g., MP3 and MP4), and Ogg Vorbis (OGG) format, among others. For video, the content items 860 can be stored as a motion pictures expert group formats (e.g., MP3 and MP4), QuickTime movie (MOV), and Windows Movie Video (WMV), among others. For multimedia content, the content items content items 860 can be an audio video interleave (AVI), motion pictures expert group formats (e.g., MP3 and MP4), QuickTime movie (MOV), and Windows Movie Video (WMV), among others.

Each content item 860 may identify or include information to be presented via the end user device 825 or the administrator device 810. For example, the content items 860 may be presented to an end user or administrator through a message transmitted to the end user device 825 or the administrator device 810, respectively. The message may be in any format, such as a short message/messaging service (SMS), a multimedia messaging service (MMS), or as an instruction to present via a display associated with the user device 825 or the administrator device 810, among others.

The content items 860 of the message may include reminders to perform a task of the session. The message may be derived from a library of pre-generated psychotherapy messages or a library of pre-generated engagement (reminder) messages. The message may include reminders for the end user to complete the therapy sessions, to take medication, or to complete a task of the regimen. The message may include an activity for the end user to perform or a lesson for the end user to engage with. The content items 860 may also include a mechanism for responding, such as a link, chat box, or indication to respond to the message.

The content items 860 may include or correspond to one or more texts such as articles, summaries, or publications. For example, the content items 860 can include research articles, review articles, case reports, clinical trial protocols, or editorials, among others. The content items 860 can include texts for submission to governmental agencies, subject matter experts, scientific journals, or conferences, among others. For example, the content items 860 can include clinical trial protocols related to a treatment provided for a condition of an end user for submission to the Food and Drug Administration (FDA), a medical journal, or for internal distribution.

The condition of the end user may include, for example, chronic pain (e.g., associated with or include arthritis, migraine, fibromyalgia, back pain, Lyme disease, endometriosis, repetitive stress injuries, irritable bowel syndrome, inflammatory bowel disease, and cancer pain), a skin pathology (e.g., atopic dermatitis, psoriasis, dermatillomania, and eczema), a cognitive impairment (e.g., mild cognitive impairment (MCI), Alzheimer's, multiple sclerosis, and schizophrenia), a mental health condition (e.g., an affective disorder, bipolar disorder, obsessive-compulsive disorder, borderline personality disorder, and attention deficit/hyperactivity disorder), a substance use disorder (e.g., opioid use disorder, alcohol use disorder, tobacco use disorder, or hallucinogen disorder), and other conditions (e.g., narcolepsy and oncology or cancer), among others.

The end user may be at least partially concurrently taking medication to address the condition while being provided content items 860 generated during the session to generate or modify the content items 860. For instance, if the medication is for pain, the end user may be taking acetaminophen, a nonsteroidal anti-inflammatory composition, an antidepressant, an anticonvulsant, or other composition, among others. For skin pathologies, the end user may be taking a steroid, antihistamine, or topic antiseptic, among others. For cognitive impairments, the end user may be taking cholinesterase inhibitors or memantine, among others. For narcolepsy, the end user may be taking a stimulant or antidepressant, among others. The end user may also participate in other psychotherapies for these conditions.

The content items 860 can be human-created, computer-generated, or a combination thereof. In some embodiments, a person can provide the content items 860 through the administrator device 810. For example, the administrator device 810 may upload, provide, or transfer one or more content items 860 for storage in the database 820. The content items 860 can be computer-generated, such as by the generative model 855. In some embodiments, the administrator device 810 may provide inputs to the model service 865 to create one or more content items 860 using the generative model 855. For example, the administrator device 810 can provide text, images, videos, or other presentations as input to generate the content items 860. The model services 865 can generate one or more content items 860 from a prompt created by the input from the administrator device 810 using the generative models 855.

The model services 865 can be or include any computing device capable of hosting one or more generative models 855 to generate the content items 860. The model services 865 may be local to the system 800 or may be remote from the system 800 and accessed by the data validation system 805 via the network 815. In some embodiments, the data validation system 805 can maintain one or more model services 865. In some embodiments, the data validation system 805 can access a remote model service 865 to provide inputs to generate the one or more content items 860. The model services 865 can maintain one or more generative models 855.

The generative models 855 (sometimes referred to herein as the generative transformer models 855) may receive inputs in the form of a set of strings (e.g., from a text input) to output content (e.g., the content items 860) in one or more modalities (e.g., in the form of text strings, audio content, images, video, or multimedia content). The generative models 855 can be like or include the generative transformer models 165. The generative model 855 may be a machine learning model in accordance with a transformer model (e.g., generative pre-trained model or bidirectional encoder representations from transformers). The generative transformer model 165 can be a large language model (LLM), a text-to-image model, a text-to-audio model, or a text-to-video model, among others. In some embodiments, the generative model 855 can be a part of data validation system 805, or the data validation system 805 can include the model service 865. In some embodiments, the generative model 855 can be part of a server separate from and in communication with the data validation system 805 via the network 815.

One or more of the generative models 855 can be trained and maintained by the data processing system 105. The generative model 855 can include a set of weights arranged across a set of layers in accordance with the transformer architecture. Under the architecture, the generative model 855 can include at least one tokenization layer (sometimes referred to herein as a tokenizer), at least one input embedding layer, at least one position encoder, at least one encoder stack, at least one decoder stack, and at least one output layer, among others, interconnected with one another (e.g., via forward, backward, or skip connections). In some embodiments, the generative transformer layer can lack the encoder stack (e.g., for an encoder-only architecture) or the decoder stack (e.g., for a decoder-only model architecture). The tokenization layer can convert raw input in the form of a set of strings into a corresponding set of word vectors (also referred to herein as tokens or vectors) in an n-dimensional feature space. The input embedding layer can generate a set of embeddings using the set of words vectors. Each embedding can be a lower dimensional representation of a corresponding word vector and can capture the semantic and syntactic information of the string associated with the word vector. The position encoder can generate positional encodings for each input embedding as a function of a position of the corresponding word vector or by extension the string within the input set of strings.

Continuing on, in the generative model 855, an encoder stack can include a set of encoders. Each encoder can include at least one attention layer and at least one feed-forward layer, among others. The attention layer (e.g., a multi-head self-attention layer) can calculate an attention score for each input embedding to indicate a degree of attention the embedding is to place focus on and generate a weighted sum of the set of input embeddings. The feed-forward layer can apply a linear transformation with a non-linear activation (e.g., a rectified linear unit (ReLU)) to the output of the attention layer. The output can be fed into another encoder in the encoder stack in the generative transformer layer. When the encoder is the terminal encoder in the encoder stack, the output can be fed to the decoder stack.

The decoder stack can include at least one attention layer, at least one encoder-decoder attention layer, and at least one feed-forward layer, among others. In the decoder stack, the attention layer (e.g., a multi-head self-attention layer) can calculate an attention score for each output embedding (e.g., embeddings generated from a target or expected output). The encoder-decoder attention layer can combine inputs from the attention layer within the decoder stack and the output from one of the encoders in the encoder stack, and can calculate an attention score from the combined input. The feed-forward layer can apply a linear transformation with a non-linear activation (e.g., a rectified linear unit (ReLU)) to the output of the encoder-decoder attention layer. The output of the decoder can be fed to another decoder within the decoder stack. When the decoder is the terminal decoder in the decoder stack, the output can be fed to the output layer.

The output layer of the generative model 855 can include at least one linear layer and at least one activation layer, among others. The linear layer can be a fully connected layer to perform a linear transformation on the output from the decoder stack to calculate token scores. The activation layer can apply an activation function (e.g., a softmax, sigmoid, or rectified linear unit) to the output of the linear function to convert the token scores into probabilities (or distributions). The probability may represent a likelihood of occurrence for an output token, given an input token. The output layer can use the probabilities to select an output token (e.g., at least a portion of output text, image, audio, video, or multimedia content with the highest probability). Repeating this over the set of input tokens, the resultant set of output tokens can be used to form the output of the overall generative model 855. While described primarily herein in terms of transformer models, the model service 865 can use other machine learning models to generate and output content. In some implementations, model service 865 may use one or more models maintained by external systems to generate and output content. For example, the data processing system may generate content using one or more models like ChatGPT produced by OpenAI, BARD produced by Google, or LLAMA produced by Meta, among others.

Each generative model 855 can produce one or more of the content items 860 based on a prompt provided to the generative models 855. Each content item 860 produced from a prompt created from a text input provided to the data validation system 805 or the model service 865 can differ, due to differences in each of the generative models 855. As such, a content item 860A may be more suitable than other content items 860B-N for providing to the end user or administrator. For example, the content items 860 generated by the generative models 855 may include inaccuracies, irrelevant content, or hallucinations. In some embodiments, a content item 860A generated by a generative model 855 may not be relevant for a particular end user due to information within the content item 860A, the condition addressed by the content item 860A, a presentation style of the content item 860A, or grand assertions provided by the content item 860A. For example, the content item 860A may assert that it is the "best" method of treatment for a given condition; however, this cannot be asserted and provides false information. For example, the content item 860A may recommend to an end user to consume a meat-based dish, without recognizing that the user has previously indicated vegetarianism. For example, the content item 860A may be in a textual presentation style, although previous behavior of the end user from prior sessions indicates that the end user adheres more consistently to sessions when video content is presented. For example, the content item 860A may generate data which is not substantiated or proven to be true. To moderate the content items 860 produced by the generative models 855, the data validation system 805 may train and apply one or more validation models 850 to the content items 860 to determine compliance of the content items 860.

Each validation model 850 can be a machine learning model trained to determine whether a content item 860 is compliant or non-compliant to a set of criteria. The validation models 850 can be trained to calculate a risk score of a content item 860 corresponding to compliance or non-compliance. Compliance can refer to or include a content item 860 that is below a threshold risk score and thereby may be provisioned. Compliance can refer to or include a content item 860 which is above a threshold accuracy, or which corresponds to criteria for a domain, audience, or combination thereof, as described herein. As such, non-compliance can refer to or include a content item 860 that is at or above a threshold risk score and thereby may not be provisioned by the data validation system 805. A determination of compliance or non-compliance for each content item 860 by the data validation system 805 can further be used to continuously train the generative transformer models 165 to provide more accurate, or less risky, content items 860 over time. The validation models 850 can include one or more natural language models, including the generative transformer models 165 or the generative models 855 described herein. The validation models 850 can include one or more classifier models such as Naive Bayes Classifier, support vector machine (SVM) ensemble classifier, kernel approximation, k-nearest neighbors' classifiers, or decision trees, among others.

One or more of the validation models 850 can accept the content items 860 as input. By accepting the content items 860 as input, the one or more validation models 850 can generate a risk score corresponding to a degree of compliance, or the one or more validation models 850 can generate an indication of compliance or non-compliance. The degree of compliance or indication of compliance can be associated with a likelihood that the content item 860 is a desired content item 860. A desired content item 860 can include the content items 860 in a format specified, for a group of people or an audience specified, for a domain, with a desired accuracy (e.g., correct information, relevant datasets), or with a desired relevancy (e.g., for a user receiving the content items 860 as a part of a digital therapeutics session or an administrator receiving a text in a desired article type), among others.

Figure 9:
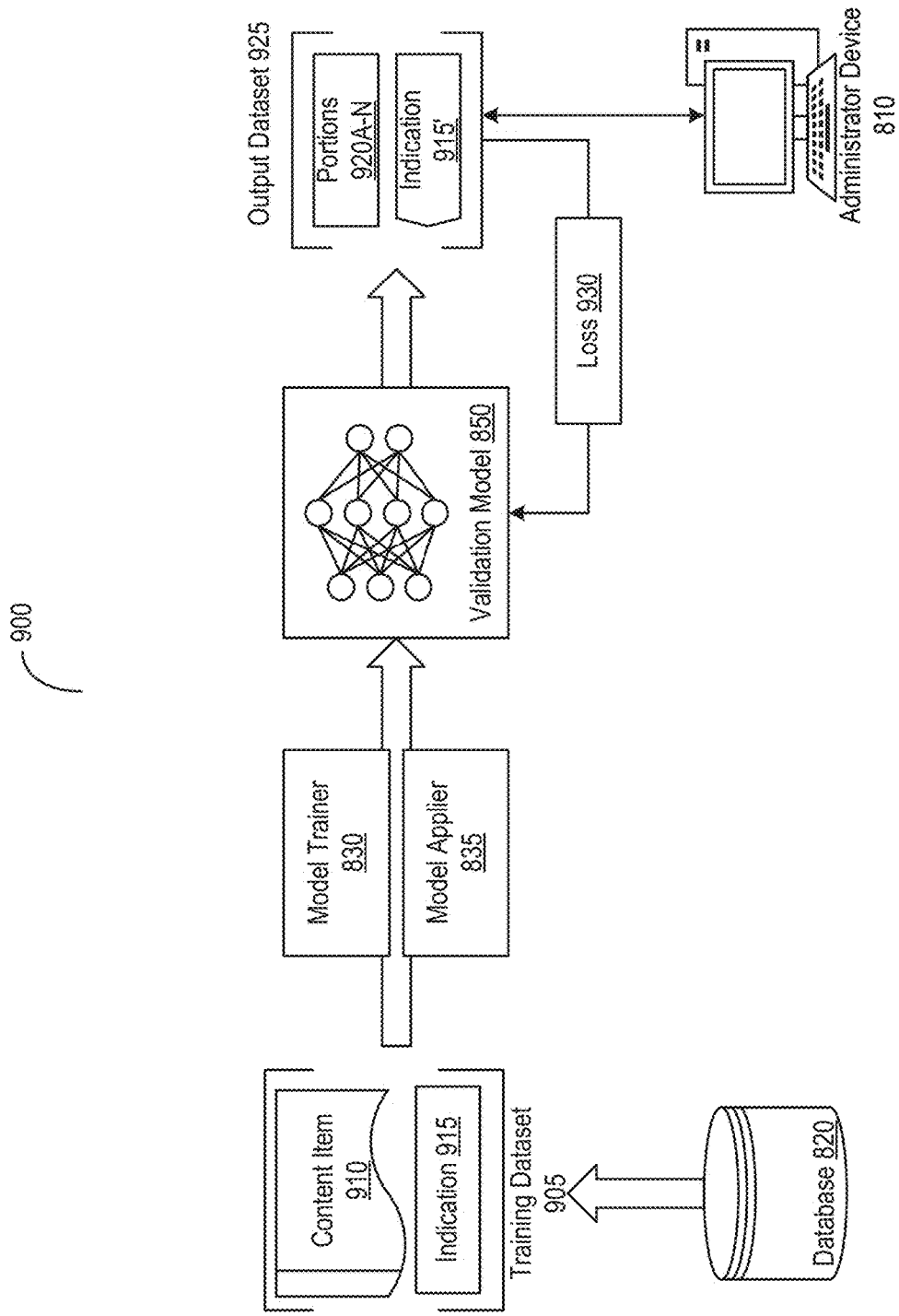
FIG. 9 depicts a block diagram for a process to train a validation model using a training dataset in the system for training and applying validation models to content in accordance with an illustrative embodiment.

Referring now to FIG. 9, depicted is a block diagram for a process 900 to train a validation model using a training dataset in the system 800 for training and applying validation models to content. The process 900 may include or correspond to operations performed in the system 800 to train and apply validation models to content. Under the process 800, the model trainer 830 can train the validation model 850 using a training dataset 905. The model applier 835 can apply a content item of the training dataset 905 to determine a loss 930 of the validation model 850 to iteratively train the validation model 850.

The model trainer 830 executing on the data validation system 805 can retrieve, obtain, or otherwise receive the training dataset 905 from the database 820. The training dataset 905 can include a set of examples for use in training the validation model 850. The training dataset can include a content item 910. The content item 910 can be like the content items 860 or the content items 180. The content item 910 can be an example content item input by the administrator device 810 to train the validation model 850. For example, the content item 910 can include textual content, visual content, haptic content, auditory content, or a combination thereof to provide to a user device.

The content item 910 can be associated with an indication 915. The indication 915 can indicate compliance or non-compliance of the content item 910 with a set of criteria. The content item 910 can correspond to the indication 915 such that the indication 915 can define whether the content item 910 is compliant or non-compliant, as described herein. In some embodiments, the administrator device 810 can assign the indication 915 to the content item 910 of the training dataset 905. In this manner, the content item 910 can be annotated by the indication 915 as compliant or non-compliant.

In some embodiments, the indication 915 can correspond to or include a risk score, such as the risk scores 305 described herein. The risk score can identify a degree of compliance or non-compliance with a set of criteria for provision. For example, the risk score can identify a level, number or score corresponding to how desired the content item 1010 is (e.g., how accurate, risky, relevant, etc.) for provision to a user associated with the end user device 110. In some embodiments, the administrator device 810 may assign the risk score as a part of assigning the indication 915.

In some cases, the content item 910 can include an identification of a domain and the corresponding criteria for that domain. The indication 915 associated with the content item 910 of the training dataset 905 can include a domain identifier, such as the domain identifiers 220, to identify a domain, such as the domains 310, associated with the content item 910. The content item 910 may be associated with, correspond to, or identified by a domain such as the domains described here. For example, the content item 910 may be associated with the indication 915 identifying a product domain, an audience experience domain, a medical domain, a science domain, or a regulatory domain, among others.

In training the models, the model trainer 830 may access the database 820 to retrieve, obtain, or otherwise identify the training dataset 905 to be used to train the validation model 850. In some embodiments, the model trainer 830 can retrieve or identify the examples of the training dataset 905 including the content items 910 stored in the database 820. In some embodiments, the model trainer 830 may access the database 820 to retrieve or identify a set of responses (or feedback data derived therefrom) by end users to previously provided messages or content items. Each response may define or identify the indication 915 as a performance of an activity by an end user in response to presentation of a corresponding message. For instance, the indication 915 may include the response which may include whether the end user performed the specified activity, an indication of favorable reaction with the message, one or more interactions in response to presentation of the message, and a time stamp identifying performance of response, among others.

In some embodiments, the model trainer 830 can initialize the validation models 850. For example, the model trainer 830 can instantiate the validation models 850 by assigning random values to weights of the validation models 850 within layers of the validation models 850. In some embodiments, the model trainer 830 can fine tune a pre-trained machine learning model using the training dataset 905. To train or fine-tune, the model trainer 830 can define, select, or otherwise identify the training dataset 905 from the database 820. The training dataset 905 may be used to input into the validation models 850 to produce an output dataset 925. The output dataset 925 can include an indication 915' to compare against the indication 915. The content item 910 can at least partially overlap and may correspond to a subset of text strings within the training dataset 905. For example, when the content item 910 contains text from messages related to a particular condition, the training dataset 905 may correspond to textual description of the condition and the output dataset 925 may correspond to textual strings of activities to perform, psychoeducation lessons to engage with, reminder to take medication, or a notification to perform a particular activity, among others. The training dataset 905 corresponding to the input and the output dataset 925 may lack overlap. For instance, when the training dataset 905 contains an association between text and images, the content item 910 used as the input may correspond to the text and the output dataset 925 used as the destination may correspond to the image associated with the text.

The model applier 835 may apply the content item 910 to the validation model 850. For example, the model applier 835 can feed or apply the content item 910 into the validation model 850. In applying, the model applier 835 can process the content item 910 to generate the output dataset 925 including the indication 915'. In some embodiments, the model applier 835 may select a validation model 850 to apply the content item 910 based on the domain associated with the content item 910. For example, the model applier 835 may apply content items associated with a medical domain to a first validation model and content items associated with a regulatory domain to a second validation model. In this manner, a set of validation models 850 can be trained for a particular domain.

The validation model 850 may output the output dataset 925 including the indication 915'. In some embodiments, the model applier 835 can determine the indication 915' based on the output dataset 925 to be one of compliance or non-compliance. The indication 915' can be generated by the validation model 850 based on the content item 910. In some embodiments, the model trainer 830 may determine the indication 915' with respect to the domain indicated in the content item 915. For example, the indication 915' can correspond to a compliance within a particular domain. The indication 915' can indicate if the content item 910 corresponds to the domain to which the validation model 850 corresponds.

In some embodiments, the output dataset 925 can include portions 920A-N (hereinafter generally referred to as the portion(s) 920). The portions 920 can include subsections of the content item 910 to be modified or identified as a subsection to modify. The portions 920 can include an indication of the subsections to modify. The validation model 850 can determine the portions 920 with the output dataset 925 responsive to a determination of the indication 915' corresponding to non-compliance, or being below a degree of compliance. The portions 920 may indicate sections of text, images, words, phrasing, or other components of the content item 910 which may be desirable to be edited. In some embodiments, the administrator device 810 can edit the portions 920 of the output dataset 925. In some embodiments, the administrator device 810 can provide the portions 920 within the output dataset 925 upon generation of the output dataset 925. In this manner, the validation model 850 can accept the edits to the portions 920 or the selection of the portions themselves 920 In further iterative training of the validation model 850.

With the determination of the indication 915', the model trainer 830 can compare the indication 915' with the indication 915. The comparison can be between the probabilities (or distribution) of various tokens for the content item 910 (e.g., words for text output) from the output dataset 925 versus the probabilities of tokens in the content item 910. For instance, the model trainer 830 can determine a difference between a probability distribution of the indication 915' versus the indication 915 to compare. Based on the comparison, the model trainer 830 can calculate, determine, or otherwise generate a loss 930. The loss 930 may indicate a degree of deviation of the indication 915' from the indication 915. The loss 930 may be calculated in accordance with any number of loss functions, such as a norm loss (e.g., L1 or L2), mean squared error (MSE), a quadratic loss, a cross-entropy loss, and a Huber loss, among others.

In some embodiments, the model trainer 830 may determine the loss 930 for the output dataset 925 based on the data retrieved from the database 820. In determining, the model trainer 830 may compare the output dataset 925 with the content item 910 to calculate a degree of similarity. The degree of similarity may measure, correspond to, or indicate, for example, a level of semantic similarity (e.g., using a knowledge map when comparing between text of the content item 910 and the output dataset 925), visual similarity (e.g., pixel to pixel value comparison, when comparing between image or frames of the video of the content item 910 and the output dataset 925), or audio similarity (e.g., using a correlation or cosine similarity measure between the audio of the content item 910 and the output dataset 925). The loss 930 may be a function of the degree of similarity, domain, or responses indicating whether users responded to the content item 910 with which the output dataset 925 is compared to, among others. In general, the higher the loss 930, the more the generated output dataset 925 may have deviated from the preference established by a given administrator device 810 in contrivance of the indication 915. Conversely, the lower the loss 930, the less the generated output dataset 925 may have deviated from the indication 915 established by the administrator device 810 and be in conformance with the indication 915. The loss 930 may be calculated to train the validation model 850 to generate risk scores or indication of compliance for the indication 915 for messages with a higher probability of engagement by the user, for content items corresponding to a particular domain or audience, among others.

Using the loss 930, the model trainer 830 can update one or more weights in the set of layers of the validation models 850. The updating of the weights may be in accordance with back propagation and optimization function (sometimes referred to herein as an objective function) with one or more parameters (e.g., learning rate, momentum, weight decay, and number of iterations). The optimization function may define one or more parameters at which the weights of the validation model 850 are to be updated. The optimization function may be in accordance with stochastic gradient descent, and may include, for example, an adaptive moment estimation (Adam), implicit update (ISGD), and adaptive gradient algorithm (AdaGrad), among others. The model trainer 830 and the model applier 835 can iteratively train and apply the validation models 850 until convergence. Upon convergence, the model trainer 830 can store and maintain the set of weights for the set of layers of the validation model 850.

Figure 10:
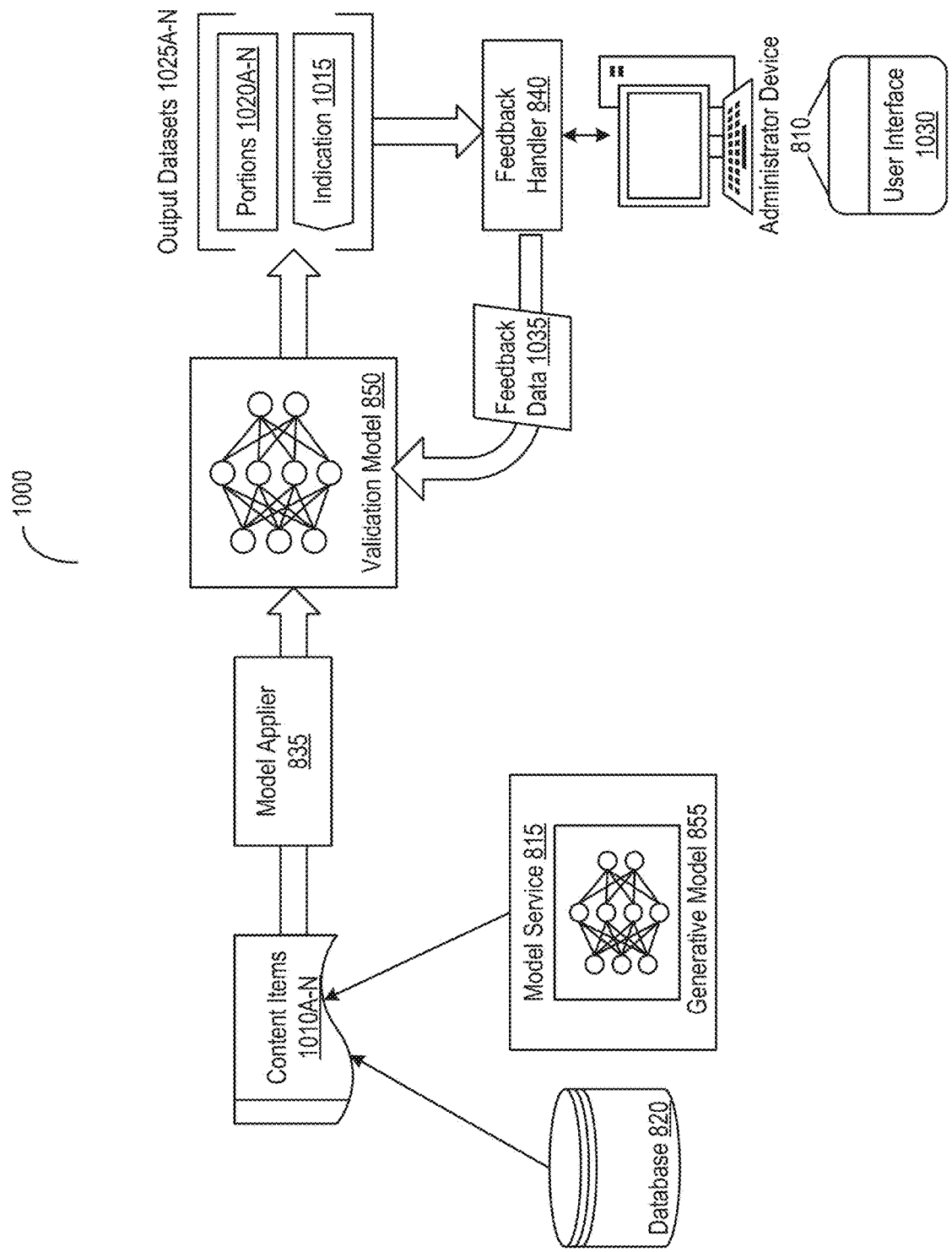
FIG. 10 depicts a block diagram for a process to incorporate feedback for a validation model in the system for training and applying validation models to content in accordance with an illustrative embodiment.

Referring now to FIG. 10, depicted is a block diagram for a process 1000 to incorporate feedback for a validation model in the system for training and applying validation models to content. The process 1000 may include or correspond to operations performed in the system 800 to train and apply validation models to content. Under the process 1000, the model applier 835 may apply content items 1010A-N (hereinafter generally referred to as the content item(s) 1010) to the trained validation model 850. The validation model 850 may generate output datasets 1025A-N (hereinafter generally referred to as the output dataset(s) 1025). The feedback handler 840 may present the output datasets 1025 to the administrator device 810 and may receive feedback data 1035 from the administrator device 810.

Upon convergence of the loss 930 to a threshold level, the model applier 835 may identify the content items 1010 from the database 820 or the model service 865. The content items 1010 can be previously generated content items stored in the database 820. The content items 1010 can include content items generated by one or more of the model services 865. The model applier 835 can provide the identified content items 1010 as input to the validation model 850. In some embodiments, the model applier 835 can provide the content items 1010 based on a domain corresponding to the content items 1010 or a domain of each content item 1010. For example, a first content item 1010A may correspond to a product domain and a second content item 1010B may correspond to an audience experience domain. The model applier 835 may select a first validation model corresponding to a product domain to apply to the first content item 1010A and a second validation model corresponding to an audience experience domain to apply to the second content item 1010B.

By applying the validation model 850, the model applier 835 can generate at least one output dataset 1025. The output dataset 1025 can be similar to the output dataset 925. The output dataset 1025 can indicate whether or not a content item of the content items 1010 is compliant for provision. The output dataset 1025 can include indication 1015. The indication 1015 can indicate whether a particular content item of the content items 1010 is compliant or non-compliant, as described herein. When the content item 1010 is identified as compliant, the content item 1010 may be permitted (e.g., by the data validation system 805) to be provided. On the other hand, when the content item 1010 is identified as non-compliant, the content item 1010 may be restricted (e.g., by the data validation system 805).

The validation model 850 can generate the indication 1015 from the content items 1010 applied by the model applier 835. In some embodiments, the validation model 850 may generate the indication as one of compliance or non-compliance with respect to the domain identified in the content item 1010. For example, the validation model 850 may determine that a first content item 1010A is not compliant (e.g., the indication 1015 indicates non-compliance) for a particular domain, such as a medical or science domain, regulatory domain, product domain, or audience experience domain, among others.

The output datasets 1025 can include portions 1020A-N (hereinafter generally referred to as the portion(s) 1020). The portions 1020 can be like or include the portions 920. The portions 1020 can indicate a subsection of the content item 1010 to be modified, or a subsection of the content item 1010 which may not be in compliance. In some embodiments, the portions 1020 can indicate subsections of the content item 1010 which may be edited to place the content item 1010 in compliance.

The feedback handler 840 can generate instructions to display the output datasets 1025 to the administrator device 810 via a user interface 1030 of the administrator device 810. The user interface 1030 can be like or include the user interface 125 and may include UI elements such as the UI elements 130. The user interface 1030 can be any input/output device to display the output datasets 1025 and accept interactions in regard to the output datasets 1025 from the administrator device 810. The feedback handler 840 may generate instructions to display, render, or otherwise present the output datasets 1025 to the administrator device 810 via the user interface 1030.

The feedback handler 840 may display the output datasets 1025 including the indication 1015. In some embodiments, the feedback handler 840 may display the indication 1015 corresponding to each content item 1010. For example, the feedback handler 840 may generate instructions for the user interface 1030 to display each content item 1010 as corresponding to an indication of compliance, non-compliance, or a risk score indicating a degree of compliance. The feedback handler 840 may generate the instruction to display the portions 1020. In some embodiments, the feedback handler 840 may generate the instructions to display each content item of the content items 1010 corresponding to their respective portions 1020. The feedback handler 840 may generate the instruction to display the portions 1020 responsive to a determination that a respective indication 1015 denotes a respective content item 1010 as non-compliant.

Upon display of the output datasets 1025, the feedback handler 840 may receive an interaction via the user interface 1030. The interaction can be like the interaction 210. The interaction can include an actuation of one or more UI elements of the user interface 1030. The interaction may indicate one or more of the portions 1020 or the indication 1015. The administrator device 810 may select one or more of the portions 1020 from the display on the user interface 1030. The interaction may indicate one or more portions 1020 to edit. For example, the interaction may indicate a portion 1020A of the content item 1010, or the interaction may de-select or un-indicate a portion 1020B determined by the validation model 850.

The interaction may include an edit of the one or more portions, such as editing text, a display, an image, audio, or other such attributes of the content items 1010. For example, the interaction may be to change a volume, tone, or duration of a portion 1020A of an audio content item 1010. For example, the interaction may be to change a color, size, image, or duration of display of a video or image content item 1010B. For example, the interaction may be to change strings, words, formatting, style, or font of a text content item 1010C.

The interaction may include a modification to the indication 1015. The administrator device 810 may change, modify, or override the indication 1015 of the output dataset 1025. In some embodiments, the administrator device 810 may determine that the indication 1015 assigned by the validation model 850 is erroneous, incorrect, or (in the case of a risk score indicating a degree of compliance) the wrong value. The administrator device 810 may provide a different indication via the interaction identifying the content item 1010 as compliant or non-compliant. For example, the validation model 850 may determine that the content item 1010 is compliant. The administrator device 810 may review the indication 1025 and determine that the content item 1010 is in fact non-compliant. The administrator may override the indication 1015 with the different indication via the user interface 1030 associated with the administrator device 810 to determine the indication 1015.

The administrator device 810 may transmit the interaction to the feedback handler 840. The feedback handler 840 may generate feedback data 1035 from the interaction. The feedback data 1035 can include information relating to the portions 1020. For example, the feedback data 1035 can include portions selected by the administrator device 810, portions edited by the administrator device 810, or the edits to the portions 1020 by the administrator device 810. The feedback data 1035 can include information relating to the indication 1015 overridden by the administrator device 810. For example, the feedback data 1035 can include a confirmation of the indication 1015 generated by the validation model 850 for a content item 1010, a change of the indication 1015 generated by the validation model 850 for a content item 1010, an assignment of an indication 1015 or risk score to the content item 1010, or a selection of a domain or multiple domains for the content item 1010.

The feedback handler 840 can provide the feedback data 1035 to the validation model 850 to retrain the validation model 850. In some embodiments, the validation model 850 can be continuously retrained by the model applier 835 and the model trainer 830 using the feedback data 1035 to further reduce the loss 930. The feedback data 1035 may be used to generate a new training dataset including one or more of an indication from the administrator device 810, portions from the administrator device 810, edits to the portions by the administrator device 810, a domain provided by the administrator device 810, among others. In this way, the validation model 850 can continuously learn and improve across different content items and domains.

The feedback handler 840 can determine an association between the content items 1010 and the indications 1015. The feedback handler 840 may store the association in the database 820. The association between the content items 1010 and the indications 1015 can define a content item 1010A as compliant and a content item 1010B as non-compliant. The compliant content item 1010A may permit the content item 1010A to be provided to a user via a user device. The non-compliant content item 1010B may restrict the content item 1010B from being provided to the user. In some embodiments, at least one of the associations can include an association between text and the content item 1010 in another modality, such as an image, audio, video, or multimedia content, among others. The association between the text and the content item 1010 in the other modality can be from a generalized source. For example, the generalized source association can be obtained from a large, predefined corpus identifying associations among words and images. The association between the text and the content item 1010 in the other modality can be from a knowledge domain specific source. For instance, the association can be taken from clinical research, medical journals, or web pages with text and the content in the other modality. Each content item of the content items 1010 can be stored with an associated in the database 820 as a part of a dataset.

Figure 11:
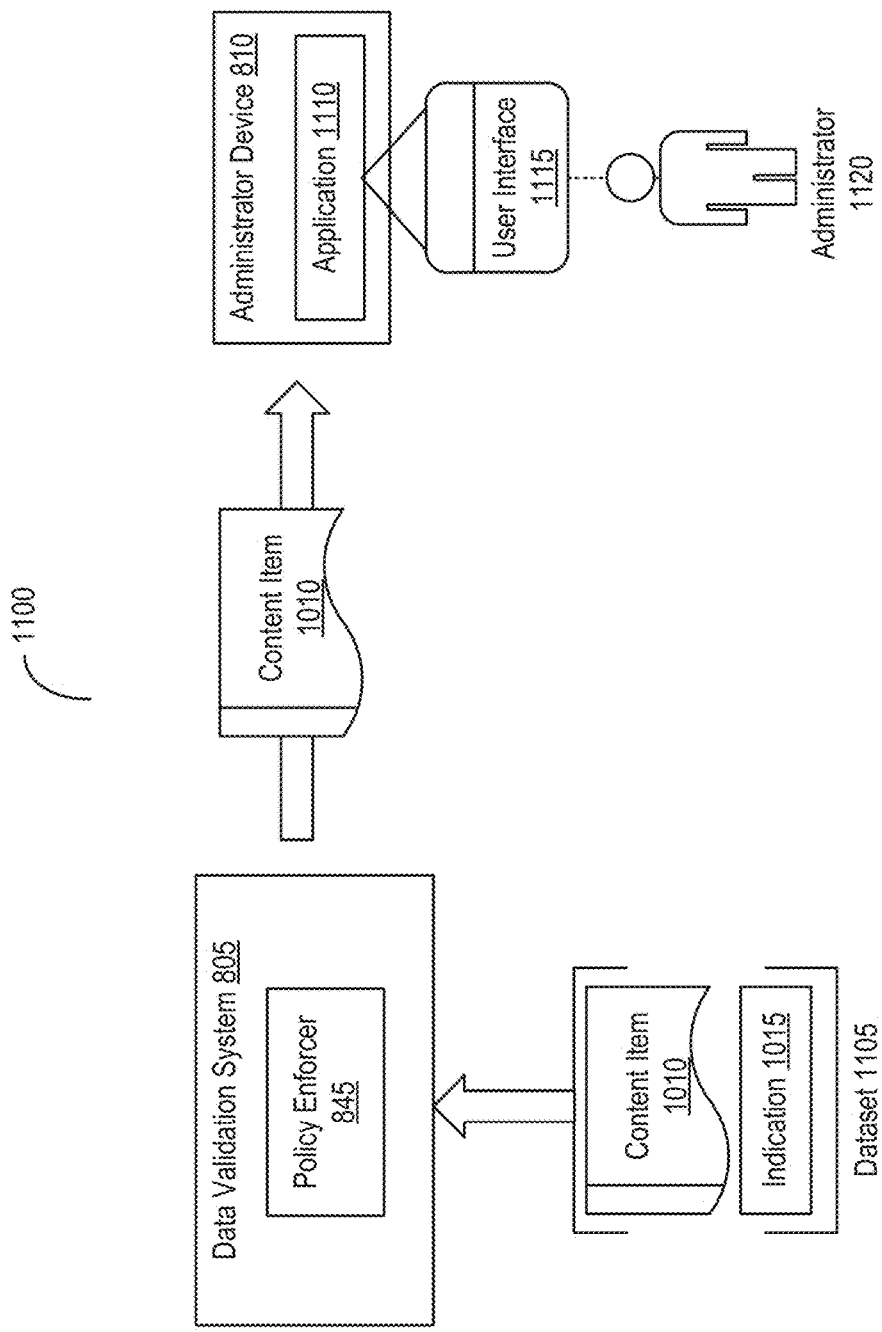
FIG. 11 depicts a block diagram for a process to provide a content item to a user in the system for training and applying validation models to content in accordance with an illustrative embodiment.

Referring now to FIG. 11, depicted is a block diagram for a process 1100 to provide a content item to an administrator in the system for training and applying validation models to content. The process 1100 may include or correspond to operations performed in the system 800 to train and apply validation models to content. Under the process 1100, the policy enforcer 845 may select a content item 1010 to provide to an administrator device 810. The administrator device 810 may present the content item 1010 upon a user interface 1115 in a digital therapeutics session to address a condition of the end user.

Upon storing the association between the content items 1010 and the indication 1015, the policy enforcer 845 operating on the data validation system 805 may select one or more content items 1010 to provide to an administrator 1120. The policy enforcer 845 may select the one or more content items 1010 based on the profile associated with the administrator 1120. In some embodiments, the policy enforcer 845 may select the one or more content items 1010 based on preferences indicated by the profile, an audience indicated by the administrator 1120, among others. The policy enforcer 845 may select the content item 1010 corresponding to an indication 1015 denoting compliance of the content item 1010. For example, the policy enforcer 845 may select for provision one or more content items 1010 which indicate compliance, or which indicate a degree of compliance at or above a threshold degree of compliance. The policy enforcer 845 may restrict a content item 1010 from provision if the association includes an indication 1015 of non-compliance. Conversely, the policy enforcer 845 may permit a content item 1010 for provision if the association includes an indication 1015 of compliance.

Upon selection of the content item 1010 based on at least the indication 1015, the policy enforcer 845 may provide the content item 1010 to an administrator device 810. The administrator device 810 can include an application 1110. The application 1110 operating on the administrator device 810 may be or include a test digital therapeutics application to review content items to provide to the end user in conjunction with a regimen to address a condition of the end user. The application 1110 operating on the administrator device 810 may generate instructions for display of the content item 1010 on a user interface 1115 generated by the application 1110. The user interface 1115 can be like or include the user interfaces 1030, 125, such as including UI elements and accepting an interaction from an administrator 1120 of the device presenting the user interface.

By using the validation model 850, the data validation system 805 may control the provision of content items either generated by generative transformer models or created manually by humans. This may allow automated permission or restriction of content item, thereby reducing the amount of manual effort in reviewing content for any violations for compliance. Provision of content items may expand the functionality provided to end users, thereby improving the utility of end user devices providing digital therapeutics and reducing wasted consumption of computing resources (e.g., processing power and memory) that would have otherwise been spent on ineffective content. In the context of digital therapeutics, the controlling of content items may prevent incorrect or improper information from being provided to the end user, thereby potentially improving the effectiveness of the digital therapeutic content. Furthermore, the increase in engagement can result in higher levels of adherence of the user with the therapy regimen. The higher adherence in turn may lead to a greater likelihood in preventing, alleviating, or treating conditions of the end user.

Figure 12A:
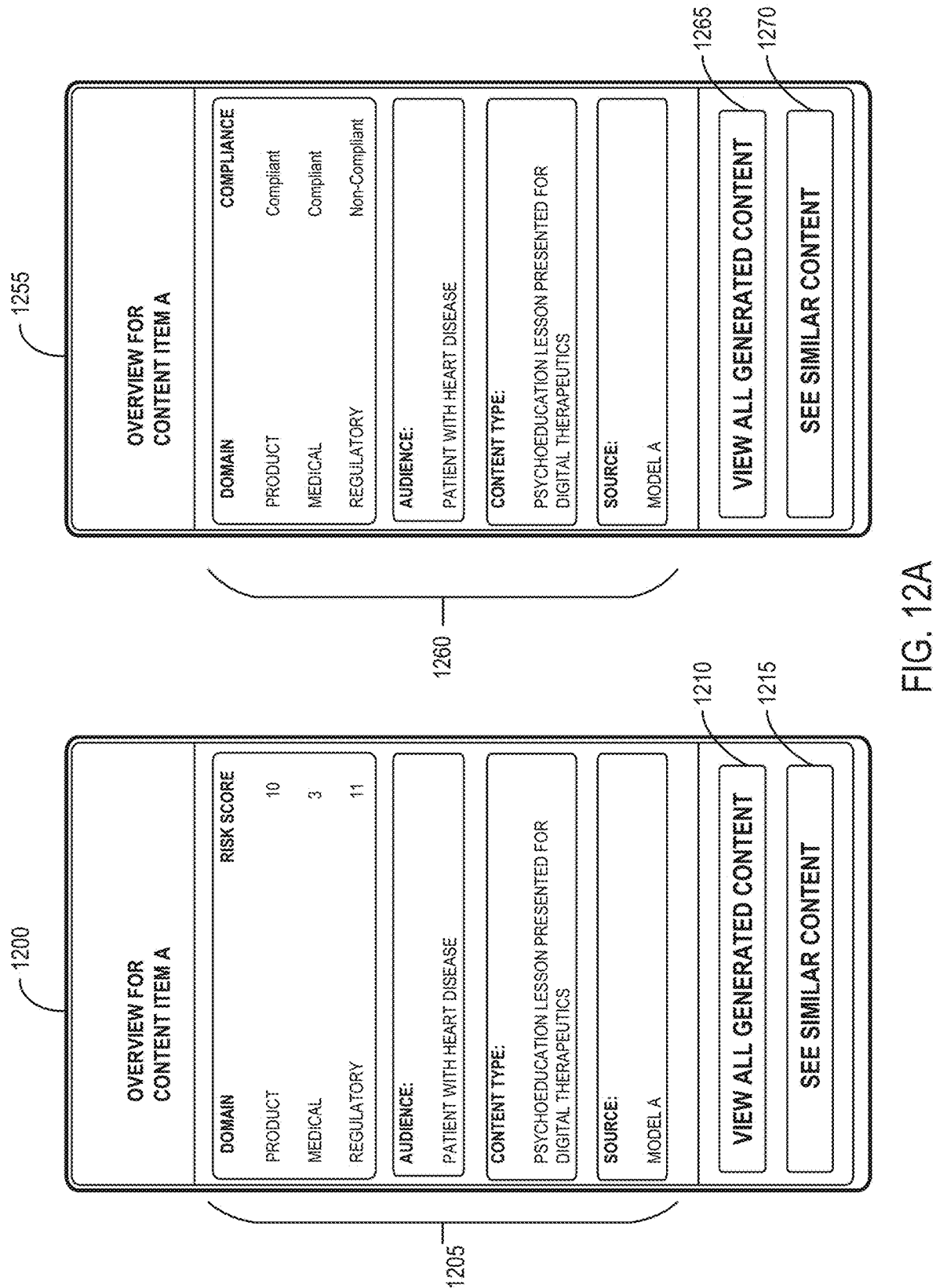
FIG. 12A-C depict example user interfaces for the system for training and applying validation models to content in accordance with an illustrative embodiment.
Figure 12B:
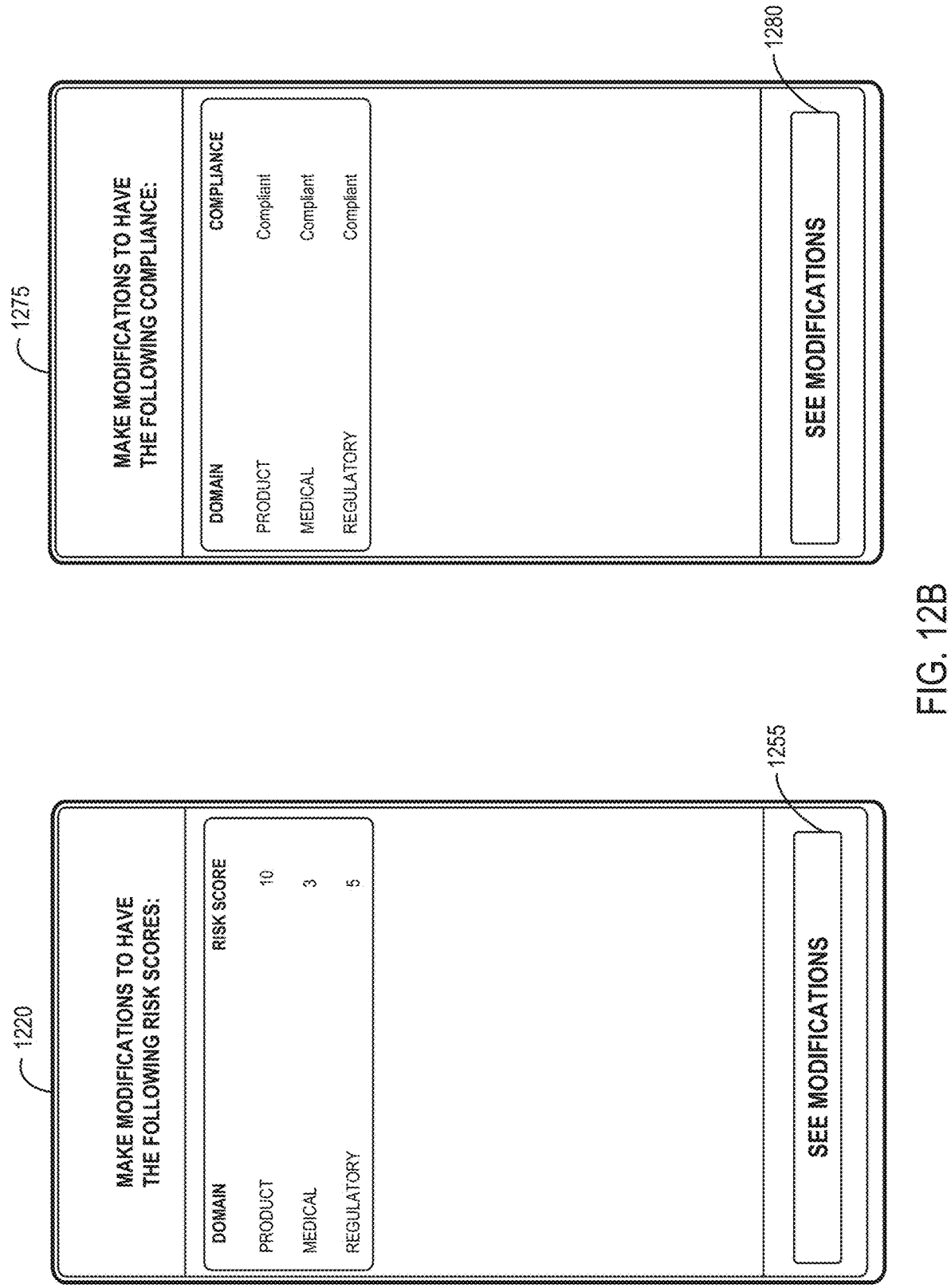
Figure 12C:
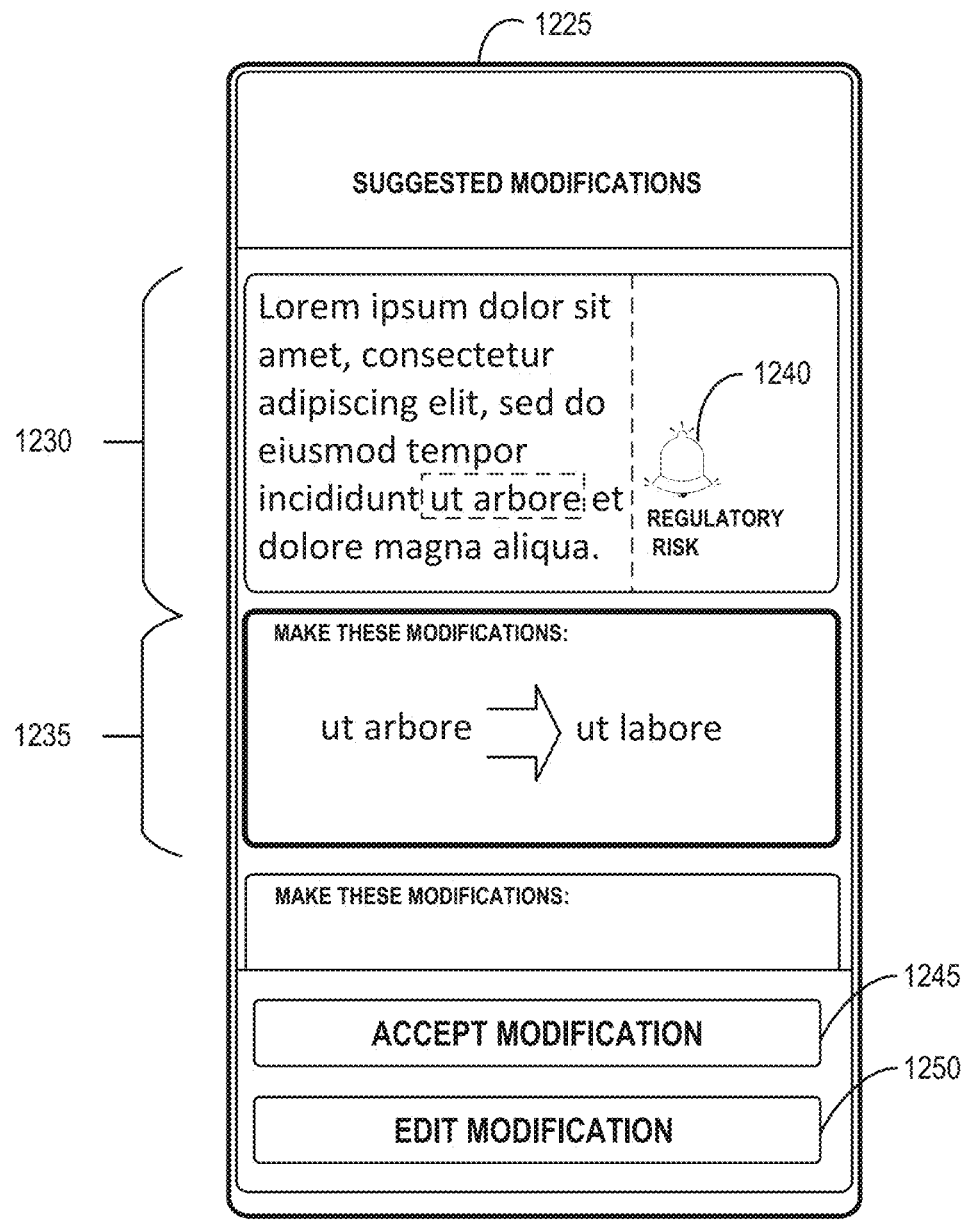

Referring now to FIGS. 12A-C, depicted are example user interfaces for the system for training and applying validation models to content. The example user interfaces can be implemented or performed using any of the components detailed herein such as the data validation system 805, the administrator device 810, and the database 820, among others. Referring now to FIG. 12A, depicted are user interfaces 1200 and 1255 presenting an administrator overview for content item A. The user interface 1200 can be presented in conjunction with the presentation of a message including the content item as described herein. The user interface 1200 can include information 1205, and UI elements 1210 and 1215. The information 1205 can include information related to a generated content item which has been input to one or more validation models as described herein. The information 1205 can include an associated risk score for each domain of the content item, an audience for the content item, a content type of the content item, or a source of the model item (such as which generative model or from which database the content item originated). The user interface 1200 can include the UI element 1210 to view all generated content. The UI element 1210 may, when interacted with by an administrator, cause the user interface 1200 to change to display a listing of all of the content items generated from a prompt or retrieved from the database. The UI element 1215 may, when interacted with by an administrator, show similar content to the content item A. For example, an interaction with the UI element 1215 may cause the user interface 1200 to display content items used to train the generative model which generated the content item A.

As an alternative embodiment to user interface 1200, the user interface 1255 can be presented in conjunction with the presentation of a message including the content item as described herein. The user interface 1255 can include information 1260, and UI elements 1265 and 1270. The information 1260 can include information related to a generated content item which has been input to one or more validation models as described herein. The information 1260 can include an associated indication of compliance for each domain of the content item, an audience for the content item, a content type of the content item, or a source of the model item (such as which generative model or from which database the content item originated). The user interface 1255 can include the UI element 1265 to view all generated content. The UI element 1265 may, when interacted with by an administrator, cause the user interface 1255 to change to display a listing of all of the content items generated from a prompt or retrieved from the database. The UI element 1270 may, when interacted with by an administrator, show similar content to the content item A. For example, an interaction with the UI element 1270 may cause the user interface 1255 to display content items used to train the generative model which generated the content item A.

Referring now to FIG. 12B, depicted are a set of user interfaces 1220 and 1275. The user interface 1220 may depict possible risk scores for each domain associated with a content item. For example, the possible risk score through modification associated with the medical domain for a particular content item is 3. The user interface 1220 may include a UI button 1255. Upon an interaction with the UI button 1255 by the administrator, the user interface 1220 may change to display the user interface 1225 as described in FIG. 12C. As an alternative embodiment to the user interface 1220, the user interface 1275 may depict possible compliance indications for each domain associated with a content item. For example, the possible indication of compliance through modification associated with the medical domain is compliant. The user interface 1275 may include a UI button 1280. Upon an interaction with the UI button 1280 by the administrator, the user interface 1275 may change to display the user interface 1225 as described in FIG. 12C.

Referring now to FIG. 12C, depicted is a user interface 1225. The user interface 1225 may display the suggested modifications to obtain the possible risk scores as depicted in the user interface 1220 or the possible indications of compliance as depicted in the user interface 1275. The user interface 1225 can display the content item 1230. The user interface 1225 can display a portion 1235 of the content item 1230 to modify. The user interface 1225 can include a UI button 1245 and a UI button 1250, among others. The user interface 1225 may display an alert 1240 regarding the content item 1230. The alert 1240 may indicate that the portion 1235 highlighted by the alert 1240 may not be in compliance with one or more domains. The portion 1235 can display a suggested edit or modification to the content item 1230. The UI element 1245 can be to accept the modification presented by the portion 1235. The UI button 1250 can enable the administrator to edit the modification shown in the portion 1235.

Figure 13:
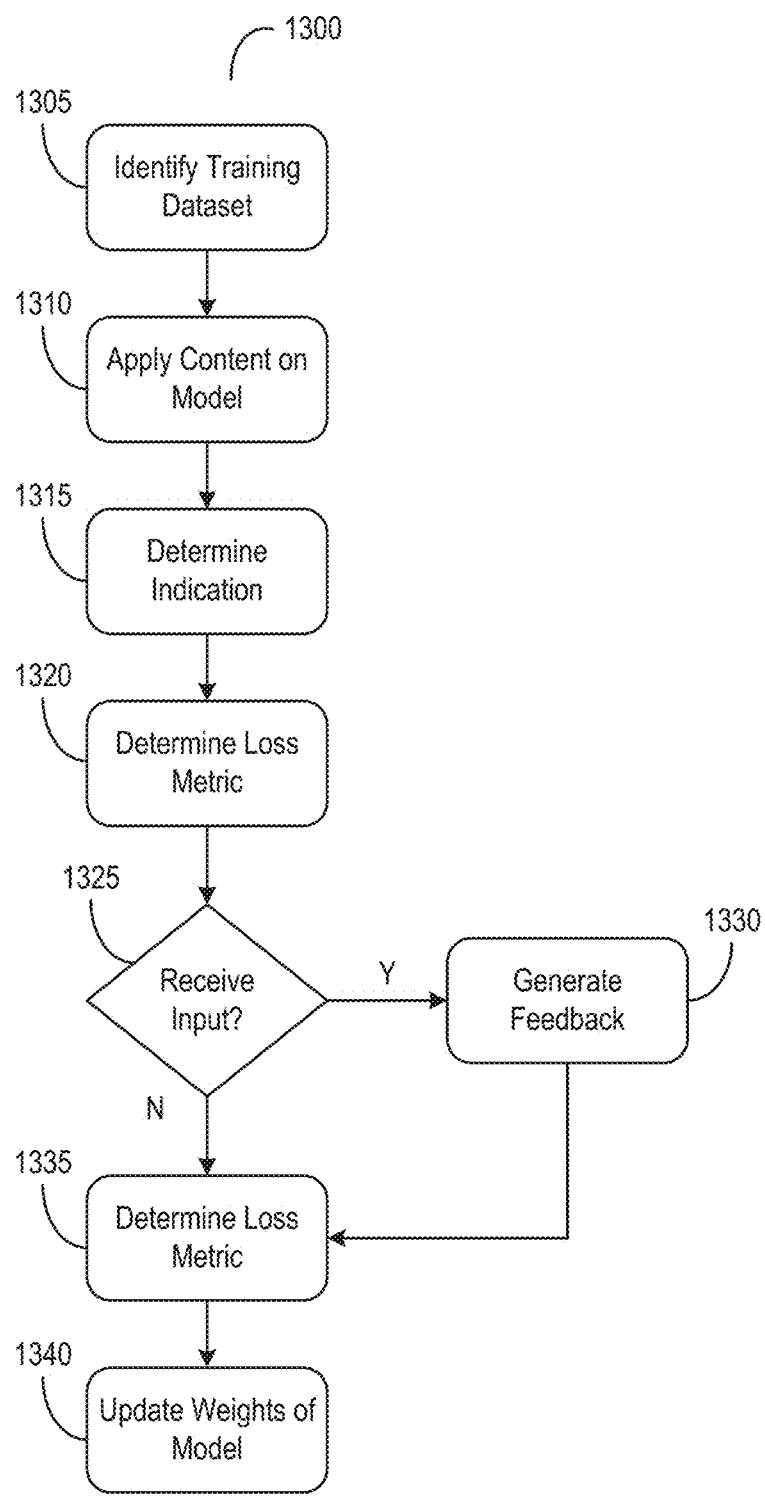
FIG. 13 depicts a flow diagram of a method of training and applying validation models to content in the system for training and applying validation models to content in accordance with an illustrative embodiment.

Referring now to FIG. 13, depicted is a method 1300 for training and applying validation models to content. The method 1300 can be implemented or performed using any of the components detailed herein such as the data validation system 805, the administrator device 810, and the database 820, among others. Under method 1300, a computing system (e.g., the data validation system 805 or the administrator device 810 or both) may identify a training dataset (e.g., the training dataset 905) (1305). The computing system may apply content (e.g., the content item 910) on a model (e.g., the validation model 850) (1310). The computing system may determine an indication (e.g., the indication 915') (1315). The computing system may determine a loss metric (e.g., the loss 930). The computing system may determine if it has received input (1325). Responsive to receiving input, the computing system may generate feedback (e.g., the feedback data 1035) (1330). Responsive to not receiving input, the computing system may determine a loss metric (1335). The computing system may update weights of the model (1340).

Figure 14:
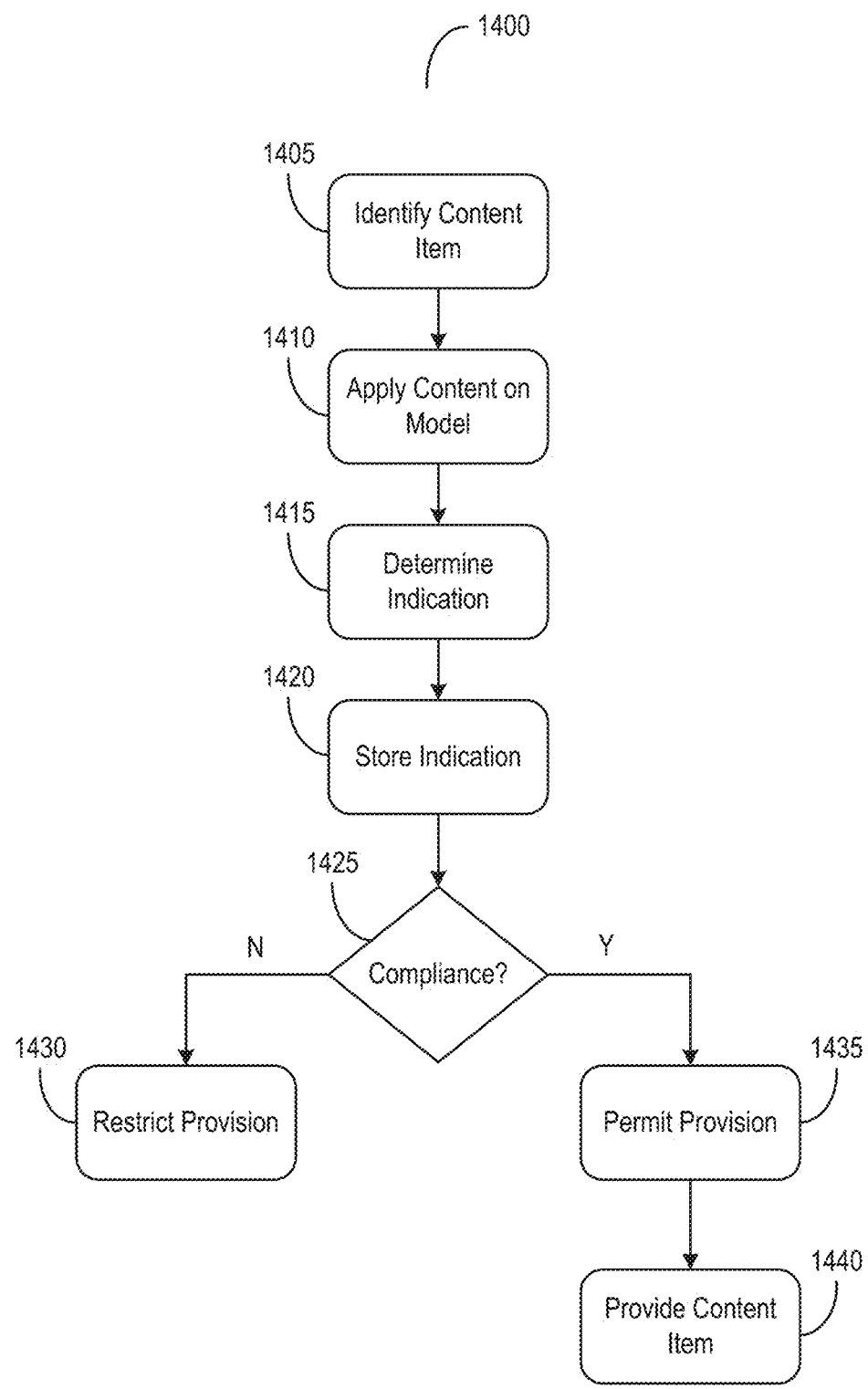
FIG. 14 depicts a flow diagram of a method of providing content to users in the system for training and applying validation models to content in accordance with an illustrative embodiment.

Referring now to FIG. 14, depicted is a method 1400 for providing a validated content item. The method 1400 can be implemented or performed using any of the components detailed herein such as the data validation system 805, the administrator device 810, and the database 820, among others. Under method 1400, a computing system (e.g., the data validation system 805 or the administrator device 810 or both) may identify a content item (e.g., the content item 1010) (1405). The computing system may apply content on the model (1410). The computing system may determine an indication (1415). The computing system may store the indication (1420). The computing system may determine if the indication denotes compliance of the content (1425). Responsive to determining that the indication does not denote compliance, the computing system may restrict provision (1430). Responsive to determining that the indication denotes compliance, the computing system may permit provision (1435). The computing system may provide the content item (1440).

C. Network and Computing Environment

Figure 15:
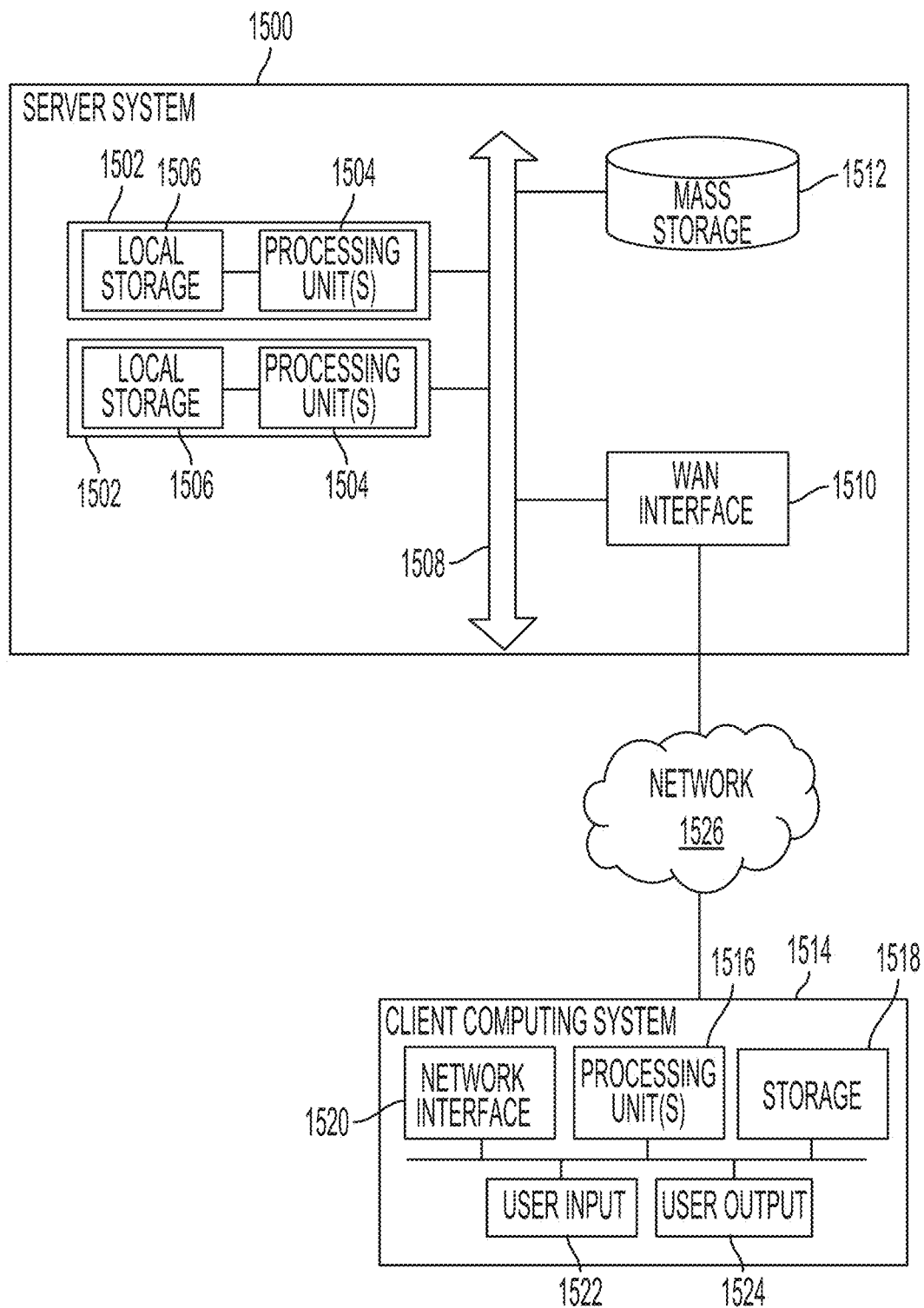
FIG. 15 is a block diagram of a server system and a client computer system in accordance with an illustrative embodiment.

Various operations described herein can be implemented on computer systems. FIG. 15 shows a simplified block diagram of a representative server system 1500, client computer system 1514, and network 1526 usable to implement certain embodiments of the present disclosure. In various embodiments, server system 1500 or similar systems can implement services or servers described herein or portions thereof. Client computer system 1514 or similar systems can implement clients described herein. The system 1500 described herein can be like the server system 1500. Server system 1500 can have a modular design that incorporates a number of modules 1502 (e.g., blades in a blade server embodiment); while two modules 1502 are shown, any number can be provided. Each module 1502 can include processing unit(s) 1504 and local storage 1506.

Processing unit(s) 1504 can include a single processor, which can have one or more cores, or multiple processors. In some embodiments, processing unit(s) 1504 can include a general-purpose primary processor as well as one or more special-purpose co-processors such as graphics processors, digital signal processors, or the like. In some embodiments, some or all processing units 1504 can be implemented using customized circuits, such as application specific integrated circuits (ASICs) or field programmable gate arrays (FPGAs). In some embodiments, such integrated circuits execute instructions that are stored on the circuit itself. In other embodiments, processing unit(s) 1504 can execute instructions stored in local storage 1506. Any type of processors in any combination can be included in processing unit(s) 1504.

Local storage 1506 can include volatile storage media (e.g., DRAM, SRAM, SDRAM, or the like) and/or non-volatile storage media (e.g., magnetic or optical disk, flash memory, or the like). Storage media incorporated in local storage 1506 can be fixed, removable, or upgradeable as desired. Local storage 1506 can be physically or logically divided into various subunits such as a system memory, a read-only memory (ROM), and a permanent storage device. The system memory can be a read-and-write memory device or a volatile read-and-write memory, such as dynamic random-access memory. The system memory can store some or all of the instructions and data that processing unit(s) 1504 need at runtime. The ROM can store static data and instructions that are needed by processing unit(s) 1504. The permanent storage device can be a non-volatile read-and-write memory device that can store instructions and data even when module 1502 is powered down. The term "storage medium" as used herein includes any medium in which data can be stored indefinitely (subject to overwriting, electrical disturbance, power loss, or the like) and does not include carrier waves and transitory electronic signals propagating wirelessly or over wired connections.

In some embodiments, local storage 1506 can store one or more software programs to be executed by processing unit(s) 1504, such as an operating system and/or programs implementing various server functions such as functions of the system 100, 800, or any other system described herein, or any other server(s) associated with system 100, 800, or any other system described herein.

"Software" refers generally to sequences of instructions that, when executed by processing unit(s) 1504, cause server system 1500 (or portions thereof) to perform various operations, thus defining one or more specific machine embodiments that execute and perform the operations of the software programs. The instructions can be stored as firmware residing in read-only memory and/or program code stored in non-volatile storage media that can be read into volatile working memory for execution by processing unit(s) 1504. Software can be implemented as a single program or a collection of separate programs or program modules that interact as desired. From local storage 1506 (or non-local storage described below), processing unit(s) 1504 can retrieve program instructions to execute and data to process to execute various operations described above.

In some server systems 1500, multiple modules 1502 can be interconnected via a bus or other interconnect 1508, forming a local area network that supports communication between modules 1502 and other components of server system 1500. Interconnect 1508 can be implemented using various technologies, including server racks, hubs, routers, etc.

A wide area network (WAN) interface 1510 can provide data communication capability between the local area network (e.g., through the interconnect 1508) and the network 1526, such as the Internet. Other technologies can be used to communicatively couple the server system with the network 1526, including wired (e.g., Ethernet, IEEE 802.3 standards) and/or wireless technologies (e.g., Wi-Fi, IEEE 802.11 standards).

In some embodiments, local storage 1506 is intended to provide working memory for processing unit(s) 1504, providing fast access to programs and/or data to be processed while reducing traffic on interconnect 1508. Storage for larger quantities of data can be provided on the local area network by one or more mass storage subsystems 1512 that can be connected to interconnect 1508. Mass storage subsystem 1512 can be based on magnetic, optical, semiconductor, or other data storage media. Direct attached storage, storage area networks, network-attached storage, and the like can be used. Any data stores or other collections of data described herein as being produced, consumed, or maintained by a service or server can be stored in mass storage subsystem 1512. In some embodiments, additional data storage resources may be accessible via WAN interface 1510 (potentially with increased latency).

Server system 1500 can operate in response to requests received via WAN interface 1510. For example, one of modules 1502 can implement a supervisory function and assign discrete tasks to other modules 1502 in response to received requests. Work allocation techniques can be used. As requests are processed, results can be returned to the requester via WAN interface 1510. Such operation can generally be automated. Further, in some embodiments, WAN interface 1510 can connect multiple server systems 1500 to each other, providing scalable systems capable of managing high volumes of activity. Other techniques for managing server systems and server farms (collections of server systems that cooperate) can be used, including dynamic resource allocation and reallocation.

Server system 1500 can interact with various user-owned or user-operated devices via a wide area network such as the Internet. An example of a user-operated device is shown in FIG. 15 as client computing system 1514. Client computing system 1514 can be implemented, for example, as a consumer device such as a smartphone, other mobile phone, tablet computer, wearable computing device (e.g., smart watch, eyeglasses), desktop computer, laptop computer, and so on.

For example, client computing system 1514 can communicate via WAN interface 1510. Client computing system 1514 can include computer components such as processing unit(s) 1516, storage device 1518, network interface 1520, user input device 1522, and user output device 1524. Client computing system 1514 can be a computing device implemented in a variety of form factors, such as a desktop computer, laptop computer, tablet computer, smartphone, other mobile computing device, wearable computing device, or the like.

Processing unit 1516 and storage device 1518 can be similar to processing unit(s) 1504 and local storage 1506 described above. Suitable devices can be selected based on the demands to be placed on client computing system 1514; for example, client computing system 1514 can be implemented as a "thin" client with limited processing capability or as a high-powered computing device. Client computing system 1514 can be provisioned with program code executable by processing unit(s) 1516 to enable various interactions with server system 1500.

Network interface 1520 can provide a connection to the network 1526, such as a wide area network (e.g., the Internet) to which WAN interface 1510 of server system 1500 is also connected. In various embodiments, network interface 1520 can include a wired interface (e.g., Ethernet) and/or a wireless interface implementing various RF data communication standards such as Wi-Fi, Bluetooth, or cellular data network standards (e.g., 3G, 4G, LTE, etc.).

User input device 1522 can include any device (or devices) via which a user can provide signals to client computing system 1514; client computing system 1514 can interpret the signals as indicative of user requests or information. In various embodiments, user input device 1522 can include at least one of a keyboard, touch pad, touch screen, mouse, or other pointing device, scroll wheel, click wheel, dial, button, switch, keypad, microphone, and so on.

User output device 1524 can include any device via which client computing system 1514 can provide information to a user. For example, user output device 1524 can include display-to-display images generated by or delivered to client computing system 1514. The display can incorporate various image generation technologies, e.g., a liquid crystal display (LCD), light-emitting diode (LED) display including organic light-emitting diodes (OLED), projection system, cathode ray tube (CRT), or the like, together with supporting electronics (e.g., digital-to-analog or analog-to-digital converters, signal processors, or the like). Some embodiments can include a device such as a touchscreen that function as both input and output device. In some embodiments, other user output devices 1524 can be provided in addition to or instead of a display. Examples include indicator lights, speakers, tactile "display" devices, printers, and so on.

Some embodiments include electronic components, such as microprocessors, storage, and memory that store computer program instructions in a computer readable storage medium. Many of the features described in this specification can be implemented as processes that are specified as a set of program instructions encoded on a computer readable storage medium. When one or more processing units execute these program instructions, they cause the processing unit(s) to perform various operations indicated in the program instructions. Examples of program instructions or computer code include machine code, such as is produced by a compiler, and files including higher-level code that are executed by a computer, an electronic component, or a microprocessor using an interpreter. Through suitable programming, processing unit(s) 1504 and 1516 can provide various functionality for server system 1500 and client computing system 1514, including any of the functionality described herein as being performed by a server or client, or other functionality.

It will be appreciated that server system 1500 and client computing system 1514 are illustrative and that variations and modifications are possible. Computer systems used in connection with embodiments of the present disclosure can have other capabilities not specifically described here. Further, while server system 1500 and client computing system 1514 are described with reference to particular blocks, it is to be understood that these blocks are defined for convenience of description and are not intended to imply a particular physical arrangement of component parts. For instance, different blocks can be but need not be in the same facility, in the same server rack, or on the same motherboard. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Embodiments of the present disclosure can be realized in a variety of apparatus including electronic devices implemented using any combination of circuitry and software.

While the disclosure has been described with respect to specific embodiments, one skilled in the art will recognize that numerous modifications are possible. Embodiments of the disclosure can be realized using a variety of computer systems and communication technologies, including, but not limited to, specific examples described herein. Embodiments of the present disclosure can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may refer to specific hardware and software components, those skilled in the art will appreciate that different combinations of hardware and/or software components may also be used and that particular operations described as being implemented in hardware might also be implemented in software or vice versa.

Computer programs incorporating various features of the present disclosure may be encoded and stored on various computer readable storage media; suitable media include magnetic disk or tape, optical storage media such as compact disk (CD) or digital versatile disk (DVD), flash memory, and other non-transitory media. Computer readable media encoded with the program code may be packaged with a compatible electronic device, or the program code may be provided separately from electronic devices (e.g., via Internet download or as a separately packaged computer-readable storage medium).

Thus, although the disclosure has been described with respect to specific embodiments, it will be appreciated that the disclosure is intended to cover all modifications and equivalents within the scope of the following claims.

What is claimed is:

1. A method, comprising:
   identifying, by one or more processors, first digital content to be provided via a network;
   applying, by the one or more processors, the first digital content to a machine learning (ML) model having a set of weights to generate a first output, wherein the ML model is trained by:
      identifying a training dataset including a plurality of examples, each example of the plurality of examples identifying respective second digital content and a first indication identifying one of compliance or non-compliance for provision,
      applying the second digital content from an example of the plurality of examples of the training dataset into the ML model to generate a second output,
      determining, from the second output, a second indication of the second digital content as one of compliant or non-compliant used to control provision,
      comparing the first indication from the example of the training dataset with the second indication determined by the ML model, and
      updating, responsive to comparing the first indication with the second indication, at least one of the set of weights of the ML model using the comparison to further train the ML model;
   determining, by the one or more processors, from the first output, an indication of the first digital content as non-compliant;
   storing, by the one or more processors, using one or more data structures, an association between the first digital content and the indication to restrict the first digital content from provision responsive to determining the indication of the first digital content as non-compliant; and
   generating, by the one or more processors, based on applying the ML model, a portion identifying at least a subsection of the first digital content to be modified, responsive to determining the indication of the first digital content as non-compliant.

2. The method of claim 1, further comprising:
   receiving, by the one or more processors, an identification of the first digital content as associated with at least one domain of a plurality of domains; and
   selecting, by the one or more processors, from a plurality of ML models, the ML model corresponding to the at least one domain to apply to the first digital content, and
   wherein determining the indication further comprises determining the indication of the first digital content as non-compliant with respect to the at least one domain.

3. The method of claim 1, wherein generating the portion further comprises generating, based on applying the ML model, the portion to replace the subsection within the first digital content, responsive to determining the indication of the first digital content as non-complaint.

4. The method of claim 1, further comprising selecting, by the one or more processors, from a plurality of content items, one of a first content item or a second content item as the first digital content for provision based on a respective indication of each of the plurality of content items as one of compliant or non-complaint determined using the ML model.

5. The method of claim 1, further comprising:
receiving, by the one or more processors, via a user interface, a selection of a third indication identifying the first digital content as compliant or non-compliant; and
overriding, by the one or more processors, the indication from the ML model with the third indication received via the user interface.

6. The method of claim 1, wherein each example of the plurality of examples of the training dataset further identifies a first risk score identifying a degree of compliance or non-compliance for provision for the second digital content, wherein determining the second indication further comprises determining a second risk score identifying the degree of compliance or non-compliance for provision for the first digital content.

7. The method of claim 1, wherein the first digital content comprises at least one of textual content or visual content to be provided to a device for presentation in a session for an audience.

8. A method, comprising:
identifying, by one or more processors, a training dataset including a plurality of examples, each example of the plurality of examples identifying respective first digital content and a first indication identifying one of compliant or non-complaint for provision of the first digital content via a network, by (i) restricting the first digital content from provision when non-compliant, and (ii) permitting the first digital content to be provided when compliant;
applying, by the one or more processors, the first digital content from an example of the plurality of examples of the training dataset into a machine learning (ML) model comprising a set of weights to generate an output;
determining, by the one or more processors, from the output, a second indication of the first digital content as one of compliant or non-complaint used to control provision;
comparing, by the one or more processors, the first indication from the example of the training dataset with the second indication determined by the ML model;
updating, by the one or more processors responsive to comparing the first indication with the second indication, at least one of the set of weights of the ML model using the comparison between the first indication and the second indication to further update the ML model; and
storing, by the one or more processors, the set of weights of the ML model to apply to determine the second indication of second digital content as one of compliant or non-complaint.

9. The method of claim 8, further comprising:
receiving, by the one or more processors, via a user interface, a selection of an indication identifying the second digital content as compliant or non-compliant;
comparing, by the one or more processors, the indication determined from the output of the ML model and the indication from the user interface; and
re-training, by the one or more processors, the ML model in accordance with the comparison.

10. The method of claim 8, further comprising receiving, by the one or more processors, feedback data identifying a portion identifying at least a subsection in the first digital content to be modified, responsive to determining an indication of the first digital content as non-complaint.

11. The method of claim 10, further comprising re-training, by the one or more processors, the ML model using the portion to modify in the first digital content.

12. The method of claim 8, further comprising modifying, by the one or more processors, a prompt applied to a generative transformer model used to output the first digital content, responsive to determining the second digital content as non-compliant, wherein the generative transformer model is a part of or separate from the ML model.

13. The method of claim 8, further comprising re-training, by the one or more processors, a generative transformer model used to generate the first digital content, based on an indication of the second digital content as one of non-complaint or complaint.

14. The method of claim 8, wherein each example of the plurality of examples of the training dataset further identifies a first risk score identifying a degree of compliance or non-compliance for provision for the first digital content,
wherein applying further comprises applying the first digital content from an example of the plurality of examples of the training dataset to the ML model to determine a second risk score identifying the degree of compliance or non-compliance for provision for the first digital content, and
wherein updating at least one of the set of weights of the ML model in accordance with a comparison between the first risk score and the second risk score for the example.

15. The method of claim 8, wherein each example of the plurality of examples of the training dataset further includes an identification of the first digital content as a domain of a plurality of domains and the first indication identifying one of compliance or non-compliance with respect to the domain, and further comprising:
identifying, by the one or more processors, from a plurality of ML models, the ML model corresponding to the domain to apply to the first digital content; and
wherein determining the second indication further comprises determining the second indication of the first digital content as one of complaint or non-compliant.

16. A system, comprising:
one or more processors coupled with memory, configured to:
identify a first digital content to be provided via a network;
apply the first digital content to a machine learning (ML) model having a set of weights to generate a first output, wherein the ML model is trained by:
identifying a training dataset including a plurality of examples, each example of the plurality of examples identifying respective second digital content and a first indication identifying one of compliance or non-compliance for provision,
applying the second digital content from an example of the plurality of examples of the training dataset into the ML model to generate a second output, determining, from the second output, a second indication of the second digital content as one of compliant or non-compliant used to control provision, comparing the first indication from the example of the training dataset with the second indication determined by the ML model, and updating, responsive to a comparison of the first indication with the second indication, at least one of the set of weights of the ML model in accordance with using the comparison;

determine, from the first output, an indication of the first digital content as non-compliant to further train the ML model;

store, using one or more data structures, an association between the first digital content and the indication restrict the first digital content from provision responsive to determining the indication of the first digital content as non-compliant; and generate, based on applying the ML model, a portion identifying at least a subsection of the first digital content to be modified, responsive to determining the indication of the first digital content as non-compliant.

17. The system of claim 16, wherein the one or more processors are further configured to:

receive an identification of the first digital content as associated with at least one domain of a plurality of domains;

select, from a plurality of ML models, the ML model corresponding to the at least one domain to apply to the first digital content; and determine the indication of the first digital content as one of compliant or non-compliant with respect to the at least one domain.

18. The system of claim 16, wherein the one or more processors are further configured to generate, based on applying the ML model, the portion to replace the subsection within the first digital content, responsive to determining the indication of the first digital content as non-complaint.

19. The system of claim 16, wherein the one or more processors are further configured to select, from a plurality of content items, one of a first content item or a second content item as the first digital content for provision based on a respective indication of each of the plurality of content items as one of compliant or non-complaint determined using the ML model.

20. The system of claim 16, wherein the first digital content comprises at least one of textual content or visual content to be provided to a device for presentation in a session.

21. A method, comprising:

identifying, by one or more processors, first digital content to be provided via a network;

applying, by the one or more processors, the first digital content to a machine learning (ML) model having a set of weights to generate a first output, wherein the ML model is trained by:

identifying a training dataset including a plurality of examples, each example of the plurality of examples identifying respective second digital content and a first indication identifying one of compliance or non-compliance for provision, applying the second digital content from an example of the plurality of examples of the training dataset into the ML model to generate a second output, determining, from the second output, a second indication of the second digital content as one of compliant or non-compliant used to control provision, comparing the first indication from the example of the training dataset with the second indication determined by the ML model, and updating, responsive to comparing the first indication with the second indication, at least one of the set of weights of the ML model using the comparison to further train the ML model;

determining, by the one or more processors, from the first output, an indication of the first digital content as compliant; and permitting, by the one or more processors, provision of the first digital content responsive to determining the indication of the first digital content as compliant.

22. The method of claim 21, further comprising:

receiving, by the one or more processors, an identification of the first digital content as associated with at least one domain of a plurality of domains; and selecting, by the one or more processors, from a plurality of ML models, the ML model corresponding to the at least one domain to apply to the first digital content, and wherein determining the indication further comprises determining the indication of the first digital content as compliant with respect to the at least one domain.

23. The method of claim 21, further comprising selecting, by the one or more processors, from a plurality of content items, one of a first content item or a second content item as the first digital content for provision based on a respective indication of each of the plurality of content items as one of compliant or non-complaint determined using the ML model.

24. The method of claim 21, further comprising:

receiving, by the one or more processors, via a user interface, a selection of a third indication identifying the first digital content as compliant or non-compliant; and overriding, by the one or more processors, the indication from the ML model with the third indication received via the user interface.

25. The method of claim 21, wherein each example of the plurality of examples of the training dataset further identifies a first risk score identifying a degree of compliance or non-compliance for provision for the second digital content, wherein determining the second indication further comprises determining a second risk score identifying the degree of compliance or non-compliance for provision for the first digital content.

26. The method of claim 21, wherein the first digital content comprises at least one of textual content or visual content to be provided to a device for presentation in a session.

* * * * *